(12) United States Patent
Wangh et al.

(10) Patent No.: US 10,570,462 B2
(45) Date of Patent: *Feb. 25, 2020

(54) KITS AND REACTION MIXTURES FOR ANALYZING SINGLE-STRANDED NUCLEIC ACID SEQUENCES

(71) Applicant: Brandeis University, Waltham, MA (US)

(72) Inventors: Lawrence J. Wangh, Auburndale, MA (US); John E. Rice, Quincy, MA (US); J. Aquiles Sanchez, Framingham, MA (US); Arthur H. Reis, Jr., Arlington, MA (US)

(73) Assignee: Brandeis University, Waltham, MA (US)

( * ) Notice: Subject to any disclaimer, the term of this patent is extended or adjusted under 35 U.S.C. 154(b) by 127 days.

This patent is subject to a terminal disclaimer.

(21) Appl. No.: 15/167,428

(22) Filed: May 27, 2016

(65) Prior Publication Data

US 2016/0258001 A1    Sep. 8, 2016

Related U.S. Application Data

(62) Division of application No. 13/503,324, filed as application No. PCT/US2010/053569 on Oct. 21, 2010, now Pat. No. 9,353,407.

(60) Provisional application No. 61/309,265, filed on Mar. 1, 2010, provisional application No. 61/253,715, filed on Oct. 21, 2009.

(51) Int. Cl.
| | | |
|---|---|---|
| C07H 21/04 | (2006.01) | |
| C12Q 1/689 | (2018.01) | |
| C12Q 1/6818 | (2018.01) | |
| C12Q 1/6858 | (2018.01) | |
| C12Q 1/6827 | (2018.01) | |
| C12Q 1/6886 | (2018.01) | |

(52) U.S. Cl.
CPC .......... *C12Q 1/689* (2013.01); *C12Q 1/6818* (2013.01); *C12Q 1/6827* (2013.01); *C12Q 1/6858* (2013.01); *C12Q 1/6886* (2013.01); *C12Q 2600/156* (2013.01)

(58) Field of Classification Search
USPC .......... 435/6.1, 6.11, 6.12, 91.1, 91.2, 91.51, 435/183; 436/94, 501; 536/23.1, 24.3, 536/24.33, 25.3
See application file for complete search history.

(56) References Cited

U.S. PATENT DOCUMENTS

| | | |
|---|---|---|
| 5,912,148 A | 6/1999 | Eggerding |
| 6,140,054 A | 10/2000 | Wittwer et al. |
| 7,081,336 B2 | 7/2006 | Bao et al. |

(Continued)

FOREIGN PATENT DOCUMENTS

| | | |
|---|---|---|
| WO | WO-00/18965 A1 | 4/2000 |
| WO | WO-2001/031062 | 5/2001 |

(Continued)

OTHER PUBLICATIONS

Allawia et al., "Thermodynamics and NMR of Internal G-T Mismatches in DNA," Biochemistry-US, 36: 19581-10594 (1997).

(Continued)

*Primary Examiner* — Frank W Lu
(74) *Attorney, Agent, or Firm* — Foley Hoag LLP; Brendan T. Jones; Allison Gilder

(57) ABSTRACT

Provided herein are kits for performing for nucleic acid sequences.

15 Claims, 27 Drawing Sheets

Specification includes a Sequence Listing.

(56) References Cited

U.S. PATENT DOCUMENTS

| | | | |
|---|---|---|---|
| 7,198,897 | B2 | 4/2007 | Wangh et al. |
| 7,385,043 | B1 | 6/2008 | Kramer |
| 7,517,977 | B2 | 4/2009 | Wangh et al. |
| 9,353,407 | B2 | 5/2016 | Wangh et al. |
| 2002/0042051 | A1 | 4/2002 | Wittwer |
| 2002/0110450 | A1 | 8/2002 | Swinton |
| 2004/0005580 | A1 | 1/2004 | Dobrowolski et al. |
| 2004/0009584 | A1 | 1/2004 | Mitra et al. |
| 2004/0229253 | A1 | 11/2004 | Hyldig-Nielsen et al. |
| 2007/0015180 | A1 | 1/2007 | Sorge |
| 2009/0209432 | A1 | 8/2009 | Morley et al. |

FOREIGN PATENT DOCUMENTS

| | | |
|---|---|---|
| WO | WO-2003/054233 | 7/2003 |
| WO | WO-2006/044995 A1 | 4/2006 |

OTHER PUBLICATIONS

De Viedma, D.G. et al., "New real-time PCR able to detect in a single tube multiple rifampin resistance mutations and high-level isoniazid resistance mutations in *Mycobacterium tuberculosis*." J Clin Microbiol, 40(3):988-95 (2002).

El-Hajj et al., "Detection of rifampin resistance in *Mycobacterium tuberculosis* in a single tube with molecular beacons," J Clin Microbiol, 39(11): 4131-7 (Nov. 2001).

El-Hajj et al., "Use of sloppy molecular beacon probes for identification of mycobacterial species," J Clin Microbiol, 47(4): 1190-8 (Apr. 2009).

European Search Report from corresponding application No. 15181440.7, dated Dec. 8, 2015.

Hebert et al., "Barcoding animal life: cytochrome c oxidase subunit 1 divergences among closely related species," Proc Biol Sci, 270(Supp 1): S96-9 (Aug. 7, 2003).

Li et al., "A new class of homogeneous nucleic acid probes based on specific displacement hybridization," Nucleic Acids Res, 30(2): E5, 9 pages (Jan. 15, 2002).

Livak et al., "Oligonucleotides with flurescent dyes at opposite ends provide a quenched probe system useful for detecting PCR product and nucleic acid hybridization," PCR Methods Appl., 4(6): 357-62 (1995).

Marras et al., "Multiplex detection of single-nucleotide variations using molecular beacons," Genet Anal, 14(5-6):151-6 (Feb. 1999).

Osborne, "Single-Molecule Late-PCR Analysis of Human Mitochondrial Genomic Sequence Variations," PLOS One, 4(5): C5636 (Jan. 1, 2009).

Piatek et al., "Molecular beacon sequence analysis for detecting drug resistance in *Mycobacterium tuberculosis*," Nat Biotechnol, 16(4): 359-63 (Apr. 1998).

Pierce et al., "Linear-After-The-Exponential (LATE)-PCR: primer design criteria for high yields of specific single-stranded DNA and improved real-time detection," Proc Natl Acad Sci USA, 102(24): 8609-14 (Jun. 14, 2005).

Sanchez et al., "Linear-after-the-exponential (LATE)-PCR: an advanced method of asymmetric PCR and its uses in quantitative real-time analysis," Proc Natl Acad Sci USA, 101(7): 1933-8 (Feb. 17, 2004).

Sanchez et al., "Two-temperature LATE-PCR endpoint genotyping," BMC Biotechnology, Biomed Central LTD, 6(1): 44 (Dec. 4, 2006).

Santalucia J Jr., "A unified view of polymer, dumbbell, and oligonucleotide DNA nearest-neighbor thermodynamics," Proc Natl Acad Sci USA, 95(4): 1460-5 (Feb. 17, 1998).

Shopsin et al., "Evaluation of protein A gene polymrophic region DNA sequencing for typing of *Staphylococcus aureus* strains," J Clin Microbiol, 37(11): 3556-63 (Nov. 1999).

Tyagi et al., "Molecular beacons: probes that fluoresce upon hybridization," Nat Biotechnol, 14(3): 303-8 (Mar. 1996).

Wangh et al., "Overcoming the Crisis of TB and AIDS," Keystone Symposia Global Health Series, Arusha, Tanzania, Oct. 20, 2009, www.brandeis.edu/wanghlab/talks.

Figure 12

```
              ←      121     →←      122    →←
KP    GTCCAGACTCCTACGGGAGGCAGCAGTGGGGAATATTGCACAATGGGCGC 372
EA    GTCCAGACTCCTACGGGAGGCAGCAGTGGGGAATATTGCACAATGGGCGC 380
AB    GCCCAGACTCCTACGGGAGGCAGCAGTGGGGAATATTGGACAATGGGGGG 348
PA    GTCCAGACTCCTACGGGAGGCAGCAGTGGGGAATATTGGACAATGGGCGA 366
COL   GTCCAGACTCCTACGGGAGGCAGCAGTAGGGAATCTTCCGCAATGGGCGA 389
SE    GTCCAGACTCCTACGGGAGGCAGCAGTAGGGAATCTTCCGCAATGGGCGA 389
ENFS  GCCCAGACTCCTACGGGAGGCAGCAGTAGGGAATCTTCGGCAATGGACGA 392
           123     →←     124   →←    125
KP    AAGCCTGATGCAGCCATGCCGCGTGTGTGAAGAAGGCCTTCGGGTTGTAA 422
EA    AAGCCTGATGCAGCCATGCCGCGTGTATGAAGAAGGCCTTCGGGTTGTAA 430
AB    AACCCTGATCCAGCCATGCCGCGTGTGTGAAGAAGGCCTTATGGTTGTAA 398
PA    AAGCCTGATCCAGCCATGCCGCGTGTGTGAAGAAGGTCTTCGGATTGTAA 416
COL   AAGCCTGACGGAGCAACGCCGCGTGAGTGATGAAGGTCTTCGGATCGTAA 439
SE    AAGCCTGACGGAGCAACGCCGCGTGAGTGATGAAGGTCTTCGGATCGTAA 439
ENFS  AAGTCTGACCGAGCAACGCCGCGTGAGTGAAGAAGGTTTTCGGATCGTAA 442
            →←     126   →←      127        →←
KP    AGCACTTTCAGCGGGGAGGAAGGCGGTGAGGTTAATAACCTCATCGATTG 472
EA    AGTACTTTCAGCGAGGAGGAAGGCATTGTGGTTAATAACCGCAGTGATTG 480
AB    AGCACTTTAAGCGAGGAGGAGGCTACTTTAGTTAATACCTAGAGATAGTG 448
PA    AGCACTTTAAGTTGGGAGGAAGGGCAGTAAGTTAATACCTTGCTGTTTTG 466
COL   AACTCTGTTATTAGGGAAGAACATATGTGTAAGTAACTGTGCACATCTTG 487
SE    AACTCTGTTATTAGGGAAGAACAAATGTGTAAGTAACTATGCACGTCTTG 487
ENFS  AACTCTGTTGTTAGAGAAGAACAAGGACGTTAGTAACTGAACGTCCCCTG 490
            128    →←     129    →←    130
KP    --ACGTTACCCGCAGAAGAAGCACCGGCTAACTCCGTGCCAGCAGCCGCG 520
EA    --ACGTTACTCGCAGAAGAAGCACCGGCTAACTCCGTGCCAGCAGCCGCG 528
AB    G-ACGTTACTCGCAGAATAAGCACCGGCTAACTCTGTGCCAGCAGCCGCG 497
PA    --ACGTTACCAACAGAATAAGCACCGGCTAACTTCGTGCCAGCAGCCGCG 514
COL   --ACGGTACCTAATCAGAAGCCACGGCTAACTACGTGCCAGCAGCCGCG 537
SE    --ACGGTACCTAATCAGAAGCCACGGCTAACTACGTGCCAGCAGCCGCG 537
ENFS  --ACGGTATCTAACCAGAAAGCCACGGCTAACTACGTGCCAGCAGCCGCG 540
          →
KP    GTAATACGGAGGGTGCAAGCGTTAATCGGAATTA (SEQ ID No. 54) 554
EA    GTAATACGGAGGGTGCAAGCGTTAATCGGAATTA (SEQ ID No. 55) 562
AB    GTAATACAGAGGGTGCGAGCGTTAATCGGATTTA (SEQ ID No. 56) 531
PA    GTAATACGAAGGGTGCAAGCGTTAATCGGAATTA (SEQ ID No. 57) 548
COL   GTAATACGTAGGTGGCAAGCGTTATCCGGAATTA (SEQ ID No. 58) 571
SE    GTAATACGTAGGTGGCAAGCGTTATCCGGAATTA (SEQ ID No. 59) 571
ENFS  GTAATACGTAGGTGGCAAGCGTTGTCCGGATTTA (SEQ ID No. 60) 574
```

Figure 16

SEQ ID NO: 90    ← 176    →►← 177

301 cactgggact gagacacggc ccagactcct acgggaggca gcagtgggga atattggaca

→►← 178    →►← 179    ►← 180 →

361 atgggggaa ccctgatcca gccataccgc gtgtgtgaag aaggcctat ggttgtaaag

← 181    →►← 182    →►← 183

421 cactttaagc gaggaggagg ctactttagt taatacctag ggatagtgga cgttactcgc

→►← 184    →    ← 185

481 agaataagca ccggctaact ctgtgccagc agccgcggta atacagaggg tgcgagcgtt

→►← 186    →►← 187    →►← 188

541 aatcggattt actgggcgta aagcgtgcgt aggcggctta ttaagtcgga tgtgaaatcc

→►← 189    →►← 190    →►← 191

601 ccgagcttaa cttgggaatt gcattcgata ctggtgagct agagtatggg agaggatggt

→►← 192    →

661 agaattccag gtgtagcggt gaaatgcgta gagatctgga ggaataccga tggcgaaggc

← 193

721 agccatctgg cctaatactg acgctgaggt acgaaagcat ggggagcaaa caggattaga

→

781 taccctggta gtccatgccg taaacgatgt ctactagccg ttggggcctttgaggcttta

KITS AND REACTION MIXTURES FOR ANALYZING SINGLE-STRANDED NUCLEIC ACID SEQUENCES

CROSS-REFERENCE TO RELATED APPLICATION

The present application is a Divisional application of U.S. application Ser. No. 13/503,324, issued as U.S. Pat. No. 9,353,407, which is a national phase application under 35U.S.C. § 371of PCT International Application No. PCT/US2010/053569, filed on Oct. 21, 2010, which claims priority to U.S. Provisional Application 61/309,265, filed Mar. 1, 2010, and to U.S. Provisional Application 61/253,715, filed Oct. 21, 2009, each of which are herein incorporated by reference in their entireties.

FIELD

Provided herein are fluorescence detection methods for nucleic acid sequences and to kits for performing such methods.

BACKGROUND

Homogeneous detection of nucleic acid sequences is well known. Detection may include a dye, for example SYBR Green, that fluoresces in the presence of double-stranded amplification reaction product or a fluorescently labeled oligonucleotide hybridization probe. For hybridization probes, "homogeneous detection" means detection that does not require separation of bound (hybridized to target) probes from unbound probes. Among probes suitable for homogeneous detection are linear probes labeled on one end with a fluorophore and on the other end with a quencher whose absorption spectrum substantially overlaps the fluorophore's emission spectrum for FRET quenching (5' exonuclease probes described in, for example, Livak et al. (1995) PCR Methods Appl. 4:357-362), hairpin probes labeled on one end with a fluorophore and on the other end with a quencher (molecular beacon probes described in, for example, Tyagi et al. (1996) Nature Biotechnology 14:303-308), double-stranded probes having a fluorophore on one strand and a quencher on the other strand (yin-yang probes described in, for example, Li et al. (2002) Nucl. Acids Res. 30, No. 2 e5), linear probes having a fluorophore that absorbs emission from a fluorescent dye and re-emits at a longer wavelength (probes described in, for example, United States published patent application US2002/0110450), and pairs of linear probes, one labeled with a donor fluorophore and one labeled with an acceptor fluorophore that hybridize near to one another on a target strand such that their labels interact by FRET (FRET probe pairs described in, for example, U.S. Pat. No. 6,140,054). Detection methods include methods for detecting nucleic acid sequences in single-stranded targets, double-stranded targets, or both.

Nucleic acid target sequences suitable for probing can in some instances be obtained directly by isolation and purification of nucleic acid in a sample. In other instances nucleic acid amplification is required. Amplification methods for use with homogeneous detection include the polymerase chain reaction (PCR), including symmetric PCR, asymmetric PCR and LATE-PCR, any of which can be combined with reverse transcription for amplifying RNA sequences, NASBA, SDA, and rolling circle amplification. Amplification-detection methods may rely on fluorescence due to probe hybridization, or they may rely on digestion of hybridized probes during amplification, for example, the 5' nuclease amplification-detection method. If a sample contains or is amplified to contain, double-stranded target, for example, the amplification product of a symmetric PCR reaction, but single-stranded target is desired, separation of plus and minus strands can be accomplished by known methods, for example, by labeling one primer with biotin and separating the biotin-containing product strands from the other strands by capture onto an avidin-containing surface, which is then washed.

Certain fluorescent probes useful for homogeneous detection contain a fluorophore-labeled strand that emits a detectable signal when it hybridizes to its target sequence in a sample. For example, a molecular beacon probe is single-stranded and emits a detectable fluorescent signal upon hybridization. A ResonSense® probe is also single stranded and signals only when hybridized provided that the sample contains a dye, generally a SYBR dye, which stimulates hybridized probes by FRET when the dye is stimulated. Yin-yang probes are quenched double-stranded probes that include a fluorophore-labeled strand that emits a detectable signal it hybridizes to its target. FRET probe pairs, on the other hand, are probe pairs that emit a detectable fluorescent signal when both probes of the pair hybridize to their target sequences. Some amplification assays, notably the 5' nuclease assay, include signal generation caused by probe cutting to generate fluorescent probe fragments rather than simply probe hybridization.

Certain probes that generate a signal upon hybridization can be constructed so as to be "allele-specific," that is, to hybridize only to perfectly complementary target sequences, or to be mismatch-tolerant, that is, to hybridize to target sequences that either are perfectly complementary to the probe sequence or are generally complementary but contain one or more mismatches. Allele-specific molecular beacon probes have relatively short probe sequences, generally single-stranded loops not more than 25 nucleotides long with hairpin stems 4-6 nucleotides long, and are useful to detect, for example, single-nucleotide polymorphisms. Marras et al. (1999) Genetic Analysis: Biomolecular Engineering 14: 151-156, discloses a real-time symmetric PCR assay that includes in the reaction mixture four molecular beacons having 16-nucleotide long probe sequences and 5-nucleotide stems, wherein each probe is a different color, that is, includes a fluorophore that is detectably distinguishable by its emission wavelength, and a probe sequence differing from the others by a single nucleotide. The sample is analyzed after each PCR cycle to detect which color arises and thereby to identify which of four possible target sequences perfectly complementary to one of the probes is present in a sample. Mismatch-tolerant molecular beacon probes have longer probe sequences, generally single-stranded loops of up to 50 or even 60 nucleotides with hairpin stems maintained at 4-7 nucleotides. Tyagi et al. European Patent No. 1230387 discloses a symmetric PCR amplification and homogeneous detection assay using a set of four differently colored mismatch-tolerant molecular beacon probes having different probe sequences 40-45 nucleotides long and stems 5-7 nucleotides long, to hybridize competitively to, and thereby interrogate, a 42-nucleotide long hypervariable sequence of mycobacterial 16S rRNA genes to determine which of eight mycobacterial species is present in a sample. The sample is analyzed by determining a ratio of fluorophore intensities at one or more temperatures to identify the species that is present. El-Hajj et al (2009) J. Clin. Microbiology 47:1190-1198, discloses a LATE-PCR amplification and homogeneous detection assay similarly using four differently colored mismatch-tolerant molecular beacon probes having different probe sequences 36-39 nucleotides long and stems 5 nucleotides long to hybridize competitively to, and thereby interrogate, a 39-nucleotide long hypervariable sequence of mycobacterial 16S rRNA genes to determine which of twenty-seven mycobacterial species is present in a sample. Each of the four probes is a "consensus probe," that is, it has a single-stranded loop complementary to multiple species but perfectly complementary to none of them. Genomic DNA from some 27 different species were separately amplified, the Tm of each probe was determined by post-amplification melt analysis, and data was tabulated. To analyze a sample containing an unknown species, the sample was amplified and analyzed as above. The Tm's of all four probes were compared to the tabulated results to identify the species present in the sample.

Multiple probes, both mismatch-tolerant and allele-specific, have been used to interrogate multiple target sequences as well as target sequences longer than a single allele-specific probe. Allele-specific molecular beacon probes have been utilized to interrogate sequences longer than one probe sequence under either of two approaches. Piatek et al. (1998) Nature Biotechnology 16:359-363, discloses performing parallel, real-time, symmetric PCR amplification assays, each containing one of five, fluorescein-labeled, allele-specific molecular beacons which together span an 81-nucleotide long sequence of one strand of the rpoB gene core region of *M. tuberculosis* in overlapping fashion. Analysis was detection of probe fluorescence intensities after each PCR cycle. Failure of any one of the probes to hybridize to PCR-amplified target sequence ("amplicon") and emit its fluorescent signal was taken as an indication of drug resistance. El-Hajj et al. (2001) J. Clin. Microbiology 39:4131-4137, discloses performing a single, multiplex, real-time, symmetric PCR assay containing five differently colored, allele-specific molecular beacons, three complementary to one amplicon strand and two complementary to the other amplicon strand, which together span an 81-nucleotide long region of the rpoB gene core region of *M. tuberculosis* in overlapping fashion. Here again, probe fluorescence intensities were obtained, and failure of any one of the probes to hybridize and signal was taken as an indication of drug resistance. Wittwer et al. U.S. Pat. No. 6,140,054 discloses a multiplex symmetric PCR assay for detecting single and double base-pair mismatches in two sequences (C282Y and H63D sites) of the human HFE gene using a primer pair for each site, a FRET probe pair for each site, and rapid thermal cycling. Each probe pair includes a mismatch-tolerant fluorescein donor probe 20-30 nucleotides in length, positioned to hybridize to target sites of possible variations, and a Cy5 acceptor probe 35-45 nucleotides long, called the "anchor" probe, because it remains hybridized as its companion fluorescein probe melts off the target sequence at a melting temperature dependent on its degree of complementarity. The probe pair for one site, the C282Y site has a lower Tm range for wild type and mutant targets than does the probe pair for the H63D. Each probe pair has a higher melting Tm against its mutant target than against its wild type target As described by Witter, the melting temperature of at least one of the probes, typically the acceptor probe, is above the annealing temperature of both of the primers used in a symmetric PCR amplification, and the reaction kinetics are followed in real-time. Following amplification, a sample is analyzed by determining the Tm's of both probe pairs from the emissions of the acceptor (Cy5) probes. A target sequence having a single-nucleotide mismatch to its fluorescein-labeled donor probe, that is, a wild-type sequence, causes the donor probe to melt at a lower temperature, thereby lowering the melting temperature by about 5° C., revealing the presence of a mismatch. The genotype of a genome is established as either homozygous or heterozygous based on whether a signal is observed at one or two specific temperatures whose positions are anticipated in advance. Heterozygous genomes have equal concentrations of two possible alleles.

Analysis of nucleic acid sequences using multiple probes for long target sequences, whether a long single target sequence or multiple target sequences, by the foregoing methods is limited by the amount of information that can be obtained. In FRET-probe analysis, for every donor probe whose melting behavior is detected, there is a corresponding acceptor probe of high Tm that serves simply as an "anchor" and does not interrogate the target in a detectable fashion. Methods using molecular beacons, whether allele-specific or mismatch-tolerant, are limited by the number of fluorophore colors that can be distinguished in a single reaction mixture (maximally seven or eight for some detection instruments but only four colors for other instruments), and certain molecular-beacon methods are limited to relatively short target sequences. U.S. Pat. No. 7,385,043 discloses an assay intended to overcome the color limitation. It discloses a screening assay for one among as many as fifty or even seventy possible targets by having a probe specific to each target, specifically an allele-discriminating molecular beacon probe, subdividing each probe into multiple parts, and labeling each part with a different fluorophore, to create a multi-color code identifying each probe. Assays utilizing this approach are complicated and, thus, expensive, because the probes must have multiple fluorophores.

Sepsis exemplifies the need to analyze long nucleic acid target sequences. Analysis of sepsis is further complicated by the need to differentiate among numerous bacterial species, any of which could be the cause of infection. There is a need for single-tube screening assays for pathogenic infections such as sepsis, particularly assays that can be performed in laboratories other than high-complexity CLIA laboratories, that is, point-of-care diagnostic laboratories located at or near the site of patient care.

SUMMARY

In some embodiments, provided herein is a homogeneous assay method for analyzing at least one single-stranded nucleic acid target sequence in a sample, comprising: (a) providing a sample comprising at least one nucleic acid target sequence in single-stranded form and for each nucleic acid target sequence at least one detectably distinguishable set of two interacting hybridization probes, each of which hybridizes to the at least one target, comprising: (i) a quencher probe labeled with a non-fluorescent quencher, and (ii) a signaling probe that upon hybridization to the at least one target sequence in the sample in the absence of the quencher probe emits a signal above background, wherein, if both probes are hybridized to the at least one target sequence, the non-fluorescent quencher of the quencher probe quenches the signal from the signaling probe; and (b) analyzing hybridization of the signaling and quenching probes to the at least one target sequence as a function of temperature, the analysis including an effect on each signaling probe due to its associated quencher probe, including but not limited to analyzing signal increase, signal decrease, or both, from each signaling probe.

Another aspect provided herein is the foregoing method wherein the signaling probes include quenched fluorophores.

Another aspect provided herein is the foregoing method wherein the melting temperature of the signaling probe in a set is higher than the melting temperature of an associated quenching probe.

Another aspect provided herein is the foregoing method wherein quenching when both probes are hybridized to the target sequence is contact quenching.

Another aspect provided herein is the foregoing method wherein at least one nucleic acid target sequence comprises at least two target sequences, and wherein the probe set for each target sequence includes signaling probes that are detectably different from the signaling probes of every other probe set.

Another aspect provided herein is the foregoing method wherein providing the sample comprising at least one target sequence in single-stranded form comprises amplifying the nucleic acid target sequence(s), preferably by a LATE-PCR amplification method.

Another aspect provided herein is the use of the foregoing method in single-tube (e.g., tube, well, etc.) screening assays to identify which nucleic acid target sequence or sequences from a group of multiple possible target sequences is or are present in a sample, wherein the group of multiple target sequences comprises a variable sequence flanked by conserved, or at least relatively conserved sequences, and a sample of target sequence in single-stranded form is generated by an amplification method that generates single-stranded amplicons, for example, a non-symmetric polymerase chain reaction (PCR) method, most preferably LATE-PCR, using only a few pairs of primers, generally not more than three pairs, preferably not more than two pairs and more preferably only a single pair of primers, that hybridize to the flanking sequences, and wherein primers and at least one set of signaling and quencher probes, preferably at least two sets, are included in the amplification reaction mixture.

In some embodiments, probe sets (e.g. signaling and quencher probes) are configured to hybridize to the variable sequence and to differentiate between multiple target sequences (e.g. in a single sample or mixture). In some embodiments, probes hybridize with different Tm to the variable sequences of the different target sequences. In some embodiment, one or both probes of a probe set (e.g. signaling and/or quencher probes) comprise different degrees of complementarity to the variable regions of the different target sequences. In some embodiments, a signaling probe and/or quencher probe is configured to hybridize to the variable sequence (e.g. overlapping the actual sequence difference) of multiple target sequences (e.g. with different Tm to the different target sequences). In some embodiments, a signaling probe is configured to hybridize to the variable sequence of multiple target sequences (e.g. with different Tm to the different target sequences). In some embodiments, a quencher probe is configured to hybridize to the variable sequence of multiple target sequences (e.g. with different Tm to the different target sequences).

Another aspect provided herein is a reagent kit for use in any of the above methods comprising primers for amplifying each of the at least one nucleic acid target sequences and at least one probe set, and preferably including reagents for amplifying the nucleic acid target sequence or sequences.

Probing and analysis methods provided herein apply to samples containing single-stranded nucleic acid target sequences. Methods of this invention include analysis of a single sequence, analysis of two or more sequences in the same strand, analysis of sequences in different strands, and to combinations of the foregoing. A single-stranded nucleic acid target sequence may be a control sequence added to a sample. A nucleic acid target sequence may be DNA, RNA or a mixture of DNA and RNA. It may come from any source. For example, it may occur naturally, or the target sequence may occur in double-stranded form, in which case the single-stranded target sequence is obtained by strand separation and purification. If the single-stranded nucleic acid target sequence is a cDNA sequence, it is obtained from an RNA source by reverse transcription.

In many instances a natural source will not contain a target sequence in sufficient copy number for probing and analysis. In such instances the single-stranded target sequence is obtained by amplification, generally an amplification method that includes exponential amplification. Useful amplification methods include isothermal amplification methods and thermal cycling amplification methods. The amplification reaction may generate the single-stranded nucleic acid target sequence directly, or it may generate the target sequence in double-stranded form, in which event the single-stranded target sequence is obtained by strand separation and purification, as stated above. Useful amplification methods that may be employed include, the polymerase chain reaction (PCR), including symmetric PCR, asymmetric PCR and LATE-PCR, any of which can be combined with reverse transcription for amplifying RNA sequences, NASBA, SDA, TMA, and rolling circle amplification. If the single-stranded nucleic acid target sequence is a cDNA sequence, the amplification method will include reverse transcription, for example, RT-PCR. In some embodiments, when non-symmetric amplification is utilized, probe sets are included in the amplification reaction mixture prior to amplification to avoid contamination.

Probe sets useful in methods provided herein include a signaling probe and an associated quencher probe. The signaling probe is a hybridization probe that emits a detectable signal, preferably a fluorescent signal, when it hybridizes to a single-stranded nucleic acid target sequence in a sample, wherein the signal is quenchable by the associated quencher probe. The quencher probe does not emit visible light energy. Generally, a signaling probe has a covalently bound fluorescent moiety. Signaling probes include probes labeled with fluorophores or other fluorescent moieties, for example, quantum dots. In some embodiments, fluorophore-labeled probes are preferred. One type of signaling probe is a ResonSense® probe. A ResonSense® probe is a single-stranded oligonucleotide labeled with a fluorophore that accepts fluorescence from a DNA dye and reemits visible light at a longer wavelength. Use of a ResonSense® probe involves use of a double-stranded DNA dye, a molecule that becomes fluorescent when it associates with double-stranded DNA, which in this case is the hybrid formed when the probe hybridizes to the single-stranded nucleic acid target sequence. For use of a ResonSense® probe, a DNA dye, for example, SYBR Green or SYBR Gold, is included in the sample containing the single-stranded nucleic acid target sequence along with the probe set or sets. Analysis includes exciting the dye and detection emission from the ResonSense® probe or probes. Unbound signaling probes need not be removed, because they are not directly excited and remain single-stranded. In some embodiments, preferred signaling probes are quenched probes; that is, probes that emit little or no signal when in solution, even if stimulated, but are unquenched and so emit a signal when they hybridize to a single-stranded nucleic acid sequence in a sample being analyzed. Yin-yang probes are quenched signaling probes. A yin-yang probe is a double-stranded probe containing a fluorophore on one strand and an interacting non-fluorescent quencher on the other strand, which is a shorter strand. When a yin-yang probe is in solution at the detection temperature, the fluorophore is quenched. The single-stranded nucleic acid target sequence out-competes the quencher-labeled strand for binding to the fluorophore-labeled strand. Consequently, the fluorophore-labeled strand hybridizes to the single-stranded nucleic acid target sequence and signals. Especially preferred signaling probes for some embodiments provided herein are molecular beacon probes, single-stranded hairpin-forming oligonucleotides bearing a fluorescer, typically a fluorophore, on one end, and a quencher, typically a non-fluorescent chromophore, on the other end. When the probe is in solution, it assumes a closed conformation wherein the quencher interacts with the fluorescer, and the probe is dark. When the probe hybridizes to its target, however, it is forced into an open conformation in which the fluorescer is separated from the quencher, and the probe signals. FRET probe pairs do not meet the foregoing criteria and, thus, are not suitable for use in this invention, because their signaling probes, the acceptor probes, do not emit a detectable signal upon hybridization; rather, they emit a detectable signal only when both the donor-labeled probe and the acceptor-labeled probe.

In quenched signaling probes, quenching may be achieved by any mechanism, typically by FRET (Fluoresence Resonance Energy Transfer) between a fluorophore and a non-fluorescent quenching moiety or by contact quenching. In some embodiments, preferred signaling probes are dark or very nearly dark in solution to minimize background fluorescence. Contact quenching more generally achieves this objective, although FRET quenching is adequate with some fluorophore-quencher combinations and probe constructions.

The quencher probe of a probe set is or includes a nucleic acid strand that includes a non-fluorescent quencher. The quencher can be, for example, a non-fluorescent chromophore such a dabcyl or a Black Hole Quencher (Black Hole Quenchers, available from Biosearch Technologies, are a suite of quenchers, one or another of which is recommended by the manufacturer for use with a particular fluorophore). In some embodiments, preferred quenching probes include a non-fluorescent chromophore. In some embodiments, quenchers are Black Hole Quenchers. The quencher probe of a set hybridizes to the single-stranded nucleic acid target sequence adjacent to or near the signaling probe such that when both are hybridized, the quencher probe quenches, or renders dark, the signaling probe. Quenching may be by fluorescence resonance energy transfer (FRET or FET) or by touching ("collisional quenching" or "contact quenching").

FIG. 1 depicts a simple embodiment that illustrates the functioning of probe sets in analytical methods provided herein. In this embodiment there are two probe sets, probes 2, 4 and probes 6, 8. Probe 2 is a signaling probe, a molecular beacon probe bearing fluorophore 3. Probe 6 is also a signaling probe, a molecular beacon probe bearing fluorophore 7. Fluorophores 3, 7 are the same. Probes 4, 8 are quencher probes labeled only with Black Hole Quenchers 5 and 9, respectively. The melting temperatures (Tm's) of the probe-target hybrids (probes hybridized to single-stranded nucleic acid target sequence 1) are as follows: Tm probe 2>Tm probe 4>Tm probe 6>Tm probe 8. As the temperature of the sample is lowered from a high temperature at which no probes are bound, probes 2, 4, 6 and 8 bind to single-stranded nucleic acid target sequence 1 according to their hybridization characteristics. Probe 2, a signaling probe, binds first. FIG. 1, Panel A depicts probe 2 hybridized to sequence 1. As the temperature of the sample continues to be lowered, quencher probe 4 binds next, adjacent to probe 2 such that quencher 5 and fluorophore 3 are near to one another or touching. FIG. 1, Panel B depicts probe 4 hybridized to single-stranded nucleic acid sequence 1 adjacent to probe 2. At this point probe 2 is dark, or at least nearly dark. If, however, signaling probe 6 has begun to bind, it will emit fluorescence independently of probes 2, 4. FIG. 1, Panel C depicts probe 6 hybridized to single-stranded target sequence 1 adjacent to probe 4. Finally as the temperature continues to be lowered, probe 8 will bind, and its quencher 9 will quench fluorescence emission from fluorophore 7 of probe 6. FIG. 1, Panel D depicts probe 8 hybridized adjacent to probe 6. Analysis by hybridization is shown in FIG. 1, Panel E, which depicts the increase and decrease of fluorescence from fluorophores 3, 7 as a function of temperature. Such curves can be obtained as annealing (hybridization) curves as the temperature is lowered, or can be obtained as melting curves as the temperature is increased. As the sample temperature is lowered from 70° C., fluorescence curve 10 in Panel E first rises as probe 2 hybridizes to single-stranded nucleic acid sequence 1, then decreases as probe 4 binds, then increases again as probe 6 hybridizes, and finally decreases to a very low level as probe 8 hybridizes. One can deduce from curve 10 that each signaling probe has a higher Tm than its associated quencher probe.

Signaling and quenching probes useful in methods provided herein may be allele-specific (hybridize only to a perfectly complementary single-stranded nucleic acid target sequence in the method) or mismatch tolerant (hybridize to single-stranded nucleic acid target sequences containing one or more mismatched nucleotides, or deletions or additions). In some embodiments, one probe of a set may be allele-specific; and the other probe, mismatch tolerant. Experiments conducted during development of embodiments provided herein demonstrated that secondary structure of a target strand outside the sequences to which probes hybridize can affect the results of annealing or melting analysis. Accordingly, in some embodiments, not every nucleotide in a nucleic acid target sequence needs to be hybridized to a probe. For example, if the target sequence contains a hairpin, the corresponding probe can be designed in some cases to hybridize across the base of the hairpin, excluding the hairpin sequence. A probe set may include an allele-specific signaling probe and an allele-specific quencher probe, a mismatch-tolerant signaling probe and a mismatch-tolerant quencher probe, an allele-specific signaling probe and a mismatch-tolerant quencher probe, or a mismatch-tolerant signaling probe and an allele-specific quencher probe. A mismatch-tolerant probe may be perfectly complementary to one variant of a variable target sequence, or it may be a consensus probe that is not perfectly complementary to any variant. Multiple probe sets may include combinations of sets of any of the foregoing types. Additionally, analytical methods provided herein may utilize one or more signaling/quenching probe sets in combination with one or more conventional probes that signal upon hybridization to their target, for example, molecular beacon probes.

Probes useful in the methods provided herein may be DNA, RNA, or a combination of DNA and RNA. They may include non-natural nucleotides, for example, PNA, LNA, or 2' o-methyl ribonucleotides. They may include non-natural internucleotide linkages, for example, phosphorothioate linkages. The length of a particular probe depends upon its desired melting temperature (Tm), whether it is to be allele-specific or mismatch tolerant, and its composition, for example, the GC content of a DNA probe. Generally speaking, allele-specific probes are shorter than mismatch-tolerant probes. For example, an allele-specific DNA molecular beacon probe may have a target-hybridizing sequence, the loop, in the range of 10-25 nucleotides long, with a double-stranded stem 4-6 nucleotides long. Mismatch-tolerant DNA molecular beacon probe may have a somewhat longer loop, generally not more than 50 nucleotides in length, and a shorter double-stranded stem, preferably either one or two nucleotides long.

In some embodiments, each signaling probe has a separate quenching probe associated with it. In some embodiments, however one probe may be a part of two probe sets. For example, a quencher probe may be labeled with a quencher at each end, whereby the ends interact with different signaling probes, in which case three probes comprise two probe sets. Also, some embodiments may utilize both ends of a quenched signaling probe, for example, a molecular beacon signaling probe having a fluorophore on one end and a quencher on the other end. The fluorophore interacts with a quencher probe, comprising one set, and the quencher interacts with a signaling probe, comprising another set.

For analysis of a sample, the probe sets that are used are detectably distinguishable, for example by emission wavelength (color) or melting temperature (Tm). Making a probe set distinguishable by Tm from other probe sets can be accomplished in any suitable way. For example, all signaling probes in an assay may have different Tm's. Alternatively, all signaling probes could have the same Tm but the quencher probes could have different Tm's. Some fluorescence detectors can resolve up to eight differently colored fluorophores; others, only four. The same fluorescence emitter, for example, the same fluorophore, can be used on more than one signaling probe for a sample, if the signaling probe's can be differentiated for detection by their melting temperatures. In assays provided herein, Tm's should be separated by at least 2° C., preferably by at least 5° C. and, in certain embodiments by at least 10° C. Available temperature space constrains the use of multiple signaling probes having the same fluorophore. If an assay is designed for annealing and/or melt analysis over a range of 80° C. to 20° C., for example, one can utilize more probe sets sharing a color than one can use in an assay designed for such analysis over a range of 70° C. to 40° C., for which one may be able to use only 3-5 probe sets sharing a color. Using four colors and only two probe sets sharing each color, a four-color detector becomes equivalent to an eight-color detector used with eight probes distinguishable by color only. Use of three probe sets sharing each of four colors, twelve different probes sets become distinguishable.

It is generally preferred that quencher probes have lower Tm's than their associated signaling probes. With that relationship, the signaling probe emits a temperature-dependent signal through the annealing temperature range of both probes of the set as the temperature of the solution is lowered for an annealing curve analysis, and through the melting temperature range of both probes of the set as the temperature of the solution is raised for a melting curve analysis. If, on the other hand, the quencher probe of a probe set has a higher Tm than its associated signaling probe, the signaling probe's emission is quenched through the annealing temperature range and melting temperature range of both probes of the set, and no fluorescent signal is emitted for detection. This can be ascertained by examination of the annealing curve or the melting curve. The lack of signal provides less information about the single-stranded nucleic acid target sequence than does a curve of the probe's fluorescence as a function of temperature. In some embodiments, when mismatch-tolerant probes are used for analysis of a variable sequence, quencher probes with lower Tm's than their associated signaling probes are used with respect to all or all but one of the target sequence variants. If a quencher probe has a higher Tm against only one variant, signal failure will reveal that variant, as long as failure of the sample to include the single-stranded nucleic acid target sequence (particularly failure of an amplification reaction) is otherwise accounted for by a control or by another probe set for the single-stranded nucleic acid target sequence. Similarly, if not all variants are known, such signal failure will reveal the presence of an unknown variant. In some embodiments, it is preferred that in an assay utilizing multiple probe sets for at least one nucleic acid target sequence, the quencher probe of at least one probe set has a lower Tm than its associated signaling probe.

Melting temperature, Tm, means the temperature at which a nucleic acid hybrid, for example, a probe-target hybrid or primer-target hybrid, is 50% double-stranded and 50% single-stranded. For a particular assay the relevant Tm's may be measured. Tm's may also be calculated utilizing known techniques. In some embodiments, preferred techniques are based on the "nearest neighbor" method (Santa Lucia, J. (1998), PNAS (USA) 95: 1460-1465; and Allawi, H. T. and Santa Lucia, J. (1997), Biochem. 36: 10581-10594). Computer programs utilizing the "nearest neighbor" formula are available for use in calculating probe and primer Tm's against perfectly complementary target sequences and against mismatched target sequences. For examples in this specification, the program Visual OMP (DNA Software, Ann Arbor, Mich., USA) was used, which uses the nearest neighbor method, for calculation of Tm's. In this application the Tm of a primer or probe is sometimes given with respect to an identified sequence to which it hybridizes. However, if such a sequence is not given, for mismatch-tolerant probes that are perfectly complementary to one variant of a single-stranded nucleic acid target sequence, the Tm is the Tm against the perfectly complementary variant. In many embodiments there will be a target sequence that is perfectly complementary to the probe. However, methods may utilize one or more mismatch-tolerant primer or probes that are "consensus primers" or "consensus probes." A consensus primer or probe is a primer or probe that is not complementary to any variant target sequence or, if not all possible target sequences are known, to any expected or known sequence. A consensus primer is useful to prime multiple variants of a target sequence at a chosen amplification annealing temperature. A consensus probe is useful to shrink the temperature space needed for analysis of multiple variants. For a consensus primer or probe, if no corresponding target sequence is given, the Tm refers to the highest Tm against known variants, which allows for the possibility that an unknown variant may be more complementary to the primer or probe and, thus, have higher primer-target Tm or probe-target Tm.

Assays provided herein may utilize probe concentrations that are greater than or less than target nucleic acid concentration. The probe concentrations are known on the basis of information provided by the probe manufacturer. In the case of target sequences that are not amplified, target concentrations are known on the basis of direct or indirect counting of the number of cells, nuclei, chromosomes, or molecules are known to be present in the sample, as well as by knowing the expected number of targets sequences usually present per cell, nucleus, chromosome, or molecule. In the case of target sequences that are amplified, there are a number of ways to establish how many copies of a target sequence have been generated over the course of an amplification reaction. For example, in the case of a LATE-PCR amplification reaction the number of single-stranded amplicons can be calculated as follows: using a signaling probe without a quencher (in the case of quenched signaling probe that means the probe minus the quencher) in a limiting concentration such as 50 nM and its corresponding quencher probe in excess amount such as 150 nM, the number of cycles it takes to decrease the fluorescence to zero (or, in practical terms, to its minimal background level) is proportional to the rate of amplification of single-stranded amplicons. When fluorescence reaches zero (minimal background level), all of the signaling probes have found their target, and the concentration of the amplicons exceeds that of the signaling probe. Another method for estimating amplicon concentration in a LATE-PCR amplification is presented in Example 10 of published patent application EP 1805199 A2. In certain embodiments an amplification reaction may be continued until the amplicon being produced reaches a "terminal concentration." Experiments conducted during development of embodiments provided herein demonstrated that a LATE-PCR amplification begun with differing amounts of target tends to produce eventually the same maximum concentration of amplicon (the "terminal concentration"), even though amplification begun with a high starting amount of target reaches that maximum in fewer cycles than does the amplification begun with a low starting amount of target. To achieve the terminal concentration beginning with a low amount of target may require extending the amplification through 70 or even 80 cycles.

Some embodiments utilize probe sets in which the concentration of the signaling probe is lower than the concentration of its associated quencher probe. This ensures that, when both probes are hybridized to their at least one nuclei acid target sequence, the signaling probe is quenched to the greatest possible degree, thereby minimizing background fluorescence. It will be appreciated that background fluorescence in an assay is the cumulated background of each signaling probe of a given color and that probes of a different color may contribute further to background signal.

Methods provided herein include analyzing the hybridization of probe sets to the single-stranded nucleic acid target sequences. In methods provided herein, hybridization of signaling probes and quencher probes as a function of temperature is analyzed for the purpose of identifying, characterizing or otherwise analyzing at least one nucleic acid target sequence in a sample. In some embodiments analysis includes obtaining a curve or, if multiple colors are used, curves of signals from signaling probes as the temperature of a sample is lowered (see FIG. 1, Panel E) or obtaining a curve or curves of signals as the sample temperature is raised, or both. It is known that the shapes of the two types of curves are not necessarily identical due to secondary structures. Either or both of those curves can be compared to a previously established curve for a known single-stranded nucleic acid target sequence as part of the analysis, for example, identifying the single-stranded nucleic acid target sequence being probed. Derivative curves can also be utilized to obtain, for example, the Tm of a signaling probe against a nucleic acid target sequence. It is not always necessary, and it may not be desirable, to utilize entire fluorescence curves or their derivatives. In certain embodiments analysis of the hybridization of signaling probes and quencher probes includes obtaining fluorescence readings at one or several temperatures as the sample temperature is lowered or raised, where those readings reflect an effect on each signaling probe due to its associated quencher probe. For example, if it is desired to distinguish among known variants of a target sequence, and one learns from hybridization curves of variants that fluorescence at two temperatures distinguish the variants, one need acquire fluorescence at only those two temperatures for either direct comparison or for calculation of ratios that can be compared. In most embodiments the analysis will include signal increase, signal decrease, or both, from each signaling probe.

In analytical methods provided herein, provision of an at least one nucleic acid target sequence may include nucleic acid amplification. Some preferred methods are those which generate the target sequence or sequences in single-stranded form. LATE-PCR amplification of DNA sequences or RNA sequences (RT-LATE-PCR) is especially preferred in some embodiments. LATE-PCR amplifications and amplification assays are described in, for example, European patent EP 1,468,114 and corresponding U.S. Pat. No. 7,198,897; published European patent application EP 1805199 A2; Sanchez et al. (2004) Proc. Nat. Acad. Sci. (USA) 101: 1933-1938; and Pierce et al. (2005) Proc. Natl. Acad. Sci. (USA) 102: 8609-8614. All of these references are hereby incorporated by reference in their entireties. LATE-PCR is a non-symmetric DNA amplification method employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon. After the Limiting Primer is exhausted, amplification continues for a desired number of cycles to produce single-stranded product using only the Excess Primer, referred to herein as the Excess Primer strand. LATE-PCR takes into account the concentration-adjusted melting temperature of the Limiting Primer at the start of amplification, $Tm_{[0]}^L$, the concentration-adjusted melting temperature of the Excess Primer at the start of amplification, $Tm_{[0]}^X$, and the melting temperature of the single-stranded amplification product ("amplicon"), $Tm_A$. For LATE-PCR primers, $Tm_{[0]}$ can be determined empirically, as is necessary when non-natural nucleotides are used, or calculated according to the "nearest neighbor" method (Santa Lucia, J. (1998), PNAS (USA) 95: 1460-1465; and Allawi, H. T. and Santa Lucia, J. (1997), Biochem. 36: 10581-10594) using a salt concentration adjustment, which in our amplifications is generally 0.07 M monovalent cation concentration. For LATE-PCR the melting temperature of the amplicon is calculated utilizing the formula: Tm=81.5+0.41 (% G+% C)−500/L+16.6 log [M]/(1+0.7 [M]), where L is the length in nucleotides and [M] is the molar concentration of monovalent cations. Melting temperatures of linear, or random-coil, probes can be calculated as for primers. Melting temperatures of structured probes, for example molecular beacon probes, can be determined empirically or can be approximated as the Tm of the portion (the loop or the loop plus a portion of the stem) that hybridizes to the amplicon. In a LATE-PCR amplification reaction $Tm_{[0]}^L$ is preferably not more than 5° C. below $Tm_{[0]}^X$, more preferably at least as high and even more preferably 3-10° C. higher, and $Tm_A$ is preferably not more than 25° C. higher than $Tm_{[0]}^X$, and for some preferred embodiments preferably not more than about 18° C. higher.

LATE-PCR is a non-symmetric PCR amplification that, among other advantages, provides a large "temperature space" in which actions may be taken. See WO 03/054233 and Sanchez et al. (2004), cited above. Certain embodiments of LATE-PCR amplifications include the use of hybridization probes, in this case sets of signaling and quencher probes, whose Tm's are below, more preferably at least 5° C. below, the mean primer annealing temperature during exponential amplification after the first few cycles. Sets of signaling and quencher probes are included in LATE-PCR amplification mixtures prior to the start of amplification. A DNA dye, if used, can also be incorporated into the reaction mixture prior to the start of amplification.

Amplification and detection methods provided herein enable single-tube, homogeneous assays to detect variants of a particular variable sequence, for example, a ribosomal RNA sequence, whose variants are found in a group of organisms, including but not limited to bacteria, fungi, protozoa, humans and other animals, green plants, and blue green algae, where the particular variable sequence is flanked by sequences that are conserved, or relatively conserved, among members of the group. Variants of the variable sequence can then be amplified by a primer-dependent amplification method, preferably an amplification method that generates single-stranded nucleic acid target sequences, such as a non-symmetric polymerase chain reaction (PCR) DNA amplification method, most preferably LATE-PCR (with reverse transcription, if the variants are RNA), using only a few pairs, sometimes only a single pair, of primers that hybridize to the flanking sequences. Sets of signaling probes and quencher probes are included in the amplification reaction mixture, and the amplification product or products are analyzed by the analytical methods provided herein.

In some embodiments, provided herein are kits comprising combinations of signaling and quencher probes, which may be referred to as "oligonucleotide sets," for use in the foregoing methods, as well as kits that additionally include some or all of primers, amplification reagents, such as amplification buffer, DNA polymerase and, where appropriate, reverse transcriptase. Kits may also include control reagents (e.g., positive and negative controls) or any other components that are useful, necessary, or sufficient for practicing any of the methods described herein, as well as instructions, analysis software (e.g., that facilitates data collection, analysis, display, and reporting), computing devices, instruments, or other systems or components.

Provided herein are amplification reaction mixtures for performing amplification assay methods of this invention. Such reaction mixtures include reagents for providing single-stranded nucleic acid target sequence or sequences to be analyzed, and sets of signaling and quencher probes for the analysis. Some reaction mixtures include reagents for non-symmetric amplification, most preferably LATE-PCR and RT-LATE-PCR amplification.

BRIEF DESCRIPTION OF THE DRAWINGS

FIG. 1, Panel E, shows the fluorescence versus temperature of the sample.

FIG. 12 is a schematic representation of a selected region of the 16s gene of several species of bacteria showing binding locations of the primer pair and of four sets of signaling and quencher probes used in Example 5.

FIG. 16 is a schematic representation of a selected region of the 16s gene of *Acinetobacter baumanii* showing binding locations of the primer pair and four sets of signaling and quencher probes used in Example 7.

DETAILED DESCRIPTION

Figure 1:
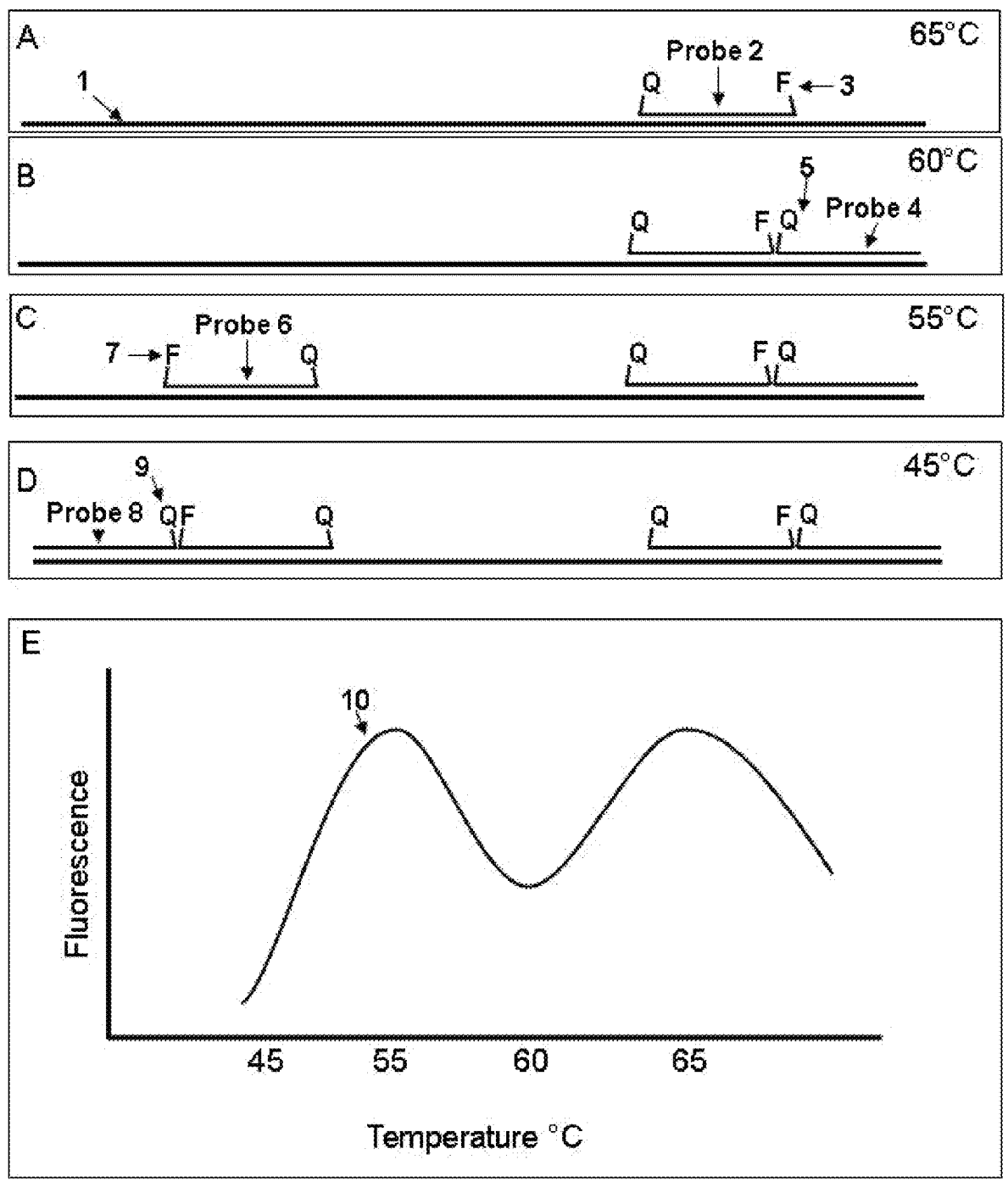
FIG. 1, Panels A-D are schematics showing hybridization of two sets of signaling and quencher probes to a single-stranded nucleic acid target sequence in a sample as a function of temperature.

In some embodiments, useful signaling probes are hybridization probes that emit a detectable signal above background when they hybridize to a target sequence. Some preferred signaling probes are quenched probes, that is, probes whose fluorescence is quenched when the probes are in solution. In some embodiments, signaling probes are molecular beacon probes, which are single-stranded oligonucleotides that have a covalently bound signaling fluorophore one end and a quencher moiety, for example another fluorophore, preferably a non-fluorescent quencher, for example Dabcyl or a Black Hole Quencher, on the other end. Molecular beacon probes have a central target-complementary sequence flanked by arm sequences that hybridize to one another in the absence of the target sequence, causing the probe to adopt a stem-loop conformation in which the quenching moiety quenches fluorescence from the signaling fluorophore by fluorescence resonance energy transfer (FRET) or by collisional (or contact) quenching. Molecular beacon probes have low background fluorescence due to efficient quenching in the stem-loop structure. When the target-complementary sequence, that is, the loop or the loop plus some or all of the stem nucleotides, hybridizes to a target sequence, the arm sequences are separated from one another, and the probe's quenching moiety no longer quenches fluorescence from the signaling fluorophore. See Tyagi and Kramer (1996) Nature Biotechnology 14: 303-308; and El-Hajj et al. (2001) J. Clin. Microbiology 39: 4131-4137. Other types of oligonucleotide hybridization probes that emit a detectable fluorescent signal upon hybridization may also be used. Such include, for example, single-stranded linear probes labeled at opposite ends with a signaling fluorophore and a quencher fluorophore. (see, Livak et al. (1995) PCR Methods Appl. 357-362); double-stranded oligonucleotide probes having a signaling fluorophore on one strand and a quenching moiety on the other strand (see Li et al. (2002) Nucl. Acid. Res. 30(2)e5); and ResonSense® probes, linear single-stranded probes labeled with a signaling fluorophore that emits energy received by FRET from a DNA dye such as SYBR Green that associates with the probe-target hybrid (see U.S patent publication US 2002/0119450).

Quencher probes may be structurally similar to signaling probes but without a signaling fluorophore, that is, with just a quencher moiety. Because quencher probes do not contribute background fluorescence, they can be linear probes. For a quencher probe to be "associated" with a signaling probe, that is, to be able to quench that signaling probe when both are hybridized to the single-stranded nucleic acid target sequence being analyzed, the signaling fluorophore of the signaling probe is located at or near the end nearest the quencher probe, and the quenching moiety of the quencher probe is located at or near the end of the quencher probe, such that that fluorophore and that quenching moiety can interact by FRET or by contact quenching. In some embodiments, quenching moieties for quencher probes are non-fluorescent chromophores such as Dabcyl and Black Hole Quenchers.

Signaling probes and quenching probes may be either sequence-specific or mismatch tolerant. A sequence-specific probe hybridizes in the assay only to a target sequence that is perfectly complementary to the probe. A mismatch-tolerant probe hybridizes in the assay, not only to a target sequence that is perfectly complementary to the probe, but also to variations of the target sequence that contain one or more mismatches due to substitutions, additions or deletions. For mismatch-tolerant probes, the greater the variation of the target from perfect complementarity, the lower the Tm of the probe-target hybrid. Combinations of sequence-specific and mismatch-tolerant probes may be used in a single assay. If a probe is sequence-specific, any mismatch in the target sequence will cause the probe not to hybridize, and its lack of hybridization will show in the melt curve and the derivative curve. For example, if a signaling probe hybridizes, causing an increase in fluorescence, but its associated quencher probe does not hybridize, fluorescence will not decrease as the temperature is lowered through the Tm of the quencher probe, revealing that the quencher probe did not hybridize and indicating a target mutation in the sequence complementary to the quencher probe. That is a satisfactory result, if one wishes to determine whether or not there is any mutation. That is not satisfactory, however, if one wishes to determine which one of several possible mutations of that sequence is present. For that, it is preferable that the associated quencher probe be mismatch tolerant, so that different mutations can be distinguished by their different effects on the melting curve (and derivative curve) due to differing Tm effects of different mutations.

In some preferred embodiments, a signaling probe of a set has a higher Tm with respect to the single-stranded nucleic acid target sequence than does its associated quencher probe. With that relationship, as a sample is subjected to melt analysis, for example, as temperature is increased signal first increases as the quencher probe melts off and then decreases as the signaling probe melts off. With the opposite relationship, signal remains quenched as the lower Tm signaling probe melts off and does not then increase as the higher Tm quencher probe melts off. The preferred relationship thus provides more information. In some embodiments, it is preferred that the quencher probe of a set reduces the signal from its associated signaling probe to a very large extent. In such embodiments, it is preferred that the concentration of the quencher probe equal or exceed the concentration of the signaling probe. In order to maximize signal amplitude, certain embodiments utilize probe concentrations that are in excess with respect to the single-stranded nucleic acid target sequence, thereby ensuring that all or nearly all copies of the target sequence will have hybridized probes.

Methods provided herein include the use of a single set of interacting signaling and quencher probes. Methods also include the use multiple sets of interacting signaling and quencher probes, wherein each signaling probe is detectably distinguishable from the others. Distinction of fluorescent probes may be by color (emission wavelength), by Tm, or by a combination of color and Tm. Multiple sets of interacting probes may be used to interrogate a single target sequence or multiple target sequences in a sample, including multiple target sequences on the same target strand or multiple target sequences on different strands. Multiplex detection of multiple target sequences may utilize, for example, one or more sets of signaling/quencher probes specific to each target sequence. In some embodiments, multiplex methods utilize a different fluorescent color for each target sequence. Certain embodiments utilize the same color for two different target sequences, available temperature space permitting.

In some embodiments, methods comprise analyzing hybridization of signaling/quencher probe sets to one or more single-stranded nucleic acid target sequences as a function of temperature. Signal, preferably fluorescent signal, from the signaling probe or probes may be acquired as the temperature of a sample is decreased (annealing) or increased (melting). Analysis may include acquisition of a complete annealing or melting curve, including both increasing and decreasing signals from each signaling probe, as is illustrated in FIG. 1, Panel E. Alternatively, analysis can be based only on signal increase or signal decrease. Analysis may utilize only signals at select temperatures rather than at all temperatures pertinent to annealing or melting. Analysis at some or all temperatures may be digitized to create a signature for a target sequence, for example, a bar code such as described in Example 4 and shown in FIG. 11. Analysis may include comparison of the hybridization of an unknown single-stranded nucleic acid target sequence to hybridization of known target sequences that have been previously established, for example, a compilation of melting curves for known species or a table of digitized data for known species.

In methods provided herein, one or more single-stranded nucleic acid target sequences to be analyzed may be provided by nucleic acid amplification, generally exponential amplification. Any suitable nucleic amplification method may be used. Preferred amplification methods are those that generate amplified product (amplicon) in single-stranded form so that removal of complementary strands from the single-stranded target sequences to be analyzed is not required. Probe sets may be included in such amplification reaction mixtures prior to the start of amplification so that reaction vessels containing amplified product need not be opened. When amplification proceeds in the presence of probe sets, it is preferred that the system be designed such that the probes do not interfere with amplification. In some embodiments a non-symmetric PCR method such as asymmetric PCR or, LATE-PCR is utilized to generate single-stranded copies. PCR amplification may be combined with reverse transcription to generate amplicons from RNA targets. For example, reverse transcription may be combined with LATE-PCR to generate DNA amplicons corresponding to RNA targets or the complements of RNA targets. In some embodiments, amplification methods that generate only double-stranded amplicons are not preferred, because isolation of target sequences in single-stranded form is required, and melt-curve analysis is more difficult with double-stranded amplicons due to the tendency of the two amplicons to collapse and eject hybridization probes. In some embodiments, methods provided herein do not utilize generation of detectable signal by digestion of signaling probes, such as occurs in 5' nuclease amplification assays. In a PCR amplification reaction, for example, avoidance of probe digestion may be accomplished either by using probes whose Tm's are below the primer-extension temperature, by using probes such as those comprising 2' O-methyl ribonucleotides that resist degradation by DNA polymerases, or by using DNA polymerases that lack 5' exonuclease activity. Avoidance of probe interference with amplification reactions is accomplished by utilizing probes whose Tm's are below the primer-extension temperature such that the probes are melted off their complementary sequences during primer extension and, most preferably, during primer annealing, at least primer annealing after the first few cycles of amplification. For example, in the amplification assay method of Example 1, the LATE-PCR amplification method utilized two-step PCR with a primer-annealing/primer-extension temperature of 75° C. in the presence of a set of mismatch-tolerant molecular beacon probes having Tm's against the wild-type target sequence (to which the probes were perfectly complementary) ranging from 75° C. to 50° C., which ensured that none of the probes interfered significantly with amplification of the target sequence.

In LATE-PCR amplification, for example, the Excess Primer strand is the single-stranded amplicon to which probe sets hybridize. It therefore is or contains the single-stranded nucleic acid sequence that is analyzed. Its 5' end is the Excess Primer, and its 3' end is the complement of the Limiting Primer. If the sequence to be analyzed lies between the Excess Primer and the Limiting Primer, the starting sequence that is amplified and the Excess Primer strand both contain that sequence. If in the starting sequence to be amplified the sequence desired to be analyzed includes a portion of either priming region, it is required that the primer be perfectly complementary to that portion so that the Excess Primer strand contain the desired sequence. Primers need not be perfectly complementary to other portions of the priming regions. Certain embodiments of methods provide single-stranded nucleic acid target sequence to be analyzed by amplification reactions that utilize "consensus primers' that are not perfectly complementary to the starting sequence to be amplified, and care is taken to ensure that the Excess Primer strand, which is or contains the single-stranded target sequence that is actually analyzed, contains the desired sequence.

Features and embodiments of methods provided herein are illustrated in the Examples set forth below in conjunction with the accompanying Figures. All of the Examples illustrate providing as the single-stranded target sequence or sequences to be analyzed the Excess Primer strand of a LATE-PCR amplification. Probe sets in the Examples are designed for contact quenching of signaling probes by quencher probes.

Figure 2:
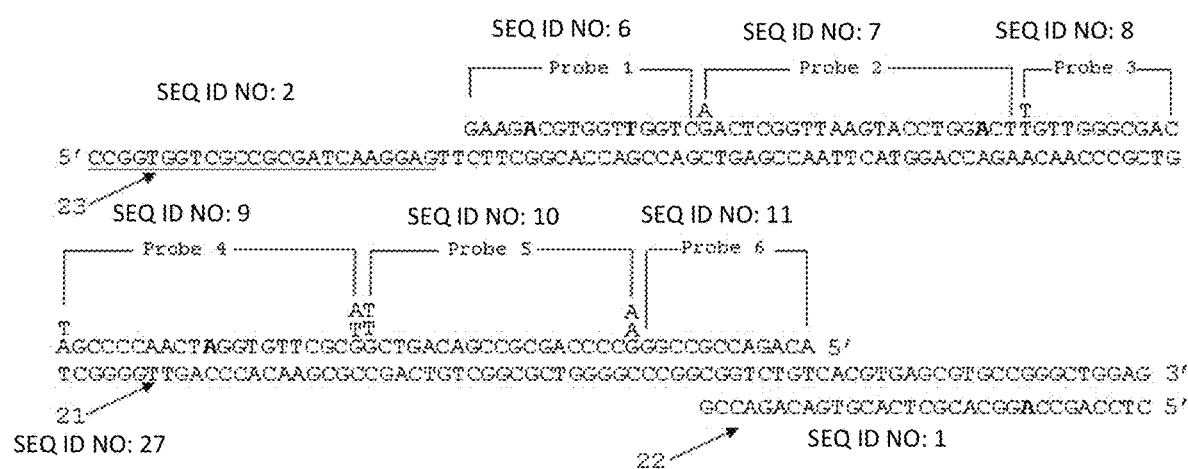
FIG. 2 is a schematic representation of a single-stranded nucleic acid sequence from Example 1 showing probe binding locations and primer binding locations.
Figure 3A:
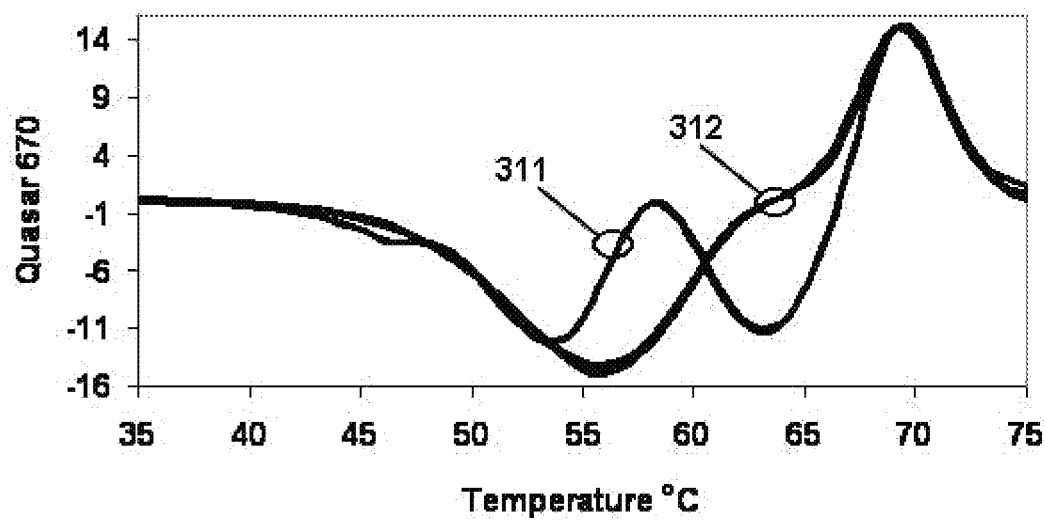
FIGS. 3A and 3B present melt-curve analyses from amplifications described in Example 1 for several strains.
Figure 3B:
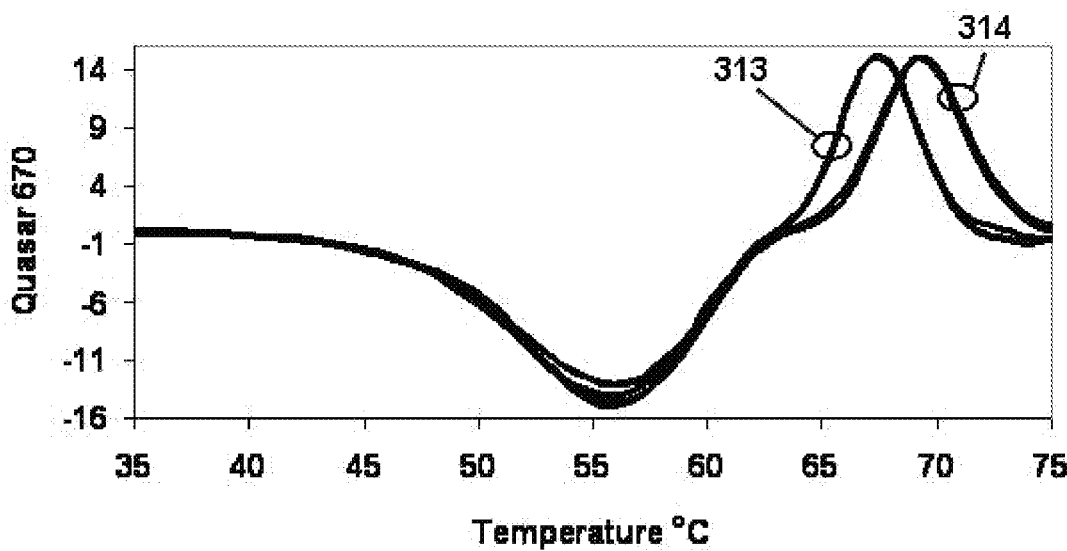

Example 1 is a case in which a priming region of the pre-amplification target sequence is included in the sequence desired to be analyzed. As shown in FIG. 2, eight nucleotides complementary to the Limiting Primer are included in the sequence that is to be probed. Example 1 also illustrates the use of a primer that contains a mismatch. In this case the mismatch lies outside of the eight nucleotides included in the sequence to be probed, and the sequence of the Excess Primer strand that is analyzed is identical to the pre-amplification target sequence 21. Example 1 illustrates the use of multiple probe sets (three signaling probes and three quencher probes) to interrogate one target sequence (a 101-nucleotide long sequence of the rpoB gene of *mycobacterium tuberculosis*). The spread of the probes across the target sequence is shown schematically in FIG. 2. Example 1 illustrates the use of multiple signaling probes of the same color (all include the fluorophore Quasar 670). Signaling probes 2, 4 and 5 hybridize to different portions of the target sequence and have different calculated Tm's relative to the wild-type target sequence—63° C., 67° C. and 75° C., respectively. In Example 1 each signaling probe has its own is associated quencher probe that hybridizes proximate to it, that is, sufficiently close that its quencher moiety can quench the signaling probe's fluorophore moiety. Quencher probes 3, 5 and 6 are associated with signaling probes 2, 4 and 5, respectively. Example 1 illustrates the use of signaling probes that have Tm's higher than their respective quencher probes. Quencher probes 3, 5 and 6 have Tm's relative to the wild-type target sequence of 50° C., 56° C. and 63° C., respectively, such that each quencher probe melted off the target sequence before its associated signaling probe. The two probe sets are not distinguishable by color, but they are distinguishable be Tm. Example 1 further illustrates the use of a signaling probe (Probe 2) and a quencher probe (Probe 3) that each has a terminal nucleotide complementary to the same nucleotide of the single-stranded nucleic acid target sequence. All six probes were mismatch-tolerant. The signaling probes and the quencher probes in this case hybridized adjacently and so covered every nucleotide of the target sequence that was analyzed. Example 1 illustrates the use of quenched signaling probes, as each of signaling probes 2, 4 and 5 is a molecular beacon probe with a stem two nucleotides in length. The example illustrates the use of a quencher probe that has a hairpin structure (Probe 1) and quencher probes that are linear probes (Probe 3 and Probe 6). The three probe sets were tested against a drug-sensitive strain and against two different drug-resistant strains. Analysis of hybridization of the six probes against the Excess Primer strand from amplification of the three strains was by melting. FIGS. 3A-3B present curves showing the first derivative of fluorescence readings (derivative of the melt curves). As can be seen from FIGS. 3A-3B, the curve for each drug-resistant strain differed from the curve for the drug-sensitive strain and from one another. Thus, the set of probes was able to determine whether the sample contained the drug-sensitive sequence or either drug-resistant sequence. Because each drug-resistant strain had a curve that was distinguishably different, the set of six probes was able to determine which drug-resistant strain was present in a sample. The three curves obtained from these three known sequences could be utilized as a library against which to compare curves from samples containing unknown strains.

Figure 4A:
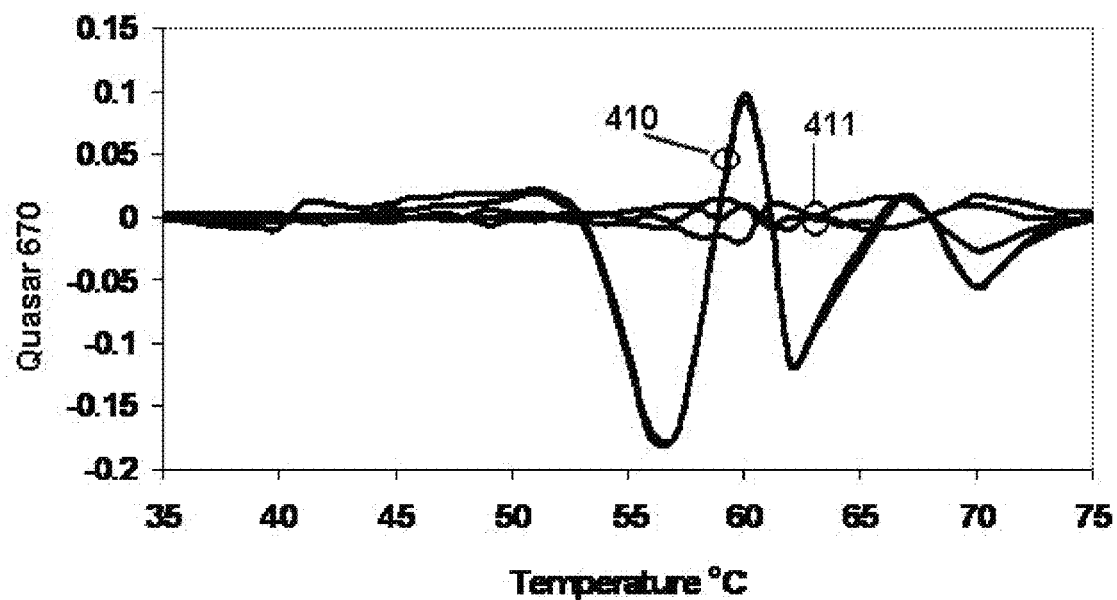
FIGS. 4A-4D presents derivative melting curves for mixtures of TB strains in various proportions as described in Example 2.
Figure 4B:
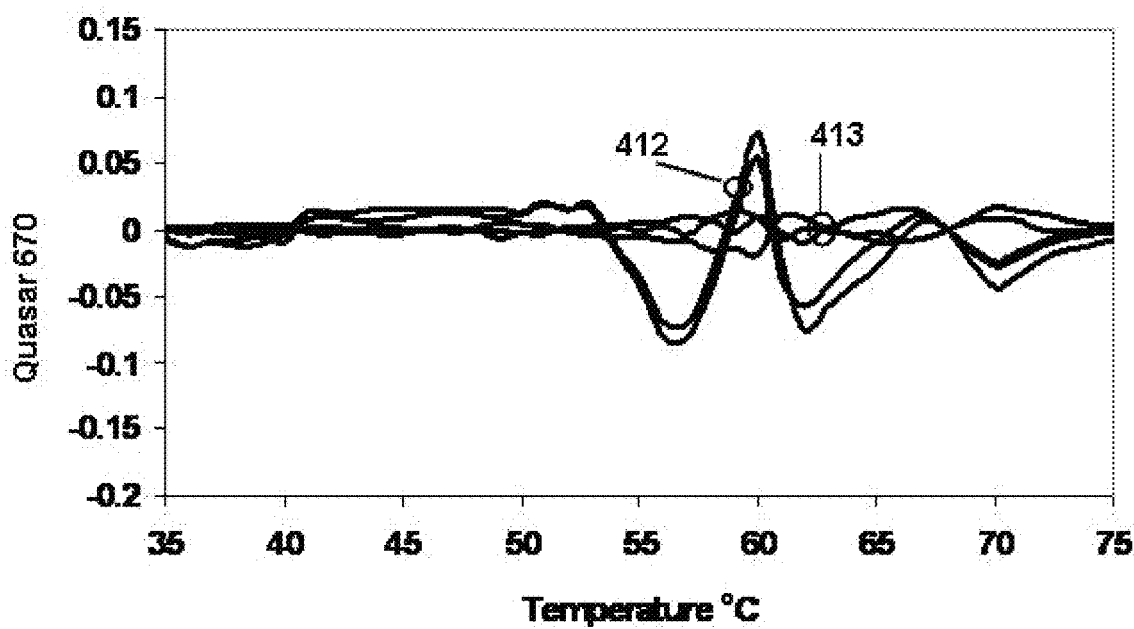

Example 2 illustrates use of a method provided herein to analyze a mixture of two starting targets, in this case two variants of a sequence amplified by a single primer pair. Using starting targets from Example 1 (the drug-sensitive strain and one drug-resistant strain), along with the primers and six probes from Example 1, mixtures of the two strains in proportions varying from 20% to 1% of the drug-resistant strain were amplified by LATE-PCR to generate mixtures of two different Excess Primer strands in varying proportions. As shown in FIGS. 4A-4B, the assay is able to determine the proportion of drug-resistant strain in the mixtures. Example 2 also illustrates the use of fluorescence data acquisition from a melt subsequent to the first melt (in this case the averages of second, third and fourth melts were used). Experiments conducted during development of embodiments provided herein demonstrated that, in some embodiments, the second melt curve differs somewhat from the first, and that subsequent melt curves agree with the second. It is contemplated that in some embodiments this is due to secondary structure that is altered during the first melt, although the embodiments provided herein are not limited to any particular mechanism of action and an understanding of the mechanism of action is not necessary to practice the embodiments. To accommodate the effect, however, hybridization data, either annealing data or melting data, can be acquired after an initial melt, which can be a rapid melt.

Figure 5:
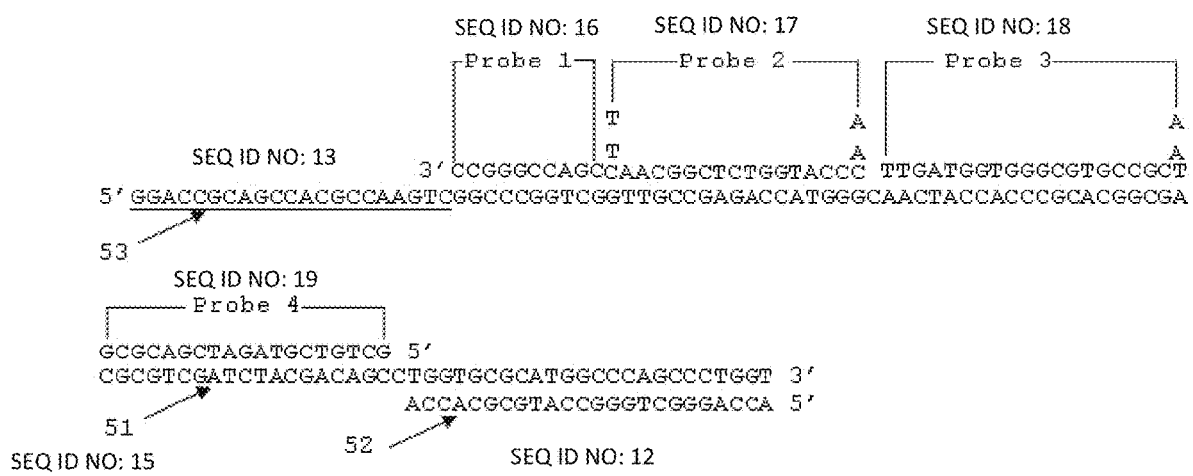
FIG. 5 is a schematic representation of a single-stranded nucleic acid sequence from Example 3 showing probe binding locations and primer binding locations.

Example 3 illustrates an embodiment that includes analysis of three different variant sequences in the same sample using at least one probe set for each sequence, wherein probe sets for the three sequences are detectably distinguishable by color and wherein different probe sets for one sequence are detectably distinguishable by Tm. Each variant sequence to be analyzed is provided by LATE-PCR amplification using an Excess Primer and a Limiting Primer, and a different primer pair is used for each of the three variant sequences. As shown in FIG. 5, Example 3 illustrates: the use of one probe (Probe 3) a part of two probe sets; the use of a probe (quencher Probe 1) that is not part of any probe set; and probes that hybridize to the single-stranded nucleic acid target sequence with a gap of one nucleotide between them (Probe 2 and Probe 3). Probe 2 and Probe 3 are both molecular beacon probes with a stem two nucleotides long, but whereas none of the stem nucleotides of Probe 2 is complementary to the target sequence, two stem nucleotides of Probe 3 are complementary to the target sequence.

Figure 8:
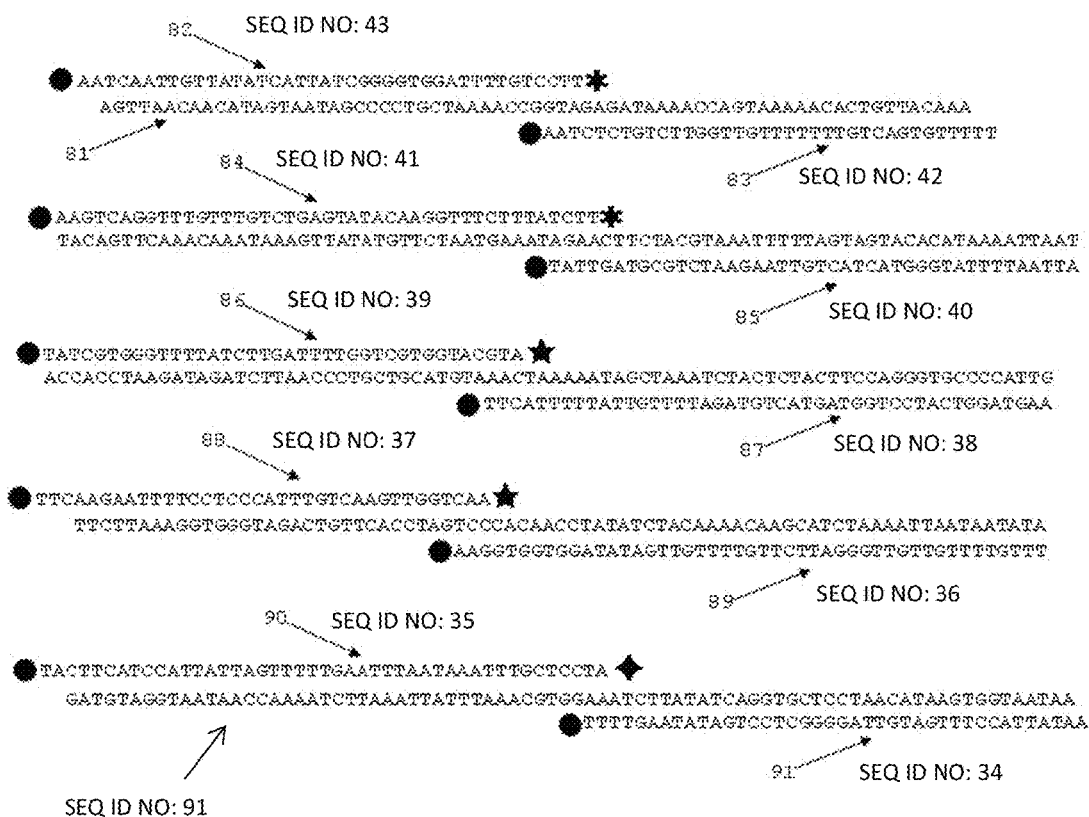
FIG. 8 is a schematic representation of a single-stranded nucleic acid sequence from Example 4 showing probe binding locations and primer binding locations.

FIGS. 8-11, which accompany Example 4, illustrate the flexibility of methods provided herein for analyzing sets of signaling probes and quencher probes that are detectably distinguishable by either melt or anneal analysis in combination with color. The selected target sequence is a 500 base-pair portion of the mitochondrial cytochrome c oxidase subunit 1 gene (cox 1), which overlaps a sequence that has been used as an identifier of numerous species by sequencing (Herber, P D (2003) Proc. Bol. Sci. 270 Suppl. 1:S96-9). Sequences of that gene for 264 different species of nematodes were aligned and used to identify the selected portion, an area that contained high-variability sequences flanked by conserved sequences. In these conserved regions three consensus LATE-PCR Limiting Primers and a single Excess Primer were designed. The three consensus Limiting Primers provided sufficient complementarity to allow amplification of all 264 species above 50° C. The design procedure for all probes was a consensus sequence that would hybridize to all 264 variants at temperatures within the range of 30-60° C. The logic of this approach applies equally to other lengthy variable sequences, for example, sequences within chloroplasts of plant cells and sequences of bacteria such as ribosomal genes. FIG. 8 shows the Excess Primer strand containing a sequence complementary to Limiting Primer Two for the variant *Caenorhabditis elegans* with all ten probes hybridized. Mismatches between each probe and this variant are identified in Example 4.

Example 4 illustrates the use of an annealing curve to analyze the probes' hybridization for each color used. FIGS. 9A-9C and FIGS. 10A-10C present annealing curves for the three fluorophores for two species, including *C. elegans*. Analysis may include preparation of a reference file of the annealing curves for all 260 species, and manual comparison of the curves from an unknown sample with the curves in the reference file. Experiments were performed during development of embodiments provided herein to develop a procedure for digitization of the curves to permit comparison by computer. FIGS. 11A-11C present the digitized results in graphical, bar code, form, which can be used for manual comparison to a reference bar-code file. Example 5 discloses an embodiment of a screening assay, in this case a sepsis screening assay. Example 5 illustrates several features and embodiments provided herein. It illustrates probing and analysis of a variable sequence to determine which variant is present from among numerous possible variants. It illustrates the use of multiple sets of signaling and quencher probes wherein, further, the signaling probes have the same fluorophore and emit the same color. It illustrates (Table 3) not only the use of signaling probes whose melting temperatures are higher against all possible target sequences than their associated quencher probes, but also inclusion of a set of a signaling probe and quencher probe where the opposite is the case for one or more possible target sequences (probes Quasar 1 On and Quasar 1 Off). It further illustrates the use of multiple probe sets wherein certain individual probes, signaling or quencher, need not hybridize to every possible target sequence in the temperature range of detection, here 80° C. to 25° C. (see Table 3).

Example 5 illustrates analyzing hybridization of signaling and quencher probes, including the effect of hybridization of quencher probes on fluorescence emission signals from the signaling probes, as a function of temperature utilizing annealing curves (FIG. 13) and derivative curves (FIG. 14), either or both of which can be maintained as a library against which to compare curves from unknown samples, and using digitized information derived from such curves (Table 4), which also can be maintained as a library.

Example 5 illustrates the use of nucleic acid amplification to provide a sample, or reaction mixture, containing a target sequence in single-stranded form, in this case a non-symmetric amplification method that generates a single-stranded amplicon, the target sequence to be analyzed. Example 5 further illustrates amplification using a single pair of primers that hybridize to conserved sequences flanking a variable sequence so as to generate a target sequence from whichever variant of the variable sequence is present. It will be appreciated that, as indicated earlier, a method such as Example 5 or a method such as Example 4 can begin with a sample containing RNA and include reverse transcription prior to amplification. Example 5 also illustrates not only homogeneous detection in which bound signaling probes do not have to be separated from unbound signaling probes prior to detection, but also a "single-tube" method in which amplification and detection are performed without the need to open the reaction container following amplification. The signaling probes in Example 5 signal upon hybridization to a target, and the probe-target hybrids have melting temperatures (Table 3) below the amplification cycling temperatures and, thus, the probes do not hybridize to amplification products during the amplification reaction. The probes do not interfere with amplification and are not cleaved during primer extension by a polymerase having 5' exonuclease activity, such as Taq DNA polymerase. Probe cleavage would produce background fluorescence during subsequent melt analysis. Low temperature probes may be present in the amplification reaction mixture rather than being added after amplification.

Figure 13:
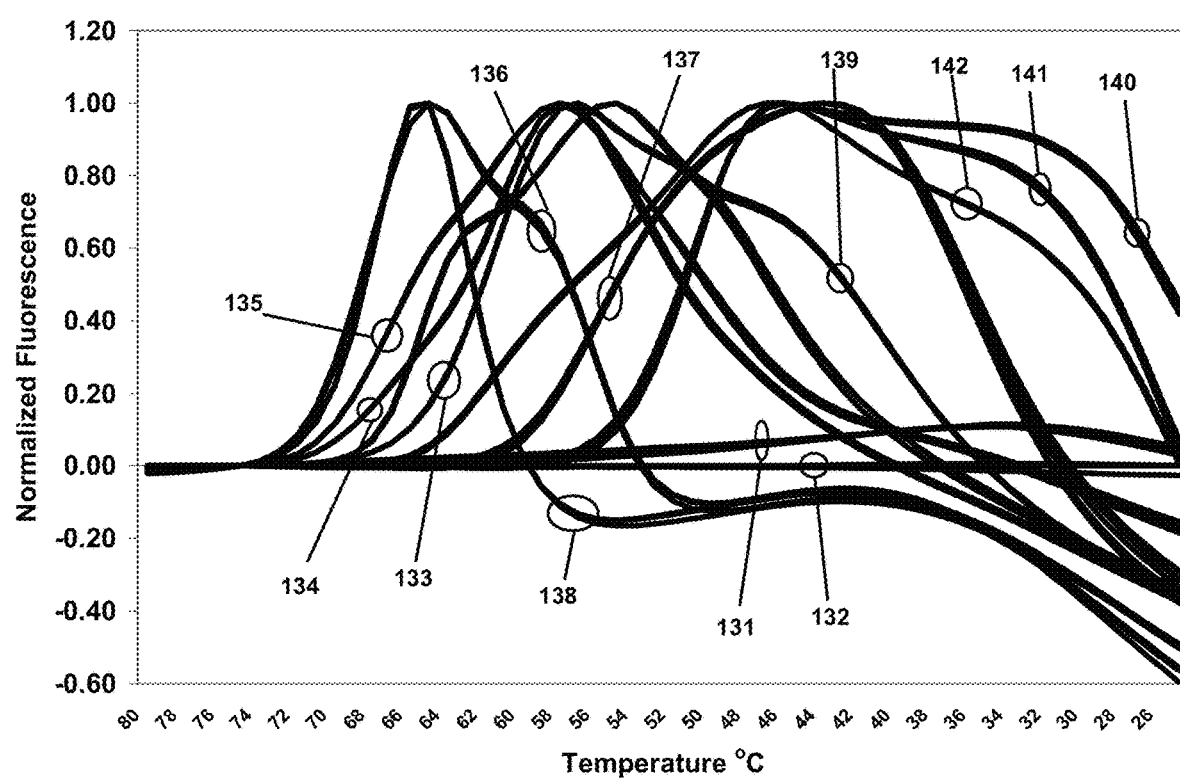
FIG. 13 is a graph presenting annealing curves (fluorescence versus temperature) of the probe sets of Example 5 following amplification of the selected region starting with genomic DNA of different species of bacteria.
Figure 14:
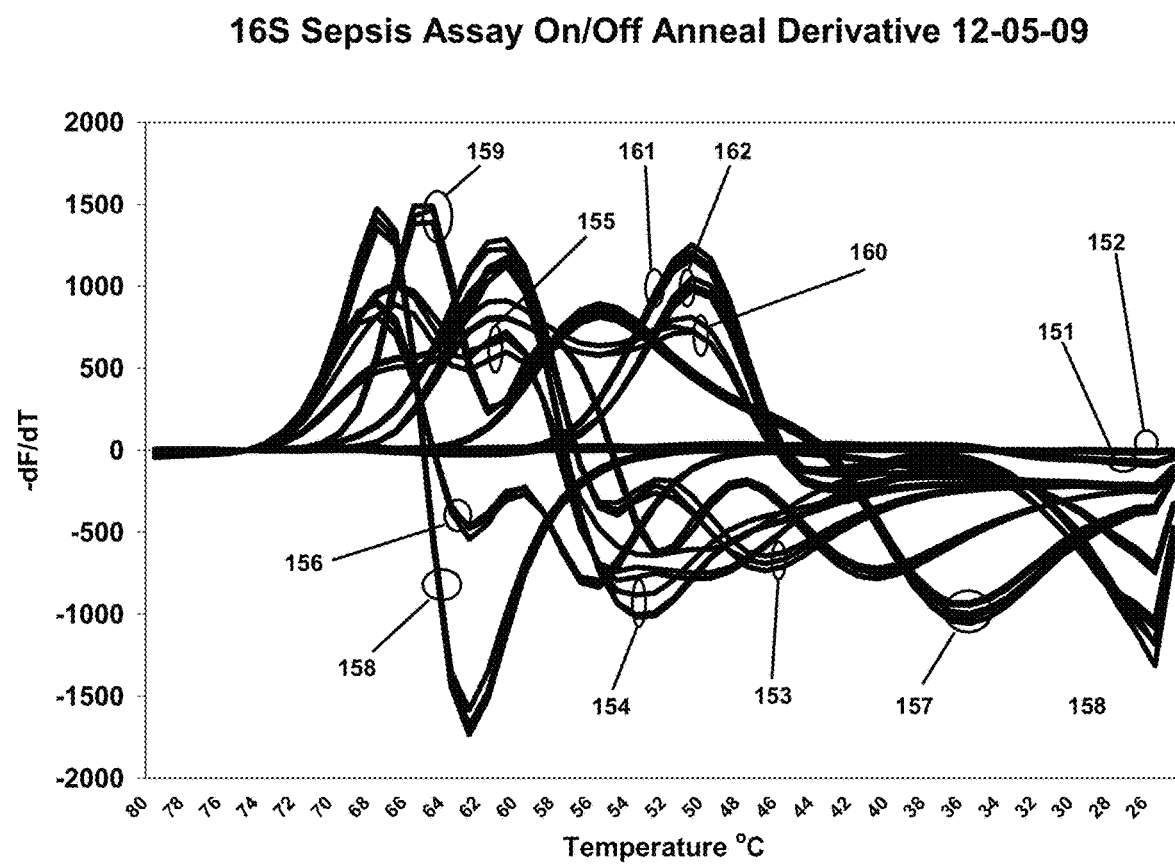
FIG. 14 is a graph presenting the first derivative (−dF/dT) curves of the annealing curves of FIG. 13.

FIGS. 13 and 14 and Table 4 show that the assay of Example 5 is able to distinguish between variable sequences that differ little from one another. The assay distinguished *staphylococcus epidermis* (SE) from *staphylococcus haemolyticus* (SH), which differed from one another at only two nucleotide positions. Thus, as a screening assay for sepsis, the assay is able to differentiate among different target sequences not only at the genus level, but also at the species level.

Figure 15:
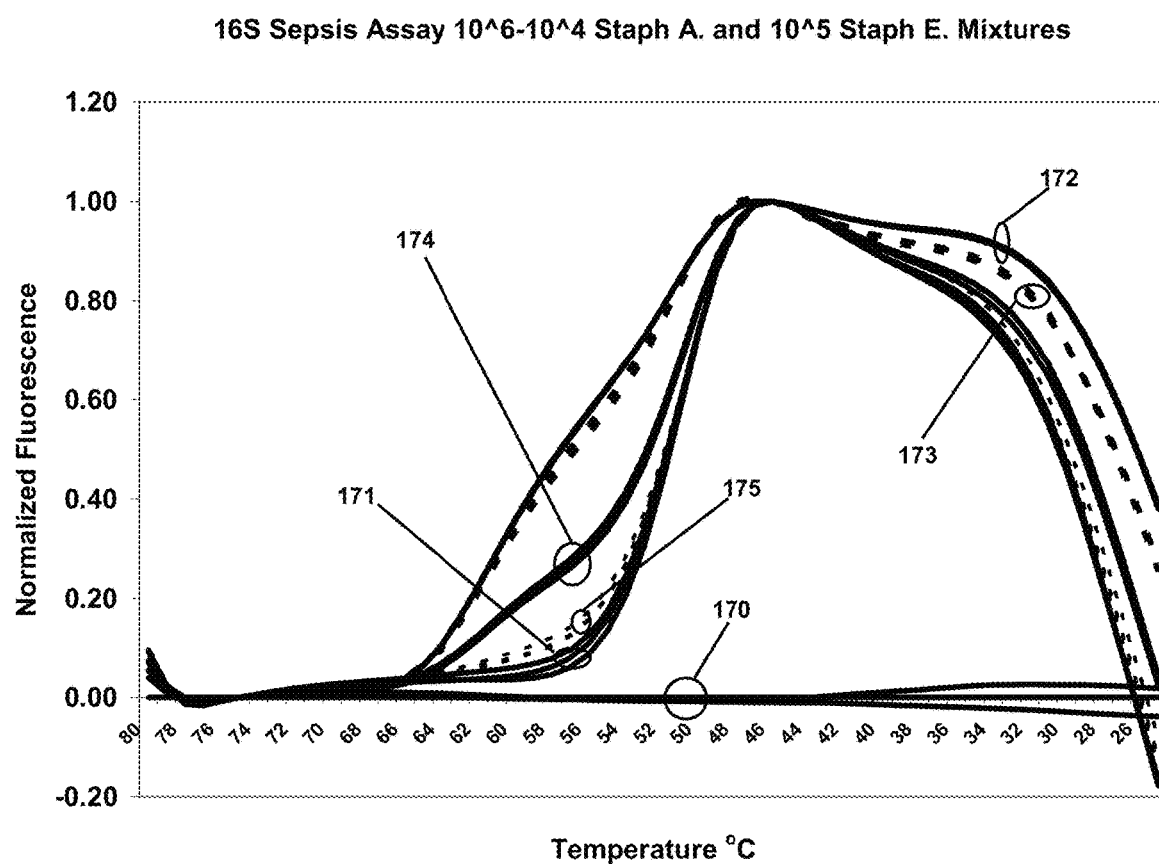
FIG. 15 is a graph presenting annealing curves of the probe sets of Example 5 following amplification of mixtures of genomic DNA described in Example 6.

Example 6 demonstrates the use of the assay of Example 5 with starting samples that contain mixtures of two variants of the variable sequence. FIG. 15 presents anneal curves for mixtures of two variants, *staphylococcus aureus* (COL) and *staphylococcus epidermis* (SE), along with anneal curves for the individual variants. Starting mixtures of each variant with as little as ten percent of the other variant were distinguishable from one another and from the individual variants by the use of a library of curves or a library of digitized information derived from the curves.

Example 7 extends the Sepsis bacterial detection assay of Example 5 from a 203 base region of the 16S rRNA gene using single color to a longer 475 base region of 16S rRNA gene using two colors.

Figure 18:
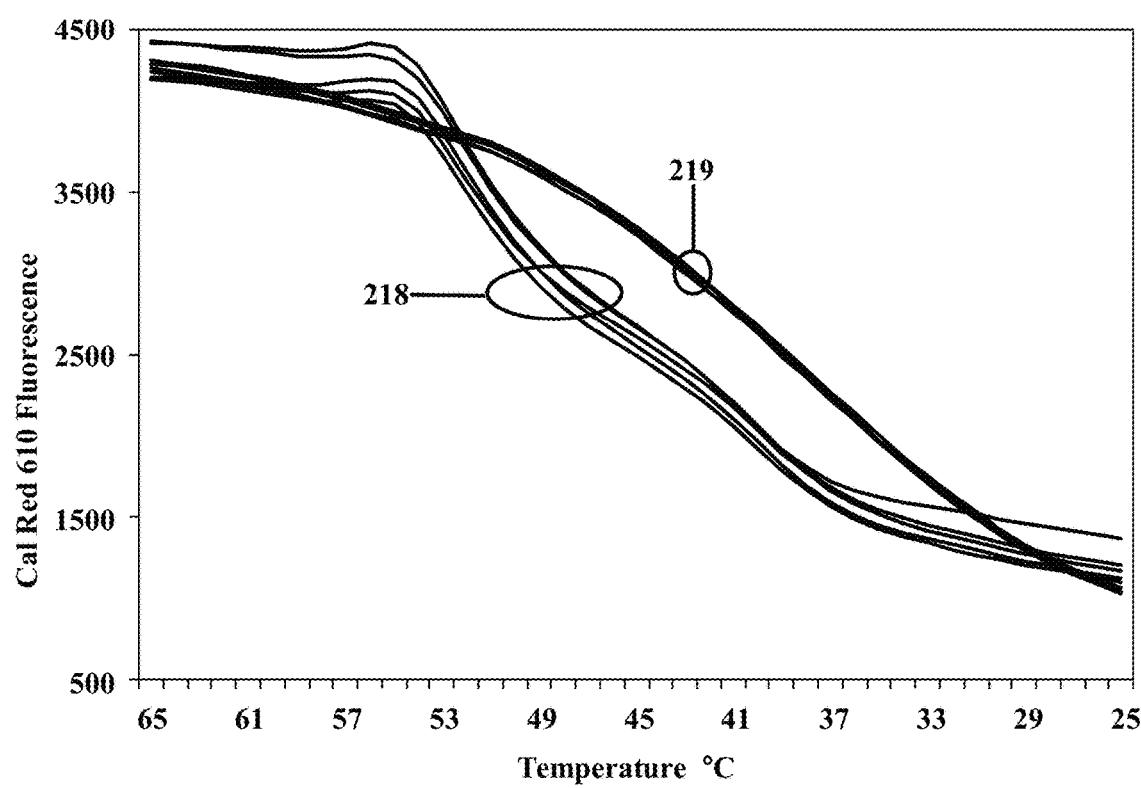
FIG. 18 is a graph presenting the annealing curves (fluorescence versus temperature) for the amplification reaction described in Example 4.

Example 8 extends the analysis of the experiment described in Example 4, using the melting temperatures of the two ON Cal Red probes and their associated OFF probes, and temperature-dependent fluorescence signals from those probes in the absence of target compared to temperature-dependent fluorescence signals from those probes in the presence of amplified *Caenorhabditis elegans* target, presented in FIG. 18. In light of the effective melting temperatures for Probes 3-6 presented in Example 8, the data in FIG. 18 and its derivative curve, FIG. 10B, can be explained as follows. At 65° C. none of the probes is bound to the target sequence, and the fluorescent signal in both the presence and the absence of the target sequence is the same. At temperatures below 65° C. the probes hybridize to the target in the order of their effective melting temperatures: ON Probe 4, OFF Probe 3, OFF Probe 5, ON Probe 6. Because Probe 4 is a signaling probe it generates a signal above the background no-target signal when it binds to the target at about 55° C. As the temperature decreases below about 52° C. the signal from Probe 4 is extinguished as quencher Probe 3 binds to the adjacent target sequence. When the temperature decreases further, OFF Probe 5 hybridizes to the target, but this event is not detected, because Probe 5 is a quencher probe. When the temperature decreases further, ON Probe 6 binds to the target adjacent to Probe 5. This event is detected, because fluorescence coming from unbound signaling Probe 6 is lost by binding of Probe 6 adjacent to quencher Probe 5, which is already bound to the target. No signal above background emanates from signaling Probe 6 when it is adjacent to quencher Probe 6.

The temperature-dependent signaling generated by hybridization of the Probe 4/Probe 3 set to the target is independent of the temperature-dependent signaling generated by hybridization of the Probe 6/Probe 5 set to the target. It will be appreciated that Probe 4 and Probe 6 could use chemical moieties that fluoresce in different colors. It follows that the overall temperature-dependent fluorescent signal observed in this closed-tube system is comprised of the integrated signal arising from all independent components of the system.

The following observation was made from Examples 4 and 8: One or more sets (or pairs) of interacting probes can be designed in which the melting temperature of each quencher probe is higher than the melting temperature of each signaling probe. In this case the fluorescence emanating from the unbound signaling probes will be extinguished as each signaling probe binds to the target adjacent to its already bound quencher probe. When all signaling probes are bound adjacent to their quencher probes at low temperature, the system as a whole will display a very low overall fluorescent signal. Such a system will be very sensitive to the binding or release of very small amounts of bound signaling probe. The sensitivity of said system can be increased by using a dabcyl moiety on the quencher probe, rather than a black hole quencher, or by having no quencher moiety on the signaling probe. Small amounts of such probes will hybridize to small amounts of said targets having an already bound quencher probe. The time required for these molecules to reach equilibrium between the bound and the unbound state can be decreased by decreasing the volume of the reaction. Reactions constructed in this way are amenable to use with amplification reactions which accumulate small numbers of single-stranded target molecules rapidly and in small volumes.

Example 9 illustrates the use of a single set of probes for genotyping of the single nucleotide polymorphism (SNP). The segment of genomic DNA containing the SNP site to be genotyped was amplified using LATE-PCR in the presence of the probe set. The ON probe consisted of a quenched linear probe labeled at the 5' end with a fluorophore and at the 3' end with a quencher. It was complementary to both alleles. This probe was designed to have a melting temperature about 10° C. higher than the OFF Probe and to hybridize adjacent to the OFF probe binding site such that upon binding to the LATE-PCR excess primer strand, the fluorophore moiety of the ON probe resided next the quencher of the OFF probe. The OFF probe was a linear probe labeled at the 3' end with a quencher. This probe was designed to be fully matched to one of the SNP alleles and mismatched to the other allele such that melting temperature of the OFF probe hybridized to the matched SNP allele target was about 10° C. higher than its melting temperature to the mismatched SNP allele target. The relationship of melting temperatures (Tm's) in the assay was as follows: Limiting Primer (71.2° C.)>Excess Primer (66.2° C.)>Primer Annealing (64°

Figure 20:
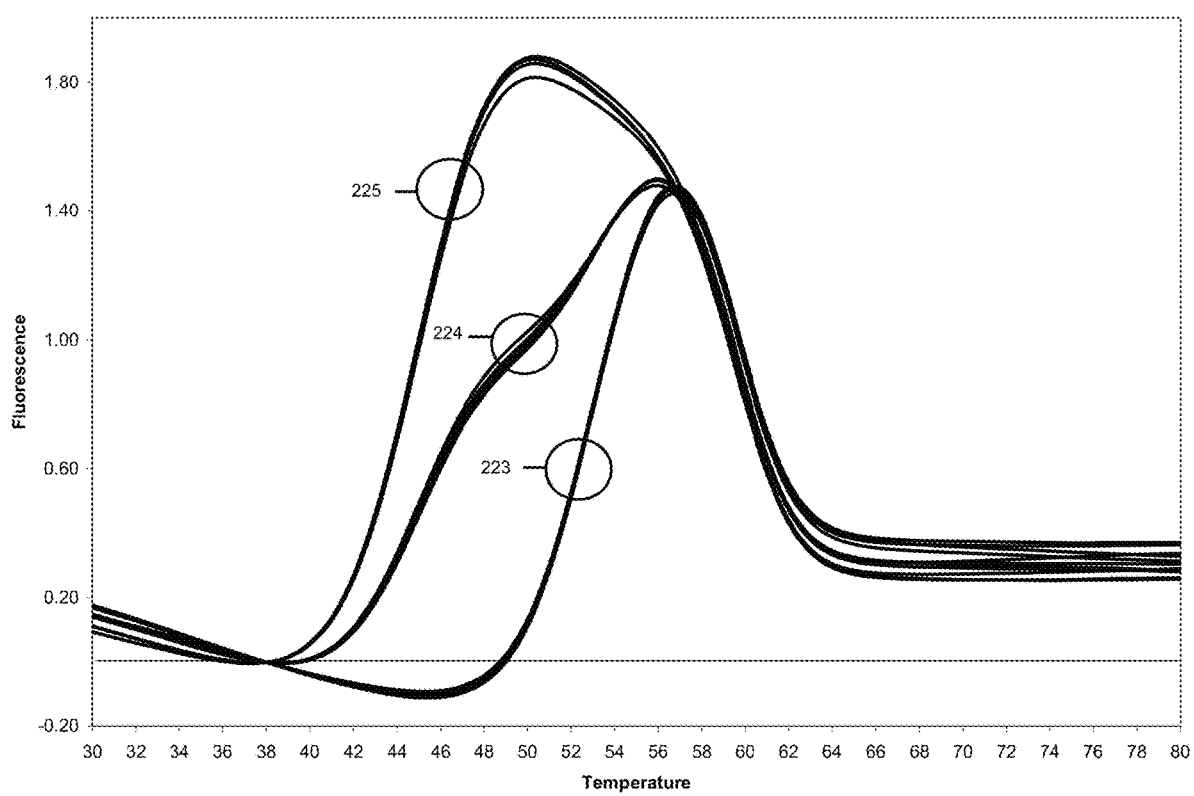
FIG. 20 is a graph presenting normalized melting curves (fluorescence temperature) of the probe set of Example 9 following amplification of homozygous SNP alleles and heterozygous mixture.

C.)>ON Probe (62° C.)>OFF Probe (52° C. versus matched target, 41° C. versus mismatched target). As shown in FIG. 20, the fluorescent pattern generated from this probe pair over a range of detection temperatures identifies the allele configuration of the SNP site in the amplified sample: that is, whether the sample is homozygous for the allele that matches the OFF Probe, whether the sample is homozygous for the mismatched allele, or whether the sample is heterozygous and includes both alleles.

Staphylococcus aureus-typing has become an important tool in the study of strain origin, clonal relatedness, and the epidemiology of outbreaks. Typing also plays an important role in hospital investigations, as methicillin-resistant *S. aureus* (MRSA) is endemic or epidemic in many institutions. Although several different phenotypic and, more recently, molecular techniques are available for differentiating *S. aureus*, no method is clearly superior under all conditions. Currently, macrorestriction analysis by pulsed-field gel electrophoresis (PFGE) is the standard at the United States of America Centers for Disease Control and Prevention (CDC) for *S. aureus* strain typing and has been used successfully to study strain dissemination, especially in the identification of nosocomial outbreaks. However, while PFGE has excellent discriminatory power, it is labor-intensive and difficult to standardize among different laboratories. As with other gel-based typing systems, the interpretation of PFGE results is often subjective. These problems make the exchange of strain typing information difficult and complicate the creation of an *S. aureus* and MRSA typing database.

DNA sequencing is a powerful approach to strain typing with advantages in speed, unambiguous data interpretation, and simplicity of large-scale database creation. Recently, DNA sequencing of the polymorphic X, or short sequence repeat (SSR), region of the protein A gene (spa) has been proposed as an alternative technique for the typing of *S. aureus*. The polymorphic X region consists of a variable number of 24-bp repeats and is located immediately upstream of the region encoding the C-terminal cell wall attachment sequence. The existence of well-conserved regions flanking the X region coding sequence in spa allows the use of primers for PCR amplification and direct sequence typing. The sequencing of the spa SSR region combines many of the advantages of a sequencing-based system such as MLST but may be more rapid and convenient for outbreak investigation in the hospital setting, because spa typing involves a single locus. Inasmuch as the protein A X region has a high degree of polymorphism, it may have a variation rate (or clock speed) that provides suitable discrimination for outbreak investigation." (Shopsin et al., J. Clinical Microbiology, November 1999, pages 3556-3563)

Figure 22:
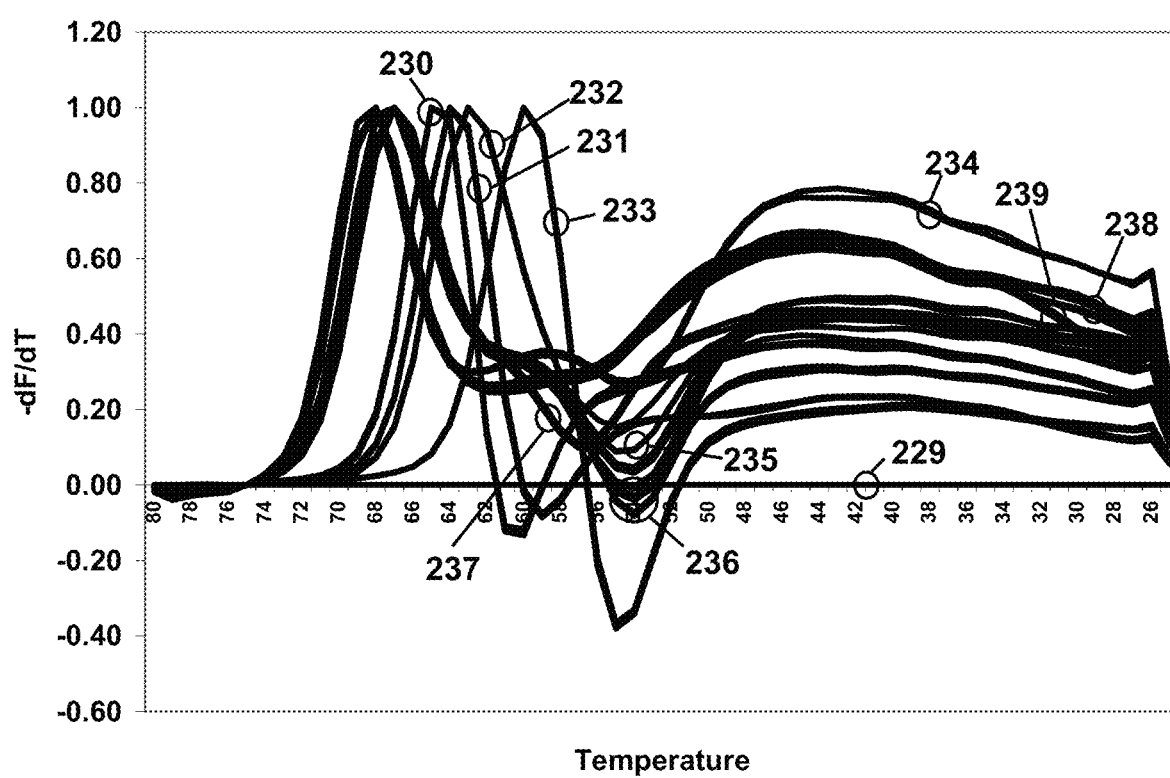
FIG. 22 is a graph presenting the first derivative (−dF/dT) of post-amplification annealing curves of twelve MRSA samples using the single set of ON/OFF probes described in Example 10.

A different approach to spa typing than PFGE or DNA sequencing (Shopsin et al) is the use of a LATE-PCR assay using ON/OFF probes to distinguish strains of *S. aureus* based on the X repeat region and to create a signature library where different strains can be identified. For spa typing there are repeats of 24 bases where each repeat might have a slightly different sequence and the number of repeats vary with SPA type. Example 10 describes a LATE-PCR assay for spa typing utilizing a single set of one signaling (ON) probe and one quencher (OFF) probe. The ON/OFF probe set was tested against twelve sequenced spa types of MRSA samples, some of which had the same spa types, others where spa types were similar, and still others where the spa type was very different. First derivative annealing curves of fluorescence versus temperature for the twelve samples are shown in FIG. 22. All results showed the expected differentiation and definition of each spa type. When spa types were expected to be the same, the same signature appeared.

EXPERIMENTAL

Example 1

Detection of Drug Resistance in the rpoB Gene for Strains of *GM. Tuberculosis*

A LATE-PCR amplification was performed using a single pair of primers to amplify a 150 base pair region of the rpoB gene for each of several strains of *Mycobacterium tuberculosis*. The amplification provided a 101 base-pair region of the gene, which is known to contain mutations responsible for drug resistance for rifampicin, as a single-stranded nucleic acid target sequence (the Excess Primer strand of each LATE-PCR amplification). Following amplification, each single-stranded nucleic acid target sequence was probed using six separate probes that were included in the original amplification reaction mixture.

The probes in combination spanned the 101 base pairs of the single-stranded nucleic acid target sequence. Three of the probes were signaling probes. The signaling probes were quenched molecular beacon probes with two-nucleotide-long stems. Each included covalently bound labels: the fluorophore Quasar 670 on one end and a Black Hole Quencher 2, BHQ2, (Biosearch Technologies, Novato, Calif.), on the other end. The other three probes were quencher probes terminally labeled with BHQ2 only, with no fluorophore. In this example the Tm's of the signaling probes with respect to the drug-sensitive strain differed from one another, and the Tm's of the quencher probes with respect to the drug-sensitive strain differed from one another. The three probe sets were detectably distinguishable.

At the end of amplification, probe-target hybridizations were analyzed as a function of temperature. In this example, hybridizations were characterized by the use of melt profile analysis. Reaction components and conditions were as follows:

```
Limiting Primer:
                                          (SEQ ID No. 1)
5' CTCCAGCCAGGCACGCTCACGTGACAGACCG Excess Primer:
                                          (SEQ ID No. 2)
5' CCGGTGGTCGCCGCGATCAAGGAG Target: Strain 13545
                                          (SEQ ID No. 3)
5' CCGGTGGTCGCCGCGATCAAGGAGTTCTTCGGCACCAGCCAGCTGAG

CCAATTCATGGACCAGAACAACCCGCTGTCGGGGTTGACCCACAAGCG

CCGACTGTCGGCGCTGGGGCCCGGCGGTCTGTCACGTGAGCGTGCCGG

GCTGGAG

Target: Strain 18460
                                          (SEQ ID No. 4)
5' CCGGTGGTCGCCGCGATCAAGGAGTTCTTCGGCACCAGCCAGCTG

AGCCAATTCATGGTCCAGAACAACCCGCTGTCGGGGTTGACCCACAAGC

GCCGACTGTCGGCGCTGGGGCCCGGCGGTCTGTCACGTGAGCGTGCCG

GGCTGGAG
```

-continued

Target: Strain 9249
(SEQ ID No. 5)
5'CCGGTGGTCGCCGCGATCAAGGAGTTCTTCGGCACCAGCCAGCTG

AGCCAATTCATGGACCAGAACAACCCGCTGTCGGGGTTGACCCACAAGC

GCCGACTGTTGGCGCTGGGGCCCGGCGGTCTGTCACGTGAGCGTGCCGG

GCTGGAG

The underline in the sequence of each of strains 18460 and 9249 denotes the location of the nucleotide change from the drug-sensitive strain 13545.

```
Probe 1:
                                      (SEQ ID No. 6)
5'-BHQ2-CTGGTTGGTGCAGAAG-C₃

Probe 2:
                                      (SEQ ID No. 7)
5'-BHQ2-TCAGGTCCATGAATTGGCTCAGA-Quasar 670

Probe 3:
                                      (SEQ ID No. 8)
5'-BHQ2-CAGCGGGTTGTT-C₃

Probe 4:
                                      (SEQ ID No. 9)
5'-BHQ2-ATGCGCTTGTGGATCAACCCCGAT-Quasar 670

Probe 5:
                                      (SEQ ID No. 10)
5'-Quasar 670-AAGCCCCAGCGCCGACAGTCGTT BHQ2

Probe 6:
                                      (SEQ ID No. 11)
5'-ACAGACCGCCGG BHQ2
```

A three carbon linker is denoted with $C_3$ while a Black Hole Quencher 2 is denoted with BHQ2 (Biosearch Technologies, Novato, Calif.).

LATE PCR amplifications were carried out in a 25 μl volume consisting of 1× PCR buffer (Invitrogen, Carlsbad, Calif.), 2 mM MgCl2, 200 nM dNTPs, 50 nM Limiting Primer, 1000 nM Excess Primer, 1.25 units of Platinum Taq DNA Polymerase (Invitrogen, Carlsbad, Calif.), 500 nM of probes 1, 3 and 6, and 200 nM of probes 2, 4 and 5. For each strain tested approximately 1000 genomes equivalents were used. Amplification reactions for each strain were run in triplicate.

The thermal profile for the amplification reaction was as follows: 98° C./3 min for 1 cycle, followed by 98° C./10 s-75° C./40 s for 50 cycles, followed by fluorescent acquistion at each degree starting with an anneal at 75° C. with 1° C. decrements at 30 s intervals to 34° C. followed by 10 min at 34° C. This was followed by a melt starting at 34° C. with 1° C. increments at 30 s intervals to 81° C.

The melting temperatures of the probes was performed utilizing the computer program Visual OMP 7.0 with the concentrations of target, signaling probes, and quencher probes at 100 nM, 200 nM and 500 nM respectively. The Tm's were as follows: Probe 1, 50° C.; Probe 2, 63° C.; Probe 3, 56° C.; Probe 4, 67° C.; Probe 5, 75° C.; and Probe 6, 63° C. Analysis of the probe target hybridizations following amplification was by melt curve analysis using the first derivative for Quasar 670 fluorescence for temperatures between 35° C. to 78° C. From this data set the highest fluorescent value was used to normalize the data to one. If the value used was negative, it was multiplied by (−15); if it was a positive number, it was multiplied by fifteen.

FIG. 2 illustrates binding of the three prose sets (Probes 1/Probe 2, Probe 3/Probe 4, and Probe 5/Probe 6) to the single-stranded nucleic acid target sequence utilizing drug-susceptible strain 13545 as the target. In FIG. 2, strand 21 is the target strand, strand 23 is the Excess Primer, and strand 22 is the Limiting Primer. For the purpose of illustration probes 1-6 are shown hybridized to strand 21 in a 3' to 5' orientation with their mismatched ends above. Mismatches between the probes and strand 21 and between the Limiting Primer and strand 21 are bolded. Fluorophore and quencher labels are omitted from FIG. 2 but are given above in the sequence descriptions. Some of the nucleotides in the probe sequences were deliberately mismatched to the sensitive strain 13545 such as Probe 1, which contains mismatches in positions 31(A to G) and 38(T to G) relative to the 5' end of strand 21. Other mismatches are in Probe 2, position 62(A to A), Probe 4, position 86 (A to C). Within the Limiting Primer at position 142(A to G) is a mismatch which was included to reduce a hairpin that occurred in the original target strand. In addition to these mismatches in the sensitive strain 13545, strains 18460 has a nucleotide mismatch at position 59 (T to T) while strain 9249 has a mismatch at position 104 (G to T).

It will be appreciated that LATE-PCR amplification provides a sample containing the Excess Primer strand, which comprises the single-stranded nucleic acid target sequence that is actually probed. The Excess Primer strand includes the Excess Primer sequence at one end and the complement of the Limiting Primer sequence at the other end. In this case, due to the mismatch between the Limiting Primer and strand 21, the Excess Primer strand will differ from strand 21 at position 142, which will be a T rather than a G. As to the region of strand 21 complementary to probes 1-6, the Excess Primer strand is identical to strand 21.

FIG. 3A presents the results of the analysis for two different strains of M. tuberculosis, strain 13545 and strain 18460. Data from analysis of the triplicate samples of the separate amplifications of the two strains are superimposed for the purpose of illustration. Circle 311 represents the drug-resistant strain 18460 (D516V, an aspartic acid located at amino acid position 516 changed to a valine), while, circle 312 shows the replicates from the drug-sensitive strain 13545 (V146F, a valine located at amino acid position 146 changed to a phenylalanine). FIG. 3B presents the results for drug-resistant strain 9249 and drug-sensitive strain 13545, where circle 313 shows the replicates for drug-resistant strain 9249 (S531L, a serine located at amino acid position 513 changed to a leucine) and circle 314 shows the replicates from the drug-sensitive strain 13545 (V146F).

Example 2

The Detection of a Drug Resistance Strain of M. tuberculosis in a Mixed Sample

LATE PCR amplifications were performed to provide single-stranded nucleic acid target sequences using resistant M. tuberculosis strain 18640 (D516V, an aspartic acid located at amino acid 516 changed to a valine) and the sensitive strain 13545 in different ratios to determine the level of sensitivity within a mixed sample. Reaction components and conditions are described in Example 1, except for the starting target sequences included in the reaction mixtures. Amplicons generated from strain 18640 and strain 13545 using the primers from Example 1 comprise a single nucleotide variation within the hybridization sequence of probe 2. In this embodiment, probe 2 is a signaling probe.

Alternatively, in some embodiments, a quencher probe that hybridizes to the region of the amplicon containing the variable nucleotide may be employed, and a corresponding signaling probe is design to hybridize adjacently. One reaction mixture contained only strain 18460, and another reaction mixture contained only strain 13545. Each of these 100% controls contained approximately 100,000 genomic DNA copies of the pertinent strain. Reaction mixtures for a first mixed sample contained 20% (approximately 20,000 genomes) of resistant strain 18460 with 80% (approximately 80,000 genomes) of sensitive strain 13545. The reaction mixture for a second mixed sample contained 10% of strain 18460 (10,000 genomes) with 90% of strain 13545 (90,000 genomes). The reaction mixture for a third mixed sample contained 5% of strain 18460 (5,000 genomes) with 95% of strain 13545 (95,000 genomes). The reaction mixture for a fourth mixed sample contained 1% of strain 18460 (1,000 genomes) with 99% of strain 13545 (99,000 genomes). Amplification reactions were run in triplicate.

The thermal profile for the amplification reaction was as follows: 98° C./3 min for 1 cycle, followed by 98° C./10 s-75° C./40 s for 50 cycles, followed by fluorescent acquisition at each degree starting with an anneal at 75° C. with 1° C. decrements at 30 s intervals to 34° C. then a hold for 10 min at 34° C. This is followed by a melt starting at 34° C. with 1° C. increments at 30 s intervals to 81° C. followed by an anneal starting at 75° C. with 1° C. decrements at 30 s intervals to 34° C. This melt/anneal profile was repeated three more times.

The data used for graphical analysis of the hybridization of the six probes was the average of each replicate from the last three melt profiles. From these average values the fluorescence at 35° C. was subtracted, and the resulting values were normalized by division of all values with the fluorescence at 78° C. The first derivative of the resulting data were then generated and normalized by dividing all values using the largest positive value.

In order to remove the contribution of the sensitive strain DNA from mixtures containing both sensitive and resistant strain DNA's, replicates of the pure sensitive strain DNA samples (100% controls) were used to generate average-derived-values at every temperature, as described above. These values were then subtracted from the derived-average-values of each mixture to arrive at the contribution of the resistant strain. In addition, the scatter among separate samples of pure sensitive DNA was established by subtracting the derived-average-values of pure sensitive DNA from each of the individual samples of pure sensitive DNA.

Figure 4C:
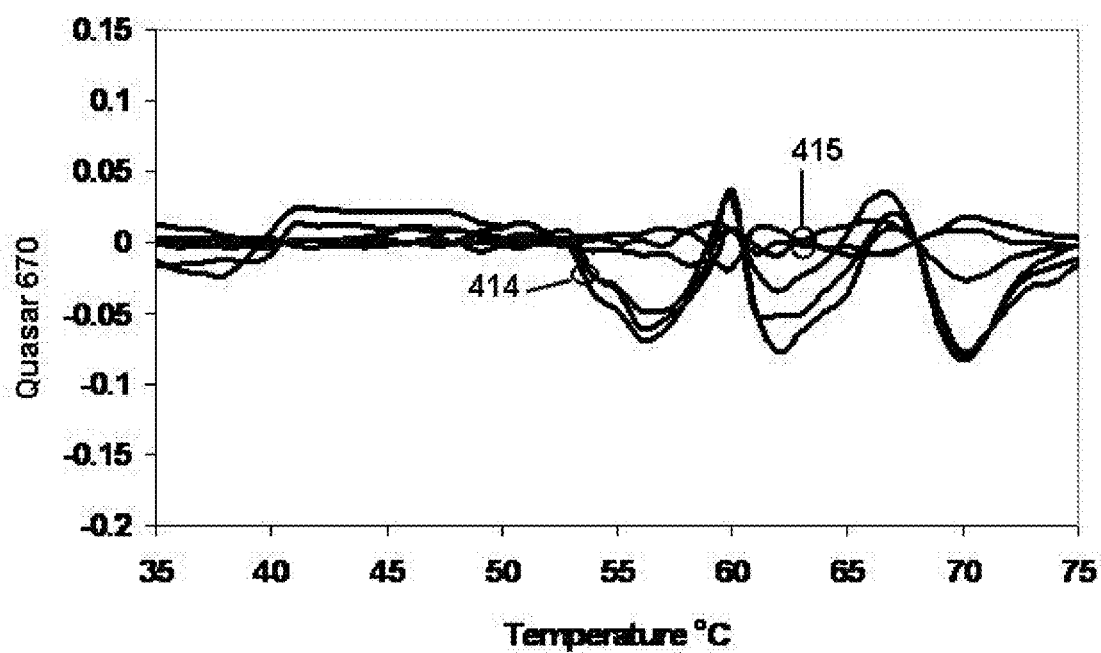
Figure 4D:
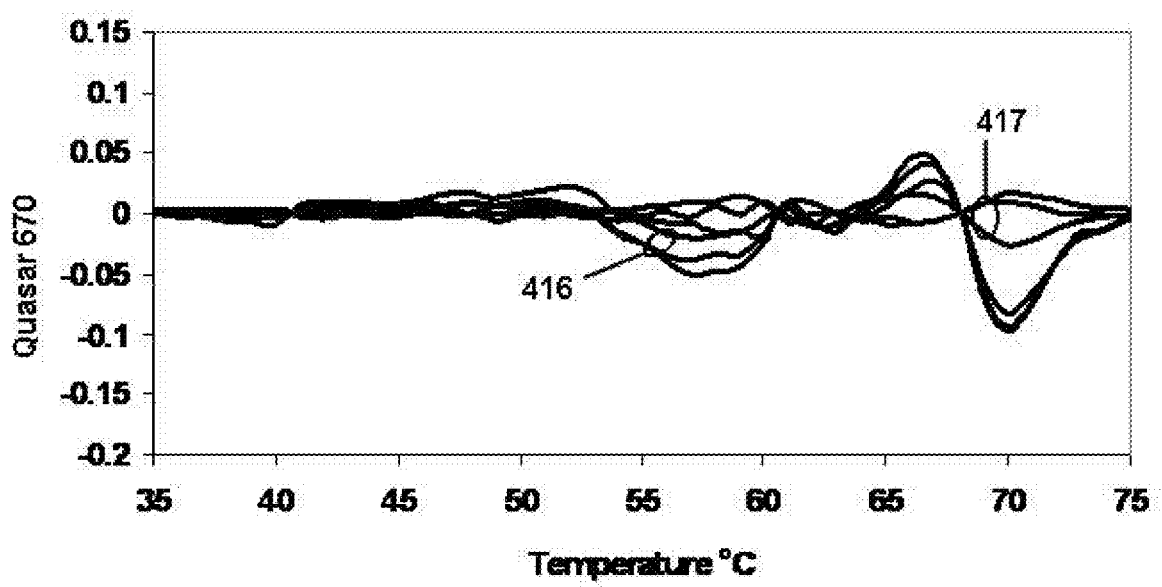

FIGS. 4A-4D show the resulting analysis. They display the signal from various percentages of the resistant strain 18460 in an increasing background of sensitive strain 13545. FIG. 4A shows this signal with a mixed sample of 20% resistant strain 18460 in a background of 80% sensitive strain 13545, where circle 410 identifies the contribution of the resistant strain in replicates of the mixture, and circle 411 identifies the scatter among replicates for the pure sensitive strain. FIG. 4B shows this signal with the 10% mixture, with circle 412 representing the contribution of the resistant strain in replicates of the mixture, and circle 413 representing scatter among replicates for the pure sensitive strain. FIG. 4C shows the signal from the mixture of 5% resistant strain replicates (circle 414 identifying the contribution of the resistant strain in replicates of the mixture, and circle 415 identifying scatter among replicates for the pure sensitive strain). FIG. 4D shows the signal from the mixture of 1% resistant strain. Circle 416 identifies the contribution of the resistant strain in replicates of the mixture, and circle 417 identifies the scatter among replicates of the pure sensitive strain.

Example 3

Multi-drug resistance detection in strains of *M. tuberculosis*

A multiplex LATE-PCR assay was used to provide multiple single-stranded target nucleic acids to detect drug resistance in the three genes, gyrA (fluoroquinolones), katG (isoniazid), and rpoB (rifampicin), of each of three strains, 13545, 202626 and 15552. For the gyrA gene the strains 13545 and 202626 were drug-sensitive while strain 15552 (A90V, an aspartic acid located at amino acid position 90 changed to a valine) was drug-resistant. For the katG gene the strain 202626 was drug-sensitive, while strain 13545 (S315T, a serine located at amino acid position 315 changed to a tyrosine) and strain 15552 (S315N, a serine located at amino acid position 315 changed to a asparagine) were resistant. For the rpoB gene strain 13545 was a sensitive strain while strain 15552 (S531L, a serine located at amino acid position 513 changed to a leucine) and strain 202626 (H526D, a histidine located at amino acid position 513 changed to an aspartic acid) were resistant.

Reaction components and conditions were as follows:
For the gyrA gene

```
Limiting Primer:
                                         (SEQ ID No. 12)
5' ACCAGGGCTGGGCCATGCGCACCA Excess Primer:
                                         (SEQ ID No. 13)
5' GGACCGCAGCCACGCCAAGTC Target: Strain 13545
                                         (SEQ ID No. 14)
5'GGACCGCAGCCACGCCAAGTCGGCCCGGTCGGTTGCCGAGACCATGGG

CAACTACCACCCGCACGGCGACGCGTCGATCTACGACAGCCTGGTGCGCA

TGGCCCAGCCCTGGT

Target: Strain 202626

Identical to strain 13545

Target: Strain 15552
                                         (SEQ ID No. 15)
5'GGACCGCAGCCACGCCAAGTCGGCCCGGTCGGTTGCCGAGACCATGGG

CAACTACCACCCGCACGGCGACGTGTCGATCTACGACAGCCTGGTGCGCA

TGGCCCAGCCCTGGT

Probe 1:
                                         (SEQ ID No. 16)
5' CGACCGGGCC-BHQ2

Probe 2:
                                         (SEQ ID No. 17)
5' Cal Red 610-AACCCATGGTCTCGGCAACTT-BHQ2

Probe 3:
                                         (SEQ ID No. 18)
5' Cal Red 610-AATCGCCGTGCGGGTGGTAGTT-BHQ2

Probe 4:
                                         (SEQ ID No. 19)
5'GCTGTCGTAGATCGACGCG-BHQ2
```

For the katG gene

```
Limiting Primer:
                                        (SEQ ID No. 20)
5' AGCGCCCACTCGTAGCCGTACAGGATCTCGAGGAAAC Excess Primer:
                                        (SEQ ID No. 21)
5' TCTTGGGCTGGAAGAGCTCGTATGGCAC Target: Strain 202626
                                        (SEQ ID No. 22)
GCTTGGGCTGGAAGAGCTCGTATGGCACCGGAACCGGTAAGGACGCGATC

ACCAGCGGCATCGAGGTCGTATGGACGAACACCCCGACGAAATGGGACA

ACAGTTTCCTCGAGATCCTGTACGGCTACGAGTGGGAGCT

Target: Strain 13545
                                        (SEQ ID No. 23)
GCTTGGGCTGGAAGAGCTCGTATGGCACCGGAACCGGTAAGGACGCGATC

ACCACCGGCATCGAGGTCGTATGGACGAACACCCCGACGAAATGGGACA

ACAGTTTCCTCGAGATCCTGTACGGCTACGAGTGGGAGCT

Target: Strain 15552
                                        (SEQ ID No. 24)
GCTTGGGCTGGAAGAGCTCGTATGGCACCGGAACCGGTAAGGACGCGATC

ACCAACGGCATCGAGGTCGTATGGACGAACACCCCGACGAAATGGGACA

ACAGTTTCCTCGAGATCCTGTACGGCTACGAGTGGGAGCT

Probe 1:
                                        (SEQ ID No. 25)
5' Cal Orange 560-AAGTGATCGCGTCCTTACCTT-BHQ2

Probe 2:
                                        (SEQ ID No. 26)
5' GACCTCGATGCAGCTG-BHQ2
```

For the rpoB gene
Limiting Primer: same as in Example 1
Excess Primer: same as in Example 1

```
Target Strain: 202626
                                        (SEQ ID No. 27)
5' CCGGTGGTCGCCGCGATCAAGGAGTTCTTCGGCACCAGCCAGCTGAG

CCAATTCATGGACCAGAACAACCCGCTGTCGGGGTTGACCGACAAGCGC

CGACTGTCGGCGCTGGGGCCCGGCGGTCTGTCACGTGAGCGTGCCGGGC

TGGAG
```

Target: Strain 15552
Same as strain 9249 set forth in Example 1
Target: Strain 13545
Set forth in Example 1
Probes used for rpoB gene:
Probes 1-6 set forth in Example 1
The underline in a target sequence denotes the location of the nucleotide change from the drug sensitive strain.

LATE-PCR amplifications were performed in triplicate carried out in a 25 ul volume consisting of 1×PCR buffer (Invitrogen, Carlsbad, Calif.), 2 mM MgCl2, 200 nM dNTPs, 50 nM Limiting Primer and 1000 nM Excess Primer for each primer set, 1.25 units of Platinum Taq DNA Polymerase (Invitrogen, Carlsbad, Calif.), for the gyrA probes 500 nM of probes 1 and 3 with 200 nM of probes 2 and 4, for the katG probes 200 nM of probe 1 and 500 nM of probe 2, and for the rpoB probes the concentrations set forth in Example 1. For all strains tested approximately 1000 genomes equivalents of pre-amplification target were used, and amplification reactions for each strain were run in triplicate.

The thermal profile for the amplification reaction was as follows: 98° C./3 min for 1 cycle, followed by 98° C./10 s-75° C./40 s for 50 cycles, followed by an anneal starting at 75° C. with 1° C. decrements at 30 s intervals to 34° C., followed by 10 min at 34° C. This was followed by a melt starting at 34° C. with 1° C. increments at 30 s intervals to 81° C.

Probe-target hybridizations were analyzed by the melt curve analysis using the first derivative for each fluor separately for the temperatures between 35° C. to 78° C. From each data set the highest fluorescent value was used to normalize the data to one. If the value used is negative then it is multiplied by −15 (minus fifteen), if it was a positive number then it is multiplied by +15 (plus fifteen). Each of the strains tested differs in respect to drug resistance. See Table 1 below. For example, strain 13545 is resistant to isoniazid drugs while sensitive to both fluorquinolones and rifampicin while strain 15552 is resistant to all three drugs.

TABLE 1

| Drug | Gene | Strain 13545 | Strain 202626 | Strain 15552 |
| --- | --- | --- | --- | --- |
| Fluorquinolones | gyrA | Sensitive | Sensitive | Resistant |
| Isoniazid | katG | Resistant | Sensitive | Resistant |
| Rifampicin | rpoB | Sensitive | Resistant | Resistant |

FIG. 5 illustrates probe binding of primers and probes to strand 51, the gyrA target of strain 13545, which, because the primers were perfectly complementary to the original target strand, is identical to the Excess Primer strand. In FIG. 5 the underlined of sequence 51 are the nucleotides of the Excess Primer and sequence 52 is the Limiting Primer. Probes 1-4 are shown hybridized to strand 51 in a 3' to 5' orientation with their unmatched ends above. The probes are labeled with their respective quenchers or fluorophores (not shown) as described above. Strain 15552 differs relative to the 5' end at position 72, a T nucleotide from that of both strains 13545 and 202626 which has a C nucleotide in that position.

Figure 6:
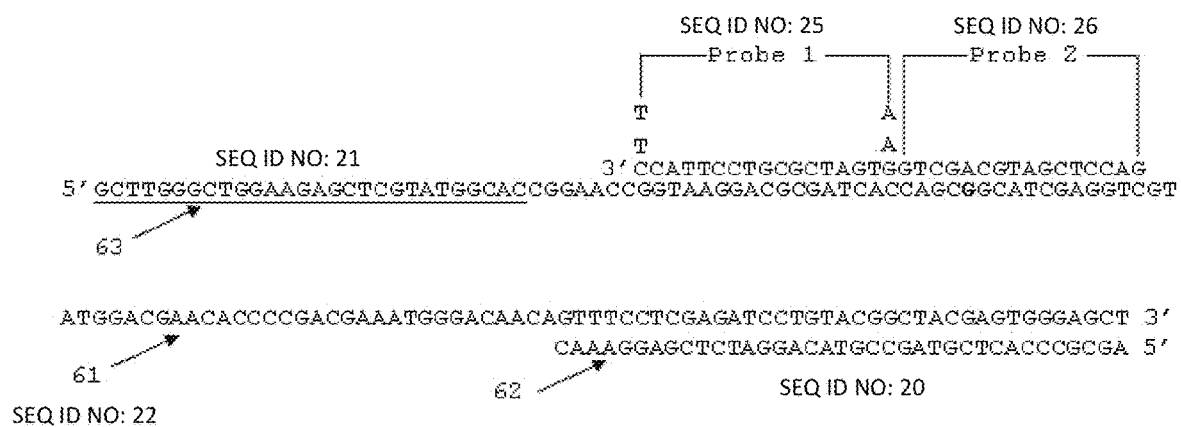
FIG. 6 is a schematic representation of another single-stranded nucleic acid sequence from Example 3 showing probe binding locations and primer binding locations.

FIG. 6 illustrates probe binding of primers and probes to strand 61, the katG target of strain 202626, which, because the primers were perfectly complementary to the original target strand, is identical to the Excess Primer strand; that is, one of the three single-stranded products of the LATE-PCR amplification reaction. In FIG. 6, underlined sequence 63 is the nucleotides of the Excess Primer, and underlined sequence 62 is the Limiting Primer. Probes 1, 2 are shown hybridized to strand 61 in the 3' to 5' orientation with their mismatched ends above. Relative to the 5' end of strand 61, all three strains differ at position 56 (G, in bold) to Probe 2. At position 54 is a "G" as shown for strain 202626, but it is a "C" in strain 13545 and an "A" in strain 15552. The Excess Primer contains a deliberate mismatch at the 5' end (a "T" rather than the "G" in each of the targets) to reduce potential mispriming during the linear phase of LATE-PCR amplification.

The thermal profile for the amplification reaction was as follows: 98° C./3 min for 1 cycle, followed by 98° C./10 s-75° C./40 s for 50 cycles, followed by an anneal starting at 75° C. with 1° C. decrements at 30 s intervals to 34° C. followed by 10 min at 34° C. This is followed by a melt starting at 34° C. with 1° C. increments at 30 s intervals to 81° C.

Figure 7A:
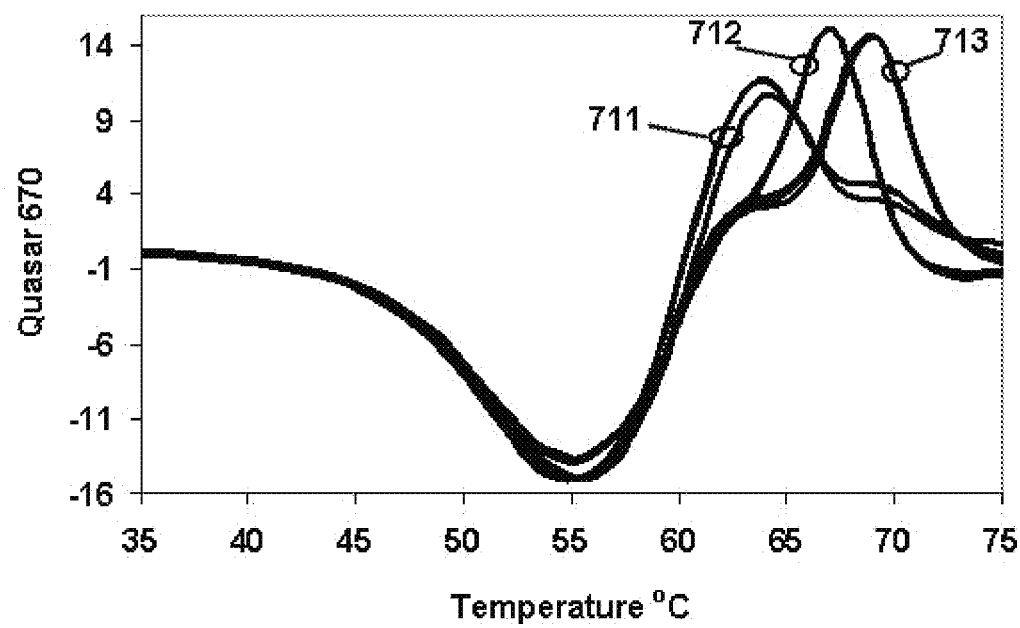
FIGS. 7A-7C are graphs of fluorescence versus temperature for each of the fluorophores in the sample of Example 3.
Figure 7B:
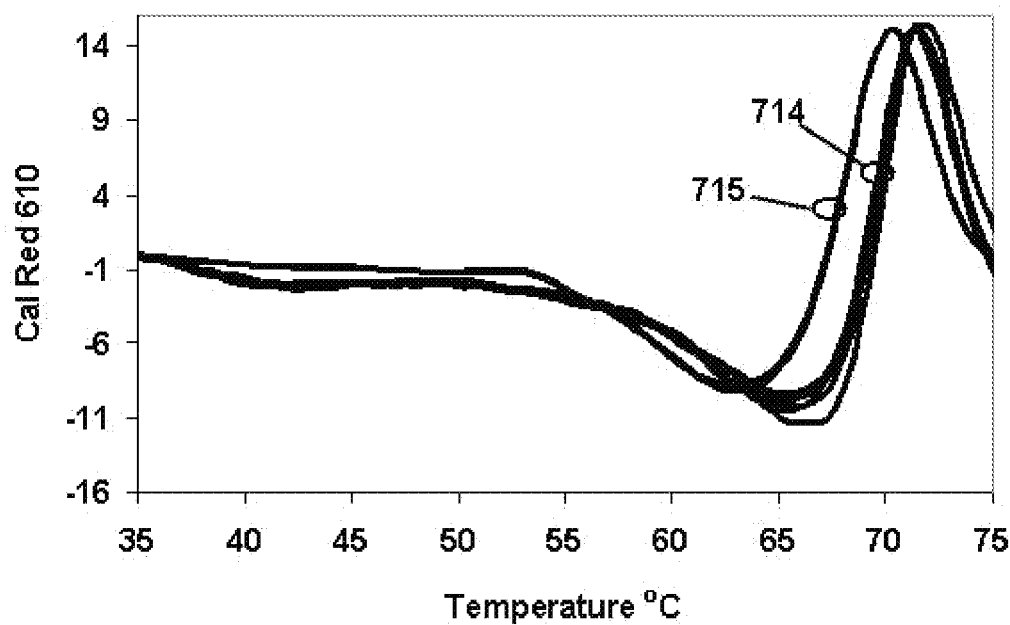
Figure 7C:
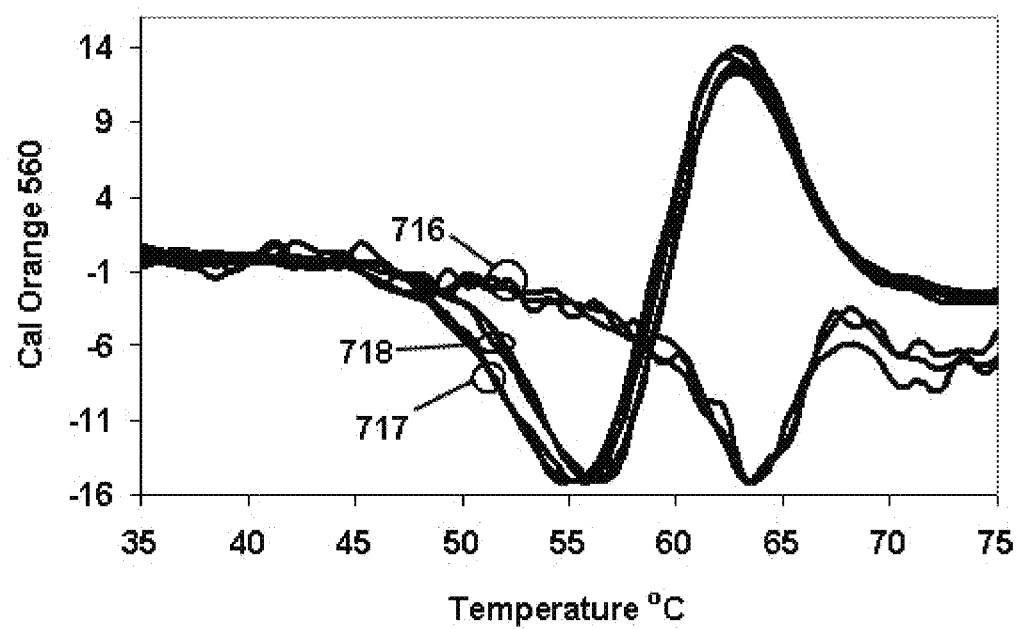

FIG. 7A presents the normalized fluorescence readings of all six probes for the rpoB gene in three different strains of *M. tuberculosis* as a function of the temperature. Circle 711 represents the replicates for strain 202626, while circle 712 shows the replicates for strain 15552 and circle 713 are the replicates for strain 13545. FIG. 7B shows the results for the gyrA probes, which distinguish the sensitive strains 202626 and 13545 (circle 714) from the drug resistant strain 15552 (circle 715). The results for the katG gene probes are shown in FIG. 7C, in which all three melt derivatives are different, circle 716 are replicates of the sensitive strain 202626, while the resistant strains 13545 and 15552 are represented by circle 717 and circle 718, respectively.

Example 4

Use of Multiple Probes and Multiple Colors for Species-Level Identification

To demonstrate the ability of embodiments of the methods provided herein to analyze long sequences, the method was used to distinguish between nematode species. LATE-PCR assays were performed using a set of 3 Limiting Primers and an Excess Primer for the mitochondrial cytochrome oxidase I gene. Reaction components and conditions were as follows. In the primer and probe sequences, nucleotides mismatched to the *C. elegans* sequence are identified by an asterisk (*). In the probe sequences, nucleotides added to form a two base-pair stem are underlined.

```
Limiting Primer One
                                       (SEQ ID No. 28)
5'-GGTT*ATACCTAG*TATAATT*GGTGGTTTTGGTAAT*TG Limiting Primer Two
                                        SEQ ID No. 29)
5'-GGTT*ATACCTAG*TATAATT*GGTGGTTTTGGTAACTG Limiting Primer Three
                                       (SEQ ID No. 30)
5'-GGTT*ATACCTAG*TATAATT*GGTGGTTTTGGC*AAT*TG Excess Primer
                                       (SEQ ID No. 31)
5'-A*CTA*GGATCAAAAAAA*GAAGTATTA*AAATTACGATC Target; Caenorhabditis elegans
                                       (SEQ ID No. 32)
5'-
TCTTGGATCAAAAAATGAAGTATTTAAATTACGATCAGTTAACAACATAG

TAATAGCCCCTGCTAAAACCGGTAGAGATAAAACCAGTAAAAACACTGTT

ACAAATACAGTTCAAACAAATAAAGTTATATGTTCTAATGAAATAGAACT

TCTACGTAAATTTTTAGTAGTACACATAAAATTAATACCACCTAAGATA

GATCTTAACCCTGCTGCATGTAAACTAAAAATAGCTAAATCTACTCTA

CTTCCAGGGTGCCCCATTGTTCTTAAAGGTGGGTAGACTGTTCACCTAG

TCCCACAACCTATATCTACAAAACAAGCATCTAAAATTAATAATATAGAT

GTAGGTAATAACCAAAATCTTAAATTATTTAAACGTGGAAATCTTATA
```

```
TCAGGTGCTCCTAACATAAGTGGTAATAATCAGTTACCAAAACCACC

GATTATAGTAGGTATTACC

Target; Steinernema feltiae
                                       (SEQ ID No. 33)
5'-
TCTAGGATCAAAAAAAGAAGTATTTAAATTACGGTCTGTAAGAAGTATAG

TAATTGCCCCAGCTAAAACCGGTAAAGAAAGAACAAGAAGGAAAACTGT

AACAAAAACAGTTCAAACAAAAAGACTCATATGCTCTAAAGAAATAGAG

CTTCTACGAAGATTCTTAGTAGTACATATAAAATTAATAGCCCCCAAAA

TAGAGCTTACACCAGCACAATGAAGACTAAAAATAGCTAAATCAACCC

TGTTTCCAGGATGGCCTAAAGTACTTAAAGGAGGATAAACAGTTCAAC

TAGTACCACACCCTGTATCTACAAAACAAGCATCTAAAATTAATAATAT

AGCAGTGGGTAATAACCAAAAACTTAAATTATTTAAACGAGGAAATCTT

ATATCCGGAGCACCAAGAAGGAACTAATCAATTTCCAAATCCTCCNNNN

NNNNNNNN

Probe Sequences;
Probe One (quencher probe for Cal Orange signaling
probe)
                                       (SEQ ID NO. 34)
5'-AA*TATTACCT*T*TG*ATGTTAGGG*GCT*CCTGATATAAGT*T

TT-BHQ1

Probe Two (signaling probe with Cal Orange)
                                       (SEQ ID No. 35)
5'-CalOrg-
ATCCT*CGTTTAAATAATTTAAGT*TTTTGA*TTATTACCTACT*TCAT-

BHQ1

Probe Three (quencher probe for first Cal Red
signaling probe)
                                       (SEQ ID No. 36)
5'-
TT*TG*TTT*TG*T*T*G*TTG*G*GATT*CTTGTTTTGTT*GATATAGG

TG*GTGGAA-BHQ2

Probe Four (first signaling probe with Cal Red)
                                       (SEQ ID No. 37)
5'-CalRed-A*ACTG*GT*TGAACT*GTT*TACCCT*CCTTTAAGAA

CT*T-BHQ2

Probe Five (quencher probe for second Cal Red
signaling probe)
                                       (SEQ ID No. 38)
5'-
AAG*TA*GGT*CAT*CCTGGT*AGTAC*T*GTAGATTTT*GT*TA

TTTTTAC*TT-BHQ2

Probe Six (second signaling probe with Cal Red)
                                       (SEQ ID No. 39)
5'-CalRed-
ATG*CATGG*T*GCT*GGT*TTT*AGT*TCTATT*TTG*GGTGC*TAT-

BHQ2

Probe Seven (quencher probe for first Quasar
signaling probe)
                                       (SEQ ID No. 40)
5'-
ATTAATTTTATGG*GTACTACTG*T*T*AAG*A*A*T*CT*G*C*G

T*AGTTAT-BHQ2
```

-continued

Probe Eight (first signaling probe with Quasar)
(SEQ ID No. 41)
5'-Quasar-TT CTATTTCT*TTG*GAACATATG*AG*TC*TG*TTTG

TTTGG*ACTGAA-BHQ2

Probe Nine (quencher probe for second Quasar
signaling probe)
(SEQ ID No. 42)
5'-TT*TTTGTG*ACT*GTT*TTTTTG*T*TGGTTC*TG*TCTCT*AA-

BHQ2

Probe Ten (second signaling probe with Quasar)
(SEQ ID No. 43)
5'-Quasar-TTCCT*GTTTTAGG*T*GGGGCTATTACTATA*TTGTTA

ACTAA-BHQ2

FIG. 8 shows strand 81, which is the portion of the Excess Primer strand that lies between the primers (not shown) from the amplification of the C elegans target sequence. In FIG. 8, quencher moieties are shown by (●), Quasar fluorophores are shown by (*), Cal Red fluorophores are shown by (★), and the Cal Orange fluorophore is shown by (♦). Oligonucleotides 82, 83, 84, 85, 86, 87, 88, 89, 90 and 91 are Probe Ten through Probe One, respectively.

The DNA of a single nematode was extracted by placing the individual worm into 25 ul volume of a lysis buffer containing 100 ug/ml proteinase K, 10 mM Tris-Cl pH 8.3, and 5 uM SDS (sodium-dodecyl-sulfate); heating to 50° C. for 30 min followed by 95° C. for 10 min; then adding 25 ul of 10 mM Tris-C1 pH 8.3 buffer prior to storage at -20° C.

LATE-PCR amplifications were carried out in 25 ul volume consisting of 1× PCR buffer (Invitrogen, Carlsbad, Calif.), 100 nM of each probe, 3 mM $MgCl_2$, 250 nM dNTPs, 100 nM of each limiting primer, 1000 nM of excess primer, 1.25 units of Platinum Taq DNA polymerase (Invitrogen, Carlsbad, Calif.) and 1 ul of previously extracted nematode DNA with approximately 10,000 mitochondrial genomes. Amplification reactions were run in a triplicate sets.

The thermal profile conditions for these reactions were as follows: 95° C. for 3 min followed by 95° C./5 s-55° C./10 s-72° C./45 s for 5 cycles followed by 95° C./5 s-64° C./10 s-72° C./45 s for 45 cycles followed by a melt starting at 25° C. with 1° C. increments at 30 s intervals to 95° C. followed by an annealing starting at 95° C. with 1° C. decrements at 30 s intervals to 25° C. The instrument used for amplification and anneal analysis was a Bio-Rad IQ5 instrument (Bio-Rad, Hercules, Calif.).

Probe-target hybridizations were analyzed by anneal curve analysis using the first derivative for each fluorophore separately (Cal Orange 560, Cal Red 610 and Quasar 670 from Biosearch Technologies, Novato Calif.) for temperatures between 65° C. to 25° C. The fluorescent value at 65° C. is subtracted from all fluorescent values and thus is zero at 65° C. From this data set the highest fluorescent value is used to normalize the data to one. If the value used was negative, it was multiplied by (-15); if it was a positive number, it was multiplied by fifteen (+15). This generated numerical values that were subsequently used in a 5-bit barcoding format.

Figure 9A:
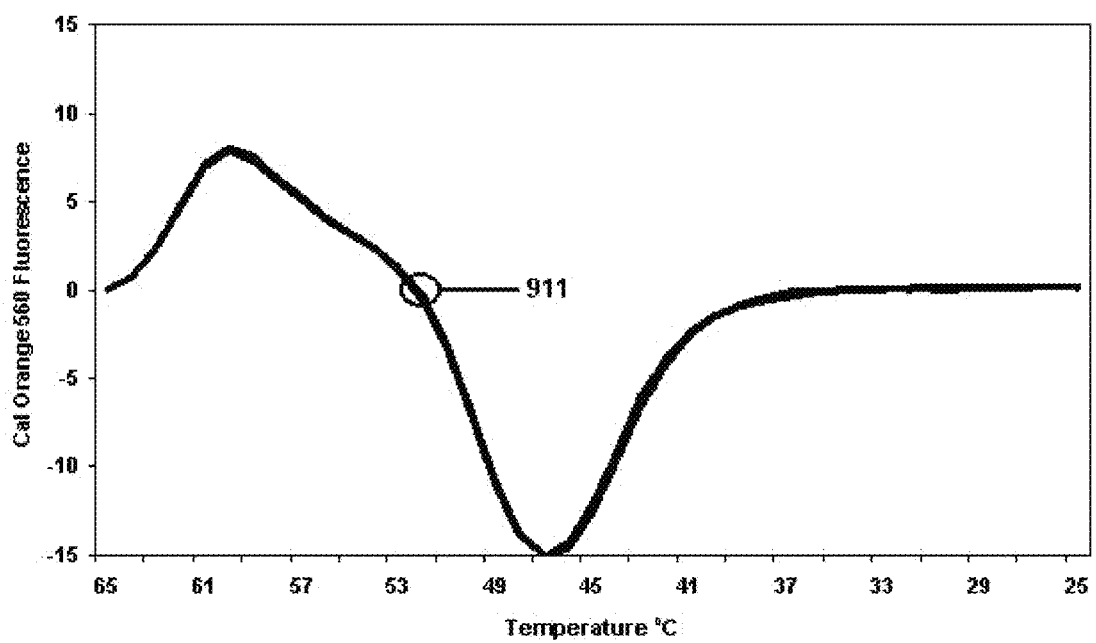
FIGS. 9A-9C are graphs of fluorescence versus temperature for each of the fluorophores in Example 4 against one single-stranded nucleic acid target sequence.
Figure 9B:
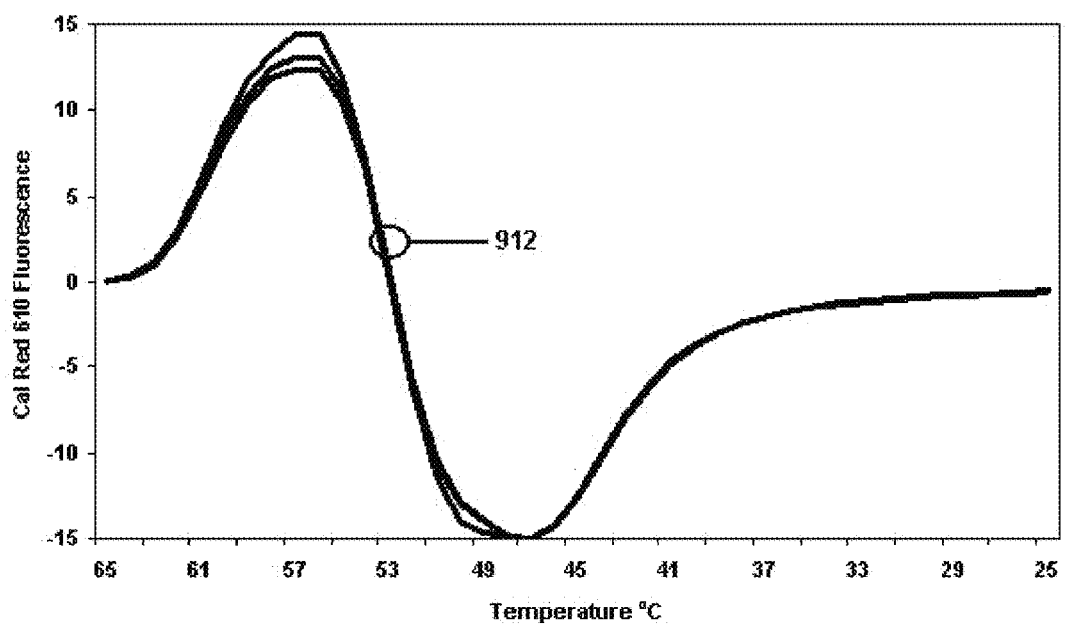
Figure 9C:
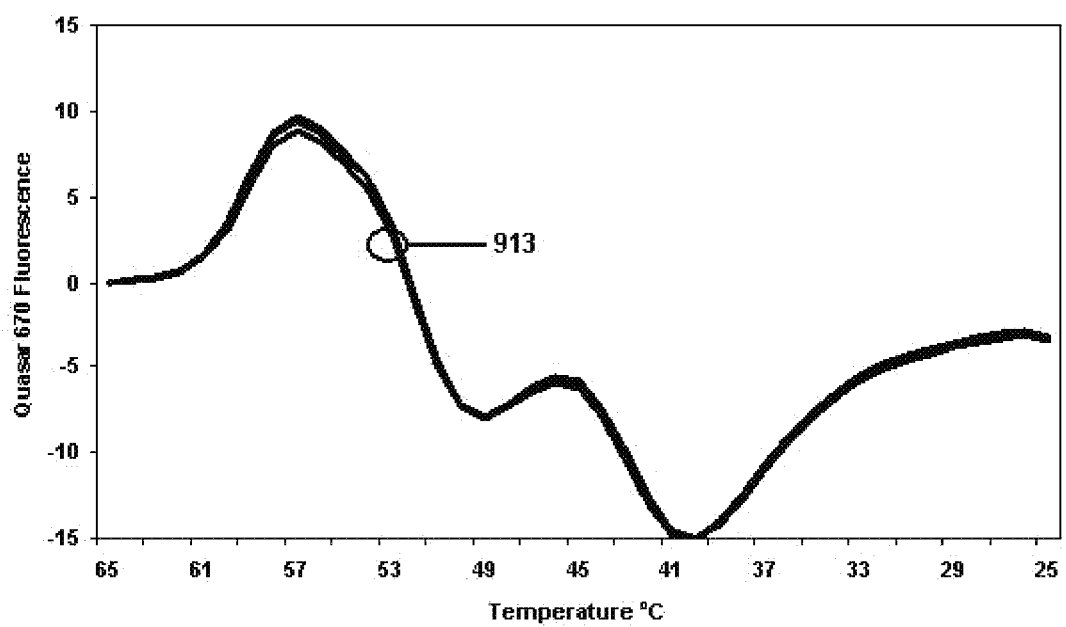

FIGS. 9A-9C present the normalized fluorescence readings for the Cal Orange 560, Cal Red 610, and Quasar 670 probes respectively, of the target Steinernema feltiae as a function of the temperature. FIG. 9A shows the readings from the Cal Orange 560 probes wherein circle 911 represents the three replicate amplification reactions. FIG. 9B shows the readings from the Cal Red 610 probes wherein circle 912 represents the three replicate amplification reactions. FIG. 9C shows the readings from the Quasar 670 probes wherein circle 913 represents the three replicate amplification reactions.

Figure 10A:
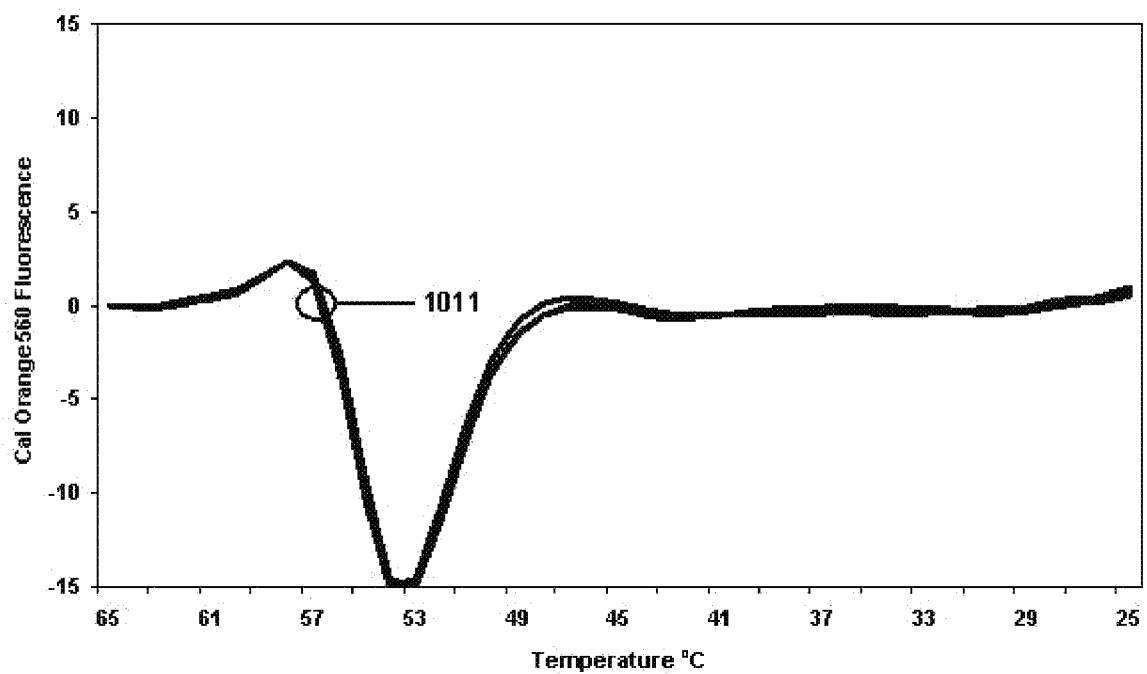
FIGS. 10A-10C are graphs of fluorescence versus temperature for each of the fluorophores in Example 4 against another single-stranded nucleic acid target sequence.
Figure 10B:
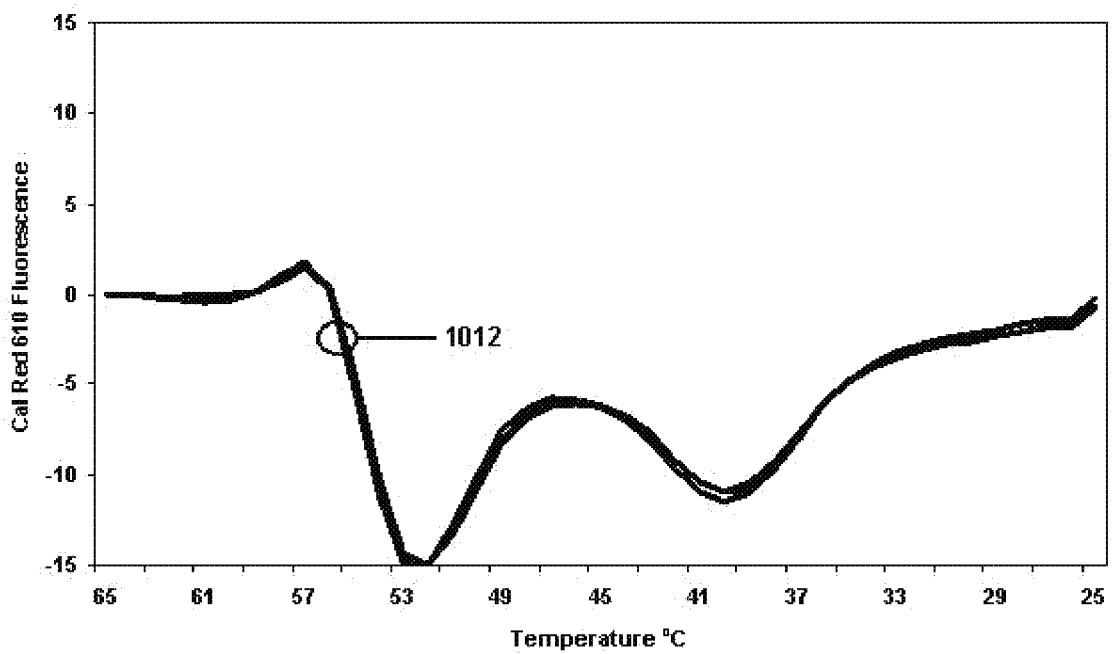
Figure 10C:
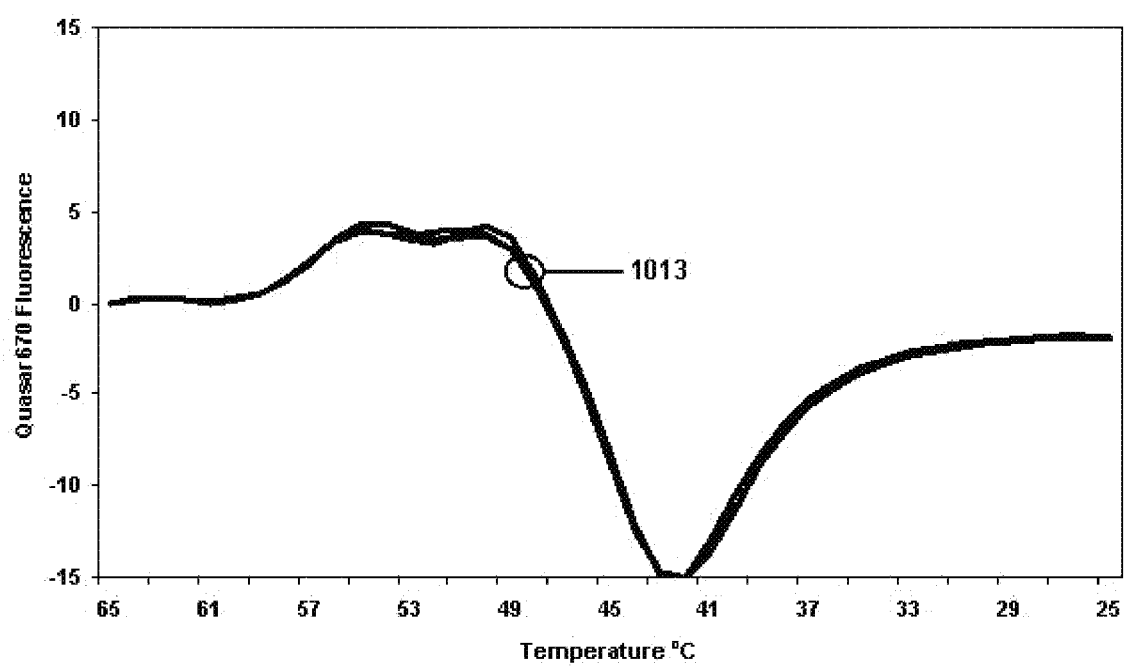
Figure 11A:
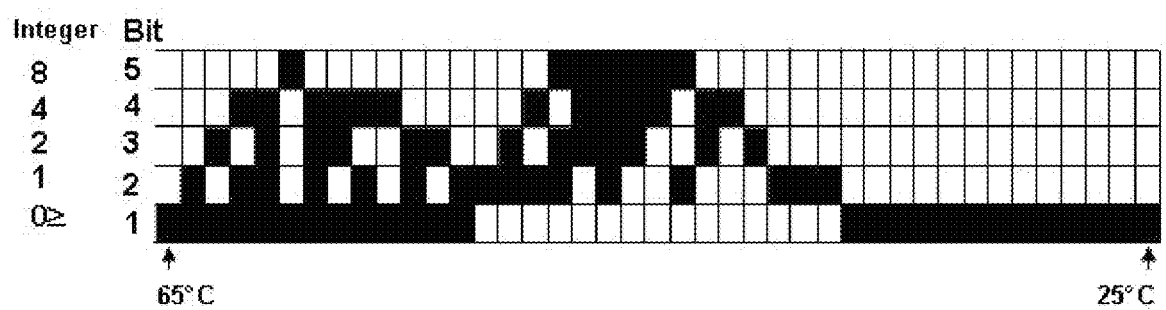
FIGS. 11A-11C are bar codes made from the fluorescence-curve data shown in FIG. 9.
Figure 11B:
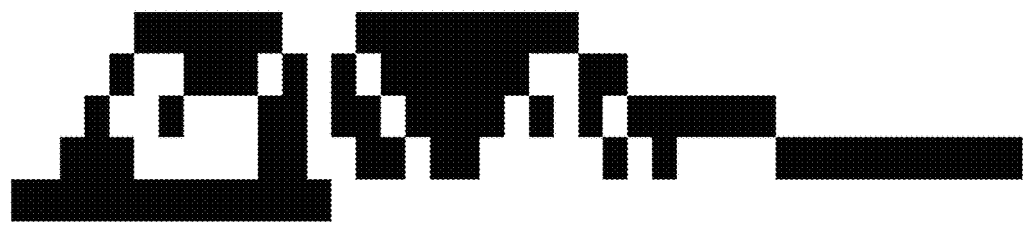
Figure 11C:
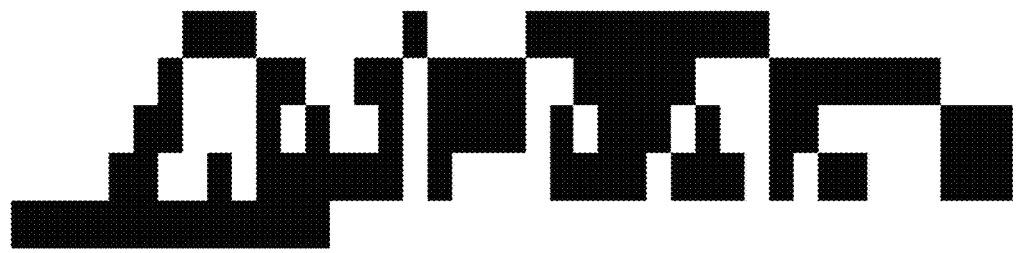

FIGS. 10A-10C present the normalized fluorescence readings for the Cal Orange 560, Cal Red 610, and Quasar 670 probes respectively, of the target Caenorhabditis elegans. FIG. 10A shows the readings from the Cal Orange 560 probes wherein circle 1011 represents the three replicate amplification reactions. FIG. 10B shows the readings from the Cal Red 610 probes wherein circle 1012 represents the three replicate amplification reactions. FIG. 10C shows the readings from the Quasar 670 probes wherein circle 1013 represents the three replicate amplification reactions.

FIGS. 11A-11C show the 5-bit barcoding format that is translated directly from each of the normalized fluorescent values (Cal Orange 560, Cal Red 610, and Quasar 670 respectively) obtained from the anneal analysis of the target Steinernema feltiae. The coding is a 5-bit format that represents the fluorescent values obtained at each one degree decrements in temperature from 65° C. to 25° C. in integer form. For each decrement the first bit is a determination if the value is either greater or equal to zero, which is scored as plus (black color) while values below zero are scored as a minus (no color). The next 4 bits represent the integers 1, 2, 4, and 8 for the fluorescent values obtained by the analysis. For example, if at temperature 45° C. the integer value from the Cal Orange 560 fluorescence is 12, then bit 1 has no color, bits 2 and 3 (representing intergers 1 and 2) have no color, and bits 4 and 5 (representing intergers 4 and 8) are black. FIG. 11A is the fluorescence values obtained from the Cal Orange 560 probes converted into a 5-bit barcode from a single reaction and shows how the barcode is arranged at each temperature with the bits arranged vertically. FIG. 11B is the fluorescence values obtained from the Cal Red 610 probes converted into a 5-bit barcode from a single reaction. FIG. 11C is the fluorescence values obtained from the Quasar 670 probes converted into a barcode from a single reaction.

Example 5

Sepsis Assay

Sepsis may result from infection by any of a number of bacterial species. The assay presented in this example demonstrates the ability to distinguish among species using the analytical methods provided herein with a single-tube, homogeneous LATE-PCR amplification and detection method. A region of the bacterial 16s ribosomal gene was chosen for analysis, because the region is known to have relatively conserved sequences that flank a hypervariable region. A single Limiting Primer and a single Excess Primer complementary to conserved sequences flanking the V3 hypervariable region of the 16s gene wee used.

For a test panel, eleven bacterial species identified in Table 2 were utilized (abbreviations used throughout the remainder of the example are provided in Table 2).

TABLE 2

Bacterial Species Panel

| Bacterial Species | Abbreviation |
| --- | --- |
| Acinetobacter baumannii | AB |
| Acinetobacter sp. | ASP |
| Enterobacter aerogenes | EA |
| Enterobacter cloacae | EC |
| Enterococcus faecalis | ENFS |
| Enterococcus faecium | ENFM |
| Klebsiella pneumoniae | KP |

TABLE 2-continued

Bacterial Species Panel

| Bacterial Species | Abbreviation |
|---|---|
| *Pseudomonas aeruginosa* | PA |
| *Staphylococcus aureus* | COL |
| *Staphylococcus epidermidis* | SE |
| *Staphylococcus haemolyticus* | SH |

The gene sequence to be utilized was selected by examining the sequences of the species in the panel for a sequence that fits the criteria described above and whose variable region includes sufficient differences among the target species and closely related non-target species by means of a BLAST search, a software program that compares sequences to a known library of sequences, comparison in the NCBI Genbank, a known United States national library sequence database. By this method, which is known in the art, a 203 base pair region was selected, namely, nucleotides 325-527, of *Klebsiella pneumoniae*, NCBI Genbank reference number NC_011283 of 16s rRNA. The gene sequence for the above region of *Klebsiella pneumoniae* was downloaded into a computer program for primer and probe design. Visual OMP (DNASoftware, Inc., Ann Arbor, Mich., USA) was used for the assay design software. Using the design software, a primer set and a set of probes comprising four signaling probes (we refer to them for convenience as "ON" probes) and four quencher probes (we refer to them for convenience as "OFF" probes) was designed. To reach a final design of primers and probes, the initial design was treated as prospective. Several of the sequences selected as design sequences were run through another BLAST search to confirm the appropriate homology with the target sequences and to confirm that the primers have sufficient difference from non-target organisms to avoid their amplification/detection. Next one target species of Table 2, *Staphylococcus aureus*, was tested in a separate amplification utilizing bacterial genomic DNA with the primers and with SYBR Green dye for detection using real-time PCR and melt-curve analysis to check for acceptable amplification efficiency as determined by the linearity of threshold cycle ($C_T$) as a function of target concentration and production of a specific amplification product ("amplicon") as measured by melt-curve analysis.

Using the foregoing method, the following primers and probes were designed. It will be noted that each of the signaling, or "ON", probes is a molecular beacon probe having a stem of two nucleotides, with addition of nucleotides that are not complementary to the target sequences as needed (such added nucleotides being bolded for identification). It will be noted also that all of the signaling probes have a Quasar 670 fluorophore (Biosearch Technologies, Novato, Calif., USA) on one end and a Black Hole Quencher 2 ("BHQ2") quencher (Biosearch Technologies) on the other end, whereas all the quencher probes have a Black Hole Quencher 2 but no fluorophore. The stated primer and probe Tm's are the calculated concentration-adjusted melting temperatures used for LATE-PCR.

Primer Pair
Limiting Primer:
(SEQ ID No. 44)
CCAGACTCCTACGGGAGGCAGCAGT, Tm = 74.7

Excess Primer:
(SEQ ID No. 45)
GTATTACCGCGGCTGCTGGCA, Tm = 72.1

Probe "Quasar con 1 off":
(SEQ ID No. 46)
AAGGGGAATATTGCACAATGGTT-BHQ2

Probe "Quasar con 1 on":
(SEQ ID No. 47)
Quasar 670-AAGCGAAAGCCTGATGCAGCCATT-BHQ2

Probe "Quasar con 2 on":
(SEQ ID No. 48)
BHQ2-TAGCCGCGTGTGTGAAGAATA-Quasar 670

Probe "Quasar con 2 off":
(SEQ ID No. 49)
BHQ2-TTGGCCTTCGGATTGTAAAGCACTTAA-C3 Carbon Linker Probe "Quasar 1 off":
(SEQ ID No. 50)
TATTAGTAGGGAGGAAGTA-BHQ2

Probe "Quasar 1 on":
(SEQ ID No. 51)
Quasar 670-TTATATGTGTAAGTAACTGTGCACATCAA-BHQ2

Probe "Quasar 2 off":
(SEQ ID No. 52)
TTGACGTTACCCGCAA-BHQ2

Probe "Quasar 2 on":
(SEQ ID No. 53)
Quasar 670-TTGAAGAAGCACCGGCTAACTCCGAA-BHQ2

The alignment of the primers and probes on the target sequences selected as design sequences is shown in FIG. 12, which presents one strand only of each target sequence. Nucleotide positions are shown in the right-hand column of FIG. 12. Sequences in the column designated 121 correspond to the Limiting Primer, and sequences 130 correspond to the Excess Primer. The location of quencher probe "Quasar con 1 off" is the column of sequences 122. The location of signaling probe "Quasar con 1 on" is sequences 123. The location of signaling probe "Quasar con 2 on" is sequences 124. The location of quencher probe "Quasar con 2 off" is sequences 125. The location of quencher probe "Quasar 1 off" is sequences 126. The location of signaling probe "Quasar 1 on" is sequences 127. The location of quencher probe "Quasar 2 off" is sequences 128. The location of signaling probe "Quasar 2 on" is sequences 129.

The melting temperatures (Tm's) of the quencher probes (300 nM) and loop portions of the signaling probes (100 nM) in the probe set against the various design target sequences (FIG. 12) that are representative of the clinical bacterial species found in sepsis, as predicted by the Visual Omp design program, are shown in Table 3.

TABLE 3

Calculated Probe Melting Temperatures, ° C.

| | PROBE | | | |
|---|---|---|---|---|
| Sequence | Quasar Con1 Off | Quasar Con1 On | Quasar Con 2 On | Quasar Con 2 Off |
| KP | 60.3 | 67.1 | 62.8 | 63.4 |
| EA | 60.3 | 67.1 | 56.1 | 54.2 |
| AB | 50.5 | 51.7 | 62.8 | 44.1 |
| PA | 50.5 | 65.6 | 62.8 | 59.9 |
| COL | 13.1 | 50.2 | 49.6 | 26.8 |
| SE | 2.2 | 50.2 | 49.6 | 26.8 |
| ENFS | 6.4 | 23.8 | 54.0 | 15.2 |

TABLE 3-continued

Calculated Probe Melting Temperatures, ° C.

| | PROBE | | | |
|---|---|---|---|---|
| Sequence | Quasar 1 Off | Quasar 1 On | Quasar 2 Off | Quasar 2 On |
| KP | 35.5 | 13.0 | 54.4 | 65.5 |
| EA | 20.2 | 13.0 | 40.0 | 65.5 |
| AB | 20.2 | 19.5 | 38.1 | 60.5 |
| PA | 36.2 | −7.4 | 39.7 | 57.9 |
| COL | 20.2 | 62.4 | 8.4 | 34.8 |
| SE | 20.2 | 53.4 | 8.4 | 34.8 |
| ENFS | 20.2 | 21.7 | −2.4 | 34.8 |

Twenty-five μL LATE-PCR reaction mixtures including a single bacterial genomic DNA target contained 10×PCR Buffer 1× (final concentration), 10 mM dNTPs 250 μM (final concentration), 50 mM Mg$^{++}$3 mM (final concentration), 10 μM Limiting Primer 50 nM (final concentration), 100 μM Excess Primer 1000 nM (final concentration), 10 μM each signaling probe 100 nM (final concentration), 10 μM of each quencher probe 300 nM (final concentration), 1 Unit Platinum Taq DNA polymerase and 10$^6$ bacterial genomic DNA starting copies. Two controls were also amplified: a probes-only control (NTCP) containing all above reagents except Taq polymerase and genomic DNA, and a Taq polymerase-only control (NTCT) containing Taq polymerase and all of the above reagents but no genomic DNA.

Amplification and detection of three replicate samples of each target and each control were performed with a Bio Rad (Hercules, Calif., USA) IQ5 real-time thermocycler using the following protocol: denaturation at 95° C. for three minutes, followed by 35 cycles of 95° C. for 10 seconds, 69° C. for 15 seconds and 72° C. for 45 seconds. Following amplification a melt curve was generated starting at 25° C. and progressing to 80° C. in one-degree steps of thirty seconds each and then an anneal curve was generated starting at 80° C. and progressing to 25° C. in one degree steps of thirty seconds each, with data acquisition of Quasar 670 fluorescence at each step. The various anneal curves are shown in FIG. 13, a graph of the normalized intensities of Quasar 670 fluorescences versus temperature. Fluorescence intensities were normalized to 75° C. and with background fluorescence of the NTCT control at 75 deg subtracted, and then the highest fluorescent value normalized to 1.0. In FIG. 13, circle 131 is the anneal curves for the NTCP control, circle 132 is the anneal curves for the NTCT control, circle 133 is the anneal curves for target AB, circle 134 is the anneal curves for the target ASP, circle 135 is the anneal curves for the target EA, circle 136 is the anneal curves for target EC, circle 137 is the anneal curves for target ENFS and for target ENFM which should be the same, circle 138 is the anneal curves for target KP, circle 139 is the anneal curves for the target PA, circle 140 is the anneal curves for the target COL, circle 141 is the anneal curves for the target SE, and circle 142 is the anneal curves for the target SH.

FIG. 14 presents the anneal derivative, −dF/dT of the anneal curves. The numbered circles in FIG. 14 identify the derivative curves as follows: circle 151 is the three replicates of the NTCP control; circle 152, for the NTCT control; circle 153, for target AB; circle 154, for target ASP; circle 155, for target EA; circle 156, for target EC; circle 157, for target ENFS and target ENFM that give the same signal; circle 158, for target KP; circle 159, for target PA; circle 160, for target COL; circle 161, for target SE; and circle 162, for target SH.

The fluorescence intensity curves (FIG. 13) or the derivative curves (FIG. 14) can be used as a library. A curve or curves from an unknown sample can be compared to the stored curve or curves to identify the bacterial species that is present. Alternatively or in addition, digitized information from either or both families of curves can be used as a library. For example, for each replicate of each target in FIG. 13, one can create a table of ratios. One such table constructed during development of embodiments of the present invention is the ratio of fluorescence intensity at 25° C. to the intensity at 30° C., the ratio of intensity at 30° C. to the intensity at 35° C. and so on up the temperature scale five degrees at a time. Ratios resulting from an unknown sample can be compared to the library of ratios to identify the species that is present. Alternatively, from FIG. 14 one can prepare a table of temperatures at which maxima and minima occur. Table 4 presents such temperatures for the curves of FIG. 14, where a positive (+) indicator represents the temperature of a maximum and a negative (−) indicator represents the temperature of a minimum. Maxima and minima from an unknown can be compared to Table 4 to identify the species present.

TABLE 4

Maximum and Minimum Temperature Values of Anneal Derivatives

| Bacterium | Temperatures (° C.) of Maxima (+) and Minima (−) |
|---|---|
| AB | (+) 61, (−) 55, (+) 52, (−) 46 |
| ASP | (+) 60, (−) 53 |
| EA | (+) 66, (−) 63, (+) 60, (−) 54, (+) 52, (−) 49 |
| EC | (+) 68, (−) 62, (+) 59, (−) 56 |
| ENFS | (+) 55, (−) 36 |
| ENFM | (+) 55, (−) 36 |
| KP | (+) 68, (−) 63 |
| PA | (+) 65, (−) 61, (+) 58, (−) 52, (+) 47, (−) 41 |
| COL | (+) 61, (−) 55, (+) 50, (−) 43, (+) 37 |
| SE | (+) 50, (−) 43, (+) 37 |
| SH | (+) 49, (−) 43, (+) 37 |

Table 4 shows that the Tms for most of the samples are very different because their 16S rRNA region is highly variable, so even those species of the same genus like EA and EC, and AB and ASP have very different values in Table 4. However for ENFS and ENFM that have the same 16S DNA sequence, the values are the same, as is predicted. Even those targets with as few as two DNA sequence differences, SE and SH, show a different set of values in Table 4, and have significant differences versus COL.

Example 6

Sepsis Assay with More than a Single Bacterial Species Present

In clinical situations more than a single bacterial species may be present and the Sepsis Assay must be able to differentiate between a fluorescent signal pattern generated from a single bacteria species to that from a mixture of two or more species.

Using the same primers and probes, and PCR reagents as in Example 5, except that two bacterial genomic DNA targets are included, FIG. 15 shows the anneal curves after normalization of the raw data to 75° C., the NTCT background subtracted at 75° C., and the highest fluorescent value normalized to 1.0 for different mixtures of two bacteria species, where the starting concentration of one species is held constant while the starting concentration of the second species is varied. Circle 170 are the NTCT; circle 171 are $10^5$ starting copies of only SE; circle 172 are $10^6$ starting copies of only COL; circle 173 are a mixture of $10^6$ starting copies of COL and $10^5$ starting copies of SE; circle 174 are a mixture of $10^5$ starting copies of COL and $10^5$ starting copies of SE, circle 175 are a mixture of $10^4$ starting copies of COL and $10^5$ starting copies of SE.

FIG. 15 shows the resolution of fluorescent signatures for mixtures. A specific fluorescent signature is given for both the pure samples and each of the mixtures. In FIG. 15, mixtures of fluorescent signatures of COL: SE of 1.0:0.0, 1.0:0.9, 1.0:1.0, 0.9:1.0 and 0.0:1.0 are shown. The fluorescence intensity curves (FIG. 15) can be used as a library. An unknown sample can be compared to the stored curve or curves to identify the bacterial specie or mixture of species that are present. Alternatively or in addition, digitized information from families of curves can be used as a library. For example, for each replicate of each target in FIG. 15, one can create a table of ratios. One such table is the ratio of fluorescence intensity at 25° C. to the intensity at 30° C., the ratio of intensity at 30° C. to the intensity at 35° C. and so on up the temperature scale five degrees at a time. Ratios resulting from an unknown sample can be compared to the library of ratios to identify the species or combination of species that is present. From these data it is also evident that mixtures where the minor component is less than 10% of the major component will not be resolved. The library of fluorescent signatures can be developed for all mixtures between relative concentrations of 1.0 to 0.1 of each component taken in 0.1 steps.

Example 7

Sepsis Assay

The gene sequence to be utilized was selected by examining the sequences of the species in the panel shown in Table 2 in Example 5 for a sequence that fits the criteria described above and whose variable region includes sufficient differences among the target species and closely related non-target species by means of a BLAST search, a software program that compares sequences to a known library of sequences, comparison in the NCBI Genbank, a known United States national library sequence database. By this method, a 475 base pair region was selected, namely, nucleotides 321-795, of *Acinetobacter baumannii* (AB), NCBI Genbank reference number NC_010400 of 16s rRNA. The gene sequence (see FIG. 16) for the above region of AB was downloaded into a computer program for primer and probe design. Visual OMP (DNASoftware, Inc., Ann Arbor, Mich., USA) was used for the assay design software. Using the design software, a primer set and a set of probes was designed comprising eight signaling ("ON") probes and eight quencher ("OFF") probes. To reach a final design of primers and probes, the initial design was treated as prospective. Several of the sequences were selected as design sequences, which were run through another BLAST search to confirm the appropriate homology with the target sequences and to confirm that the primers have sufficient difference from non-target organisms to avoid their amplification/detection. Next one target species, AB, was tested in a separate amplification utilizing bacterial genomic DNA with the primers and with SYBR Green dye for detection using real-time PCR and melt-curve analysis to check for acceptable amplification efficiency as determined by the linearity of threshold cycle ($C_T$) as a function of target concentration and production of a specific amplification product ("amplicon") as measured by melt-curve analysis.

Using the foregoing method, the following primers and probes were designed. Each of the signaling, or "ON", probes is a molecular beacon probe having a stem of two nucleotides, with addition of nucleotides that are not complementary to the target sequences as needed (such added nucleotides being bolded in the sequences for identification). Four of the signaling probes have a Cal Red 610 fluorophore (Biosearch Technologies, Novato, Calif., USA) on one end and a Black Hole Quencher 2 ("BHQ2") quencher (Biosearch Technologies) on the other end, and four of the signaling probes have a Quasar 670 fluorophore (Biosearch Technologies, Novato, Calif., USA) on one end and a BHQ2 quencher on the other end. All eight of the quencher probes have a BHQ2 quencher but no fluorophore. The stated primer and probe Tm's are the calculated concentration-adjusted melting temperatures used for LATE-PCR.

```
Primer Pair
Limiting Primer:
                                         (SEQ ID No. 54)
CCAGACTCCTACGGGAGGCAGCAGT, Tm = 74.7

Excess Primer:
                                         (SEQ ID No. 55)
TGGACTACCAGGGTATCTAATCCTGTTTG, Tm = 69.2

Probe "Cal Red 5 off":
                                         (SEQ ID No. 56)
ATAGGGTGCGAGCGTTAATCT-BHQ2

Probe "Cal Red 5 on":
                                         (SEQ ID No. 57)
Cal Red 610-AAGGATTTACTGGGCGTAAAGCGTT-
BHQ2

Probe "Cal Red 6 off":
                                         (SEQ ID No. 58)
TTGCGTAGGCGGCTTATTAAGTAA-BHQ2

Probe "Cal Red 6on":
                                         (SEQ ID No. 59)
Cal Red 610-AACGGATGTGAAATCCCCGAGCTT-BHQ2

Probe "Cal Red 7off":
                                         (SEQ ID No. 60)
TAACTTGGGAATTGCATTCGTA-BHQ2

Probe "Cal Red 7on":
                                         (SEQ ID No. 61)
Cal Red 610-ATACTGGTGAGCTAGAGTATGAT-BHQ2

Probe "Cal Red 8off":
                                         (SEQ ID No. 62)
GAAGAGGATGGTAGAATTCC-BHQ2

Probe "Cal Red 8on":
                                         (SEQ ID No. 63)
Cal Red 610-TAGGTGTAGCGGTGAAATGCGTA-BHQ2

Probe "Quasar con 1 off":
                                         (SEQ ID No. 64)
AAGGGGAATATTGCACAATGGTT-BHQ2

Probe "Quasar con 1 on":
                                         (SEQ ID No. 65)
Quasar 670-AAGCGAAAGCCTGATGCAGCCATT-BHQ2

Probe "Quasar con 2 on":
                                         (SEQ ID No. 66)
BHQ2-TAGCCGCGTGTGTGAAGAATA-Quasar 670
```

-continued

Probe "Quasar con 2 off":
(SEQ ID No. 67)
BHQ2-TTGGCCTTCGGATTGTAAAGCACTTAA-C3 Carbon Linker Probe "Quasar 1 off":
(SEQ ID No. 68)
TATTAGTAGGGAGGAAGTA-BHQ2

Probe "Quasar 1 on":
(SEQ ID No. 69)
Quasar 670-TTATATGTGTAAGTAACTGTGCACATCAA-BHQ2

Probe "Quasar 2 off":
(SEQ ID No. 70)
TTGACGTTACCCGCAA-BHQ2

Probe "Quasar 2 on":
(SEQ ID No. 71)
Quasar 670-TTGAAGAAGCACCGGCTAACTCCGAA-BHQ2

The alignment of the primers and probes on the target sequences selected as design sequences is shown in FIG. 16, which presents one strand only of the AB target sequence. Nucleotide positions are shown in the left-hand column of FIG. 16. Sequence 176 corresponds to the Limiting Primer, and sequence 193 corresponds to the reverse compliments of the Excess Primer. The location of quencher probe "Quasar con 1 off" is sequence 177. The location of signaling probe "Quasar con 1 on" is sequence 178. The location of signaling probe "Quasar con 2 on" is sequence 179. The location of quencher probe "Quasar con 2 off" is sequence 180. The location of quencher probe "Quasar 1 off" is sequence 181. The location of signaling probe "Quasar 1 on" is sequence 182. The location of quencher probe "Quasar 2 off" is sequence 183. The location of signaling probe "Quasar 2 on" is sequence 184. The location of quencher probe "Cal Red 5 off" is sequence 185. The location of signaling probe "Cal Red 5 on" is sequence 186. The location of quencher probe "Cal Red 6 off" is sequence 187. The location of signaling probe "Cal Red 6 on" is sequence 188. The location of quencher probe "Cal Red 7 off" is sequence 189. The location of signaling probe "Cal Red 7 on" is sequence 190. The location of quencher probe "Cal Red 8 off" is sequence 191. The location of signaling probe "Cal Red 8 on" is sequence 192.

The melting temperatures (Tm's) of the quencher probes (300 nM) and loop portions of the signaling probes (100 nM) in the probe set against the various design target sequences (FIG. 16) that are representative of the clinical bacterial species found in sepsis, as predicted by the Visual Omp design program, are shown in Table 5

TABLE 5

Calculated Probe Melting Temperatures, ° C.

| | PROBE | | | |
|---|---|---|---|---|
| Sequence | Quasar Con1 Off | Quasar Con1 On | Quasar Con 2 On | Quasar Con 2 Off |
| KP | 60.3 | 67.1 | 62.8 | 63.4 |
| EA | 60.3 | 67.1 | 56.1 | 54.2 |
| AB | 50.5 | 51.7 | 62.8 | 44.1 |
| PA | 50.5 | 65.6 | 62.8 | 59.9 |
| COL | 13.1 | 50.2 | 49.6 | 26.8 |
| SE | 2.2 | 50.2 | 49.6 | 26.8 |
| ENFS | 6.4 | 23.8 | 54.0 | 15.2 |

TABLE 5-continued

Calculated Probe Melting Temperatures, ° C.

| | PROBE | | | |
|---|---|---|---|---|
| Sequence | Quasar 1 Off | Quasar 1 On | Quasar 2 Off | Quasar 2 On |
| KP | 35.5 | 13.0 | 54.4 | 65.5 |
| EA | 20.2 | 13.0 | 40.0 | 65.5 |
| AB | 20.2 | 19.5 | 38.1 | 60.5 |
| PA | 36.2 | −7.4 | 39.7 | 57.9 |
| COL | 20.2 | 62.4 | 8.4 | 34.8 |
| SE | 20.2 | 53.4 | 8.4 | 34.8 |
| ENFS | 20.2 | 21.7 | −2.4 | 34.8 |

| | PROBE | | | |
|---|---|---|---|---|
| Sequence | Cal Red 5 Off | Cal Red 5 On | Cal Red 6 Off | Cal Red 6 On |
| KP | 56.6 | 60.5 | 46 | 64.2 |
| EA | 56.6 | 60.5 | 46 | 64.2 |
| AB | 62.6 | 64.4 | 65.2 | 69.5 |
| PA | 56.4 | 60.5 | 32.7 | 60.4 |
| COL | 26.8 | 55.6 | 52.5 | 8.7 |
| SE | 29.4 | 55.6 | 52.5 | 8.7 |
| ENFS | 37.2 | 55.4 | 49.4 | 41.7 |

| | PROBE | | | |
|---|---|---|---|---|
| Sequence | Cal Red 7 Off | Cal Red 7 On | Cal Red 8 Off | Cal Red 8 On |
| KP | 48.2 | 24.7 | 37.2 | 67.1 |
| EA | 48.2 | 24.7 | 37.2 | 67.1 |
| AB | 59.1 | 59.4 | 55.9 | 67.1 |
| PA | 36.1 | 37.2 | 15.7 | 64 |
| COL | −5.2 | 12.8 | 23.1 | 63.6 |
| SE | −5.2 | 12.8 | 23.1 | 63.6 |
| ENFS | −3.1 | 12.8 | 15.5 | 64 |

Twenty-five µL LATE-PCR reaction mixtures including a single bacterial genomic DNA target contained 10×PCR Buffer 1× (final concentration), 10 mM dNTPs 250 µM (final concentration), 50 mM Mg$^{++}$3 mM (final concentration), 10 µM Limiting Primer 50 nM (final concentration), 100 µM Excess Primer 1000 nM (final concentration), 10 µM each signaling probe 100 nM (final concentration), 10 µM of each quencher probe 300 nM (final concentration), 1 Unit GE puRe Taq DNA polymerase, 0.5 bead, and 10$^6$ bacterial genomic DNA starting copies. A Taq polymerase-only control (NTC) containing Taq polymerase and all of the above reagents but no genomic DNA was also amplified.

Figure 17A:
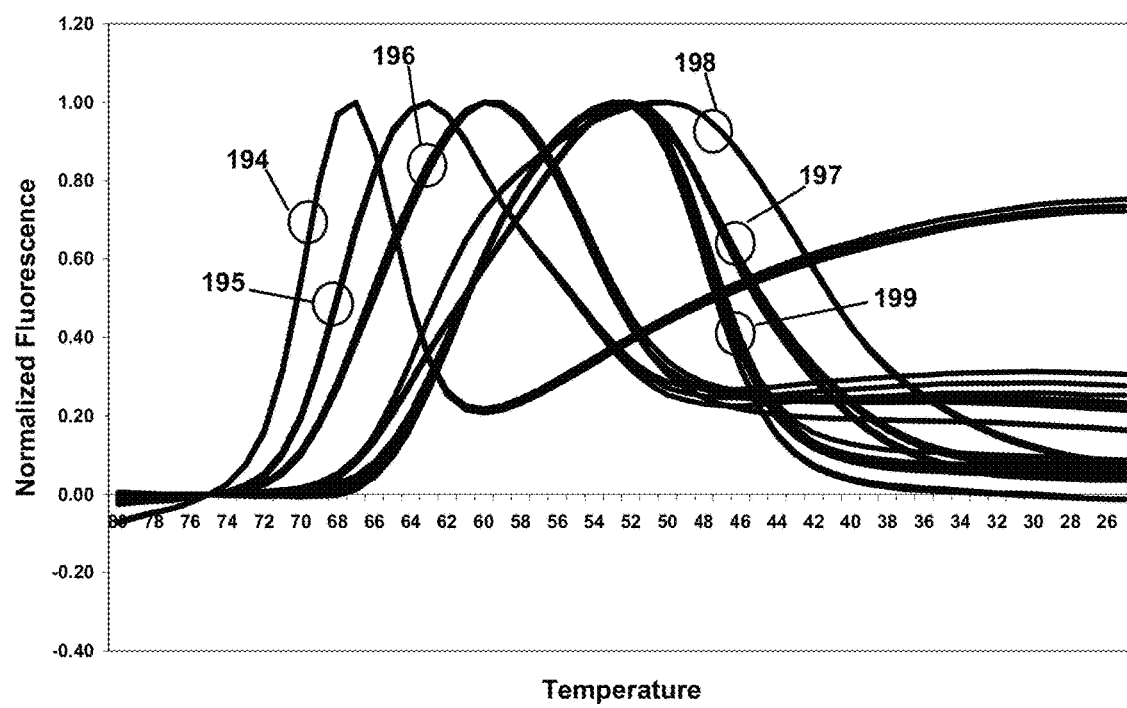
FIG. 17A is a graph presenting annealing curves of the Cal Red 610 fluorophore following amplification of different target species in Example 7.
Figure 17B:
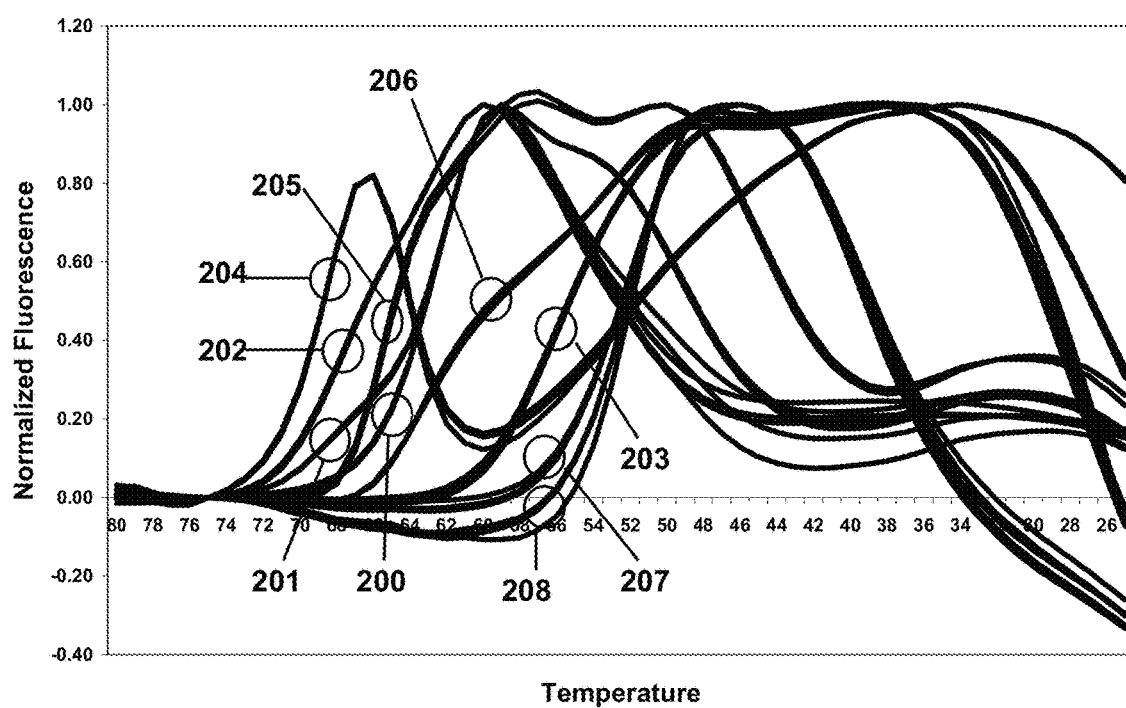
FIG. 17B is a graph presenting annealing curves of the Quasar 670 fluorophore following amplification of different target species in Example 7.

Amplification and detection of three replicate samples of each target and each control were performed with a Bio Rad (Hercules, Calif., USA) IQ5 real-time thermocycler using the following protocol: denaturation at 95° C. for three minutes, followed by 50 cycles of 95° C. for 10 seconds, 65° C. for 15 seconds and 72° C. for 45 seconds. Following amplification a melt curve was generated starting at 25° C. and progressing to 80° C. in one-degree steps of thirty seconds each and then an anneal curve was generated starting at 80° C. and progressing to 25° C. in one degree steps of thirty seconds each, with data acquisition of Cal Red 610 and Quasar 670 fluorescence at each step. The various anneal curves are shown in FIG. 17A, a graph of the normalized intensities of Cal Red 610 fluorescence versus temperature, and FIG. 17B, a graph of the normalized intensities of Quasar 670 fluorescence versus temperature. Fluorescence intensities were normalized to 75° C. and with background fluorescence of the NTC control at 75 deg subtracted, and then the highest fluorescent value normalized to 1.0. In FIG. 17A, circle 194 is the anneal curves for target AB, circle 195 is the anneal curves for the target ASP, circle 196 is the anneal curves for the target EA and for target KP which should be the same, circle 197 is the anneal curves for target ENFS and for target ENFM which should be the same, circle 198 is the anneal curves for the target PA, circle 199 is the anneal curves for the target COL, for the target SE, and for the target SH which should be the same. In FIG. 17B, circle 200 is the anneal curves for target AB, circle 201 is the anneal curves for the target ASP, circle 202 is the anneal curves for the target EA, circle 203 is the anneal curves for target ENFS and for target ENFM which should be the same, circle 204 is the anneal curves for target KP, circle 205 is the anneal curves for the target PA, circle 206 is the anneal curves for the target COL, circle 207 is the anneal curves for the target SE, and circle 208 is the anneal curves for the target SH.

One could analyze the data in FIGS. 17A and 17B by preparing derivative curves and comparing maximum and minimum temperature values, as described in example 5 and shown in Table 4.

Example 8

Further Analysis of the Experiment of Example 4

Using the sequence information presented in Example 4 and a computer program known as VISUAL OMP version 7.2.0.0 the effective melting temperature was determined for the two Cal Red signaling probes and their associated quencher probes to their *C. elegans* target sequences. The results were as follows:
Probe 3 (OFF): 51.7° C.,
Probe 4 (ON): 53.3° C.,
Probe 5 (OFF): 41.2° C.,
Probe 6 (ON): 26.3° C.

Probe 3 and Probe 4 together comprise a set (or pair) of interacting probes, and Probe 5 and Probe 6 together comprise a separate set (or pair) of interacting probes. The difference in the melting temperatures of Probe 3 and Probe 4 is =(+)1.6° C., while the difference in the melting temperatures of Probe 5 and Probe 6 is =(−) 15.9° C. In the Probe 3/Probe 4 set the signaling probe has the higher calculated melting temperature, whereas in the Probe 5/Probe 6 set the quencher probe has the higher calculated melting temperature.

FIG. 10B presents the normalized derivative curve of fluorescence readings for Cal Red 610 probes of the target *Caenorhabditis elegans*, wherein circle 1012 represents the three replicate amplification reactions. The conditions, the target and experimental details for the data in FIG. 10B are described in Example 4. FIG. 18, circle 218, identifies the temperature-dependent composite fluorescent signals of the anneal curves in this reaction. These data were used to generate the temperature-dependent first derivative curves shown in FIG. 10B. FIG. 18, circle 219, identifies the temperature-dependent composite fluorescent signals of Probes 3-6 in the absence of a template for amplification. Comparison of the fluorescent signals in FIG. 18 reveals that the signal in the presence of amplified target (circle 218) has a higher value than the signal in the absence of target (signal 219) in the range of 53° C., it has a lower value at temperatures approximately between 52 and 25° C.

When the melting temperature of a quencher probe is higher than the melting temperature of the signaling probe, as the temperature is decreased, binding of the signaling probe to the target is detected as a decrease in fluorescence. In order to maximize the decrease in fluorescence due to binding of a signaling probe, the concentration of quencher probe molecules should at least equal, and preferably exceed, the concentration of signaling probe molecules, and the melting temperature of the quencher probe to the target (any target of known sequence) should preferably at least 5° C. greater, and most preferably at least 10° C. greater, than the melting temperature of the signaling probe. Under these conditions the magnitude of the temperature-dependent decrease in fluorescence will depend on the concentration of target molecules present in the reaction, as illustrated in FIG. 19.

Figure 19:
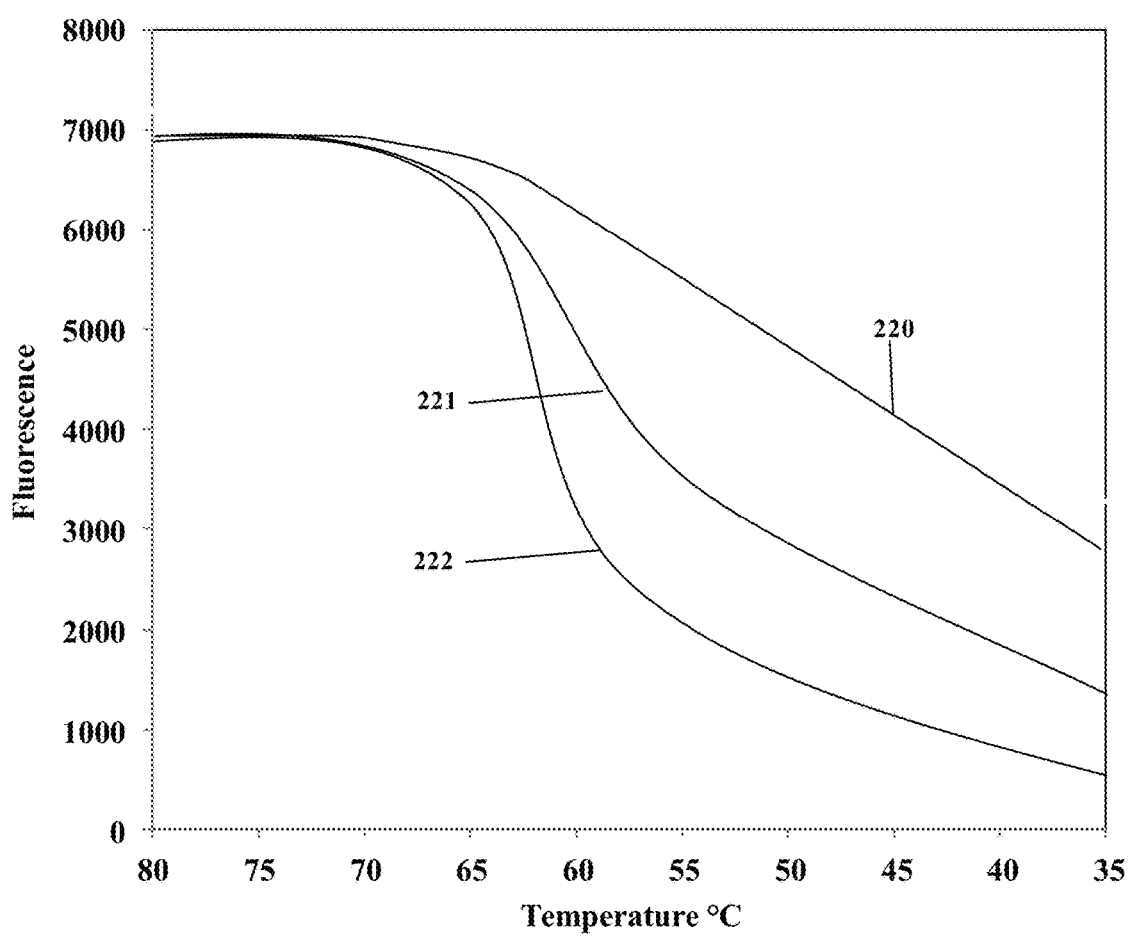
FIG. 19 is an illustrative graph showing how an annealing curve (Fluorescence versus temperature) of a reaction such as described in Example 4 shifts with increasing concentration of target molecules.

When no target molecules are present in the reaction, FIG. 19, line 220, the extent of the temperature-dependent decrease in fluorescence in the system will depend on the chemical composition of the signaling probe oligonucleotide, including: 1) its length; 2) the nature of the covalently linked fluorescent moiety; 3) the presence or absence of a quencher moiety on the oligonucleotide; 4) the nature of an covalently linked fluorescent moiety. The temperature-dependent decrease in fluorescence will reach a maximum when the concentration of target molecules present in the reaction exceeds the concentration of signaling molecules present in the reaction, illustrated in FIG. 19 by line 222, provided the concentration of target molecules does not exceed the concentration of quencher molecules. What will be seen at intermediate concentrations of target molecules is illustrated in FIG. 19 by line 221: the magnitude of the decrease in fluorescence will be intermediate the maximum possible fluorescence, FIG. 19, line 222, and the minimum possible fluorescence, FIG. 19 line 220. By knowing the concentration of signaling probes present in a reaction, a person skilled in the art could use this approach to establish the concentration of target molecules present in a reaction at any time, including: a) in the presence of absence of target amplification; b) during target amplification; and/or c) after target amplification.

Example 9

SNP Genotyping

This example illustrates the use of probes for genotyping of the single nucleotide polymorphism (SNP) rs373129 located in the human tumor suppressor gene CDKN2A.

The segment of genomic DNA containing the SNP site to be genotyped was amplified using LATE-PCR. The probes were designed to hybridize at temperatures 10° C. below the melting temperature of the limiting primer used for LATE-PCR amplification. Tm calculations were performed using the Visual OMP software from DNA software (Ann Arbor, Mich.). The OFF probe consisted of a linear probe labeled at the 3' end with a Black Hole Quencher 2 (BHQ2), Biosearch Technologies, Inc., Novato Calif. This probe was designed to be fully matched to one of the SNP alleles and mismatched to the other allele such that calculated melting temperature of the OFF probe hybridized to the matched T SNP allele target is about 52° C. at 500 nM, assuming a 150 nM target concentration; and the melting temperature of the OFF probe hybridized to the mismatched C SNP allele target is about 41° C. at 500 nM, assuming the same target concentration. The ON probe consisted of a linear probe labeled at the 5' end with a Quasar 670 fluorophore and at the 3' end with a BHQ2 quencher. This probe was designed to have a melting temperature of 62° C. and to hybridize adjacent to the OFF probe binding site such that upon binding to the PCR product, the fluorophore moiety of the ON probe resides next the BHQ2 quencher from the OFF probe. Reaction components and conditions were as follows:

```
Limiting Primer:
                                      (SEQ ID No. 72)
5' GTGAAGGGATTACAAGGCGTGAGGCAC 3', Tm = 71.2

Excess Primer:
                                      (SEQ ID No. 73)
5' GGACTACTTAGCCTCCAATTCAC Tm - 66.2

ON Probe:
                                      (SEQ ID No. 74)
QUASAR 670-5' CGATATTTATTCCAACATACACCGTG 3' BHQ 2, Tm = 62.5

OFF Probe:
                                      (SEQ ID No. 75)
5' CCGATCAAAATTTATATT 3' BHQ 2, Tm = 51.6
(the underlined nucleotide corresponds to the SNP
position)

PrimeSafe 060:
                                      (SEQ ID No. 76)
5'-DABCYL-CGCGGCGTCAGGCATATAGGATACCGGGAC

AGACGCCG CG-DABCYL-3'

PrimeSafe 002:
                                      (SEQ ID No. 77)
5'-DABCYL-CGTAATTATAAT-C3spacer-ATTATAATTACG

DABCYL-3'
```

Primesafe (Rice et al. Nat Protoc. 2007; 2(10):2429-38., herein incorporated by reference in its entirety), is a PCR additive that maintains the fidelity of amplification over a broad range of target concentrations by suppressing mispriming throughout the reaction.

Methods: Genomic DNAs of known genotypes for the rs3731239 SNP site (C/T alleles) were obtained from the Coriell Cell Repository (Camden, N.J.; DNA sample NA10860—homozygous TT alleles; DNA sample NA 10854—heterozygous CT alleles; DNA sample NA07348 homozygous CC alleles). LATE-PCR amplification, in triplicate, of the genomic DNA segment containing the above SNP site from each of the above DNA samples was done in a 25 µl reaction consisting of 1×PCR buffer (Invitrogen, Carlsbad, Calif.), 3 mM MgCl$_2$, 250 nM dNTP, 1 µl M excess primer, 50 nM limiting primer, 500 nM OFF probe, 200 nM ON probe, 1.25 units Platinum Taq DNA polymerase (Invitrogen, Carlsbad, Calif.) and 1000 genomes equivalent of genomic DNA (6 ng). For this experiment the amplification reactions were optimized by including in the reaction mixture a combination of reagents intended to avoid mispriming and to reduce scatter among replicate samples. In this experiment, reagents for reducing mispriming and improving reproducibility were included, according to issued U.S. Pat. No. 7,517,977 and corresponding international patent application WO 2006/044995. The reaction mixture included 25 nM PrimeSafe 060 and 300 nM PrimeSafe 002. A control reaction consisted of no template controls (NTC samples).

LATE-PCR amplification was carried out in a Biorad IQ5 Real-Time PCR Detection System. The amplification conditions were 95° C. for 3 minutes, then 70 cycles of 95° C. for 10 seconds, 64° C. for 10 seconds, 72° C. for 20 seconds. The reaction temperature was then brought to 30° C. at a rate of 1° C./min. Fluorescent signals were collected at every 1° C. as each sample was next heated at a rate of 1° C. per 30 seconds from 30° C. to 80° C.

Raw fluorescent signals collected from each amplification reaction at every temperature were exported to Microsoft Excel. The fluorescent signals for any given melting curve were then normalized as follows: (a) the fluorescent signals at each temperature were first normalized for background fluorescence by dividing the fluorescent signal value at each temperature by the fluorescent signal value at 66° C. (a temperature at which the ON probe is not bound to its target); (b) the resulting fluorescent signal value at each temperature was then subtracted from the average fluorescent signal value from the NTC samples at that temperature; and (c) the resulting fluorescent signal values were then normalized to the fluorescent signal value at the temperature at which the ON probe is bound to the totality of PCR products (58° C.) and then normalized to the fluorescent signal value at the temperature at which the OFF probe is bound to the totality of PCR products and signals from the ON probe are turned off (38° C.). The latter was accomplished by sequentially dividing each fluorescent signal value by the fluorescent signal values at those two temperatures. FIG. 20 shows the resulting normalized fluorescent pattern (fluorescence versus temperature) for the three genotypes. Circle 223 identifies the samples that were homozygous for the matched allele; circle 224 identifies the samples that were heterozygous; and circle 225 identifies the samples that were homozygous for the mismatched allele. Each genotype generated a characteristic fluorescent signature. In FIG. 20 the temperature of 49° C. is the temperature at which the normalized fluorescence signals from the three genotypes exhibited the greatest difference. Values at that single temperature were judged to be statistically adequate to distinguish DNA samples homozygous and heterozygous for the rs3731239 SNP site.

Figure 21:
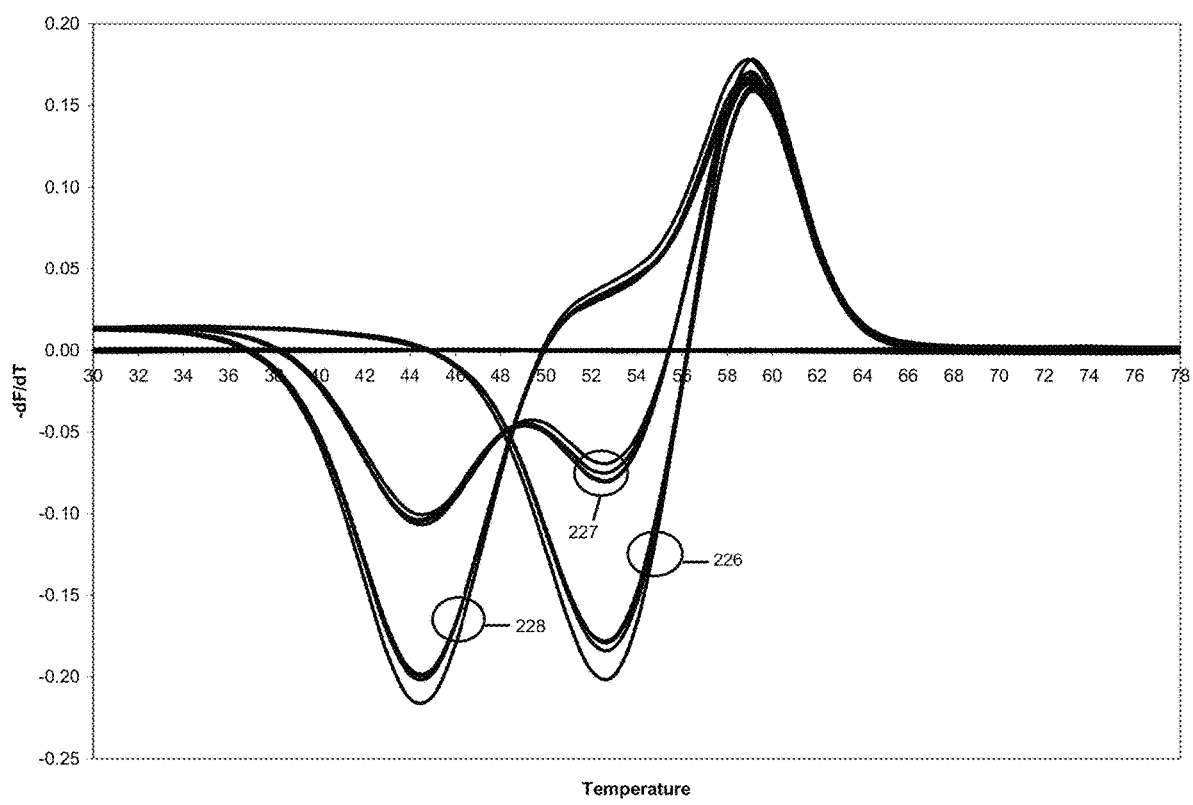
FIG. 21 is a graph presenting the first derivative (−dF/dT) curves of the melting curves of FIG. 20.

FIG. 21 presents the first derivative of the fluorescent patterns of FIG. 20. Circle 226 identifies the samples that were homozygous for the matched alleles; circle 227 identifies the samples that were heterozygous, and circle 228 identifies the samples that were homozygous for the mismatched allele. Positive first derivative values illustrate the binding of the ON probe, which is the same for all genotypes. Negative first derivative values illustrate the allele-specific binding of the OFF probe. Thus, curves 226 for the homozygous samples containing the matched allele show a single negative peak of high Tm; curves 228 for the homozygous samples containing the mismatched alleles show a single negative peak of lower Tm; and curves 227 for the heterozygous samples containing both alleles show two negative peaks corresponding to the negative peaks the matched and mismatched SNP alleles.

Example 10

SPA Typing of MRSA Samples

Recently, DNA sequencing of the polymorphic X, or short sequence repeat (SSR), region of the protein A gene (spa) has been proposed for the typing of S. aureus. The polymorphic X region consists of a variable number of 24-bp repeats and is located immediately upstream of the region encoding the C-terminal cell wall attachment sequence. The existence of well-conserved regions flanking the X region coding sequence in spa allows the use of primers for PCR amplification and direct sequence typing. This example describes the use of a LATE-PCR assay using ON/OFF probes to distinguish strains of S. aureus based on the X repeat region and to create a signature library where different strains can be identified. The assay of this example was designed and tested using a panel of twelve sequenced MRSA samples. The sequence analysis of the samples is given in Table 6.

TABLE 6

MRSA Sample Sequences

| Species type | spa repeat sequence* |
|---|---|
| COL I | YHGFMBQBLO (SEQ ID No. 78) |
| N315 II | TJMBMDMGMK (SEQ ID No. 79) |
| 85/2082 III | WGKAOMQ (SEQ ID No. 80) |
| CA05 IVA | A2AKEMBKB (SEQ ID No. 81) |
| 8/6-3P IVB | YHGFMBQBLO (SEQ ID No. 82) |
| Q2314 IVC | TJMBMDMGGMK (SEQ ID No. 83) |
| JCSC4469 IVD | TJMBMDMGMK (SEQ ID N. 84) |
| AR43/3330.1 IVE | YMBQBLO (SEQ ID No. 85) |
| HAR22 IVH | TJEJNF2MNF2MOMOKR (SEQ ID No. 86) |
| WIS V | A2AKBEKBKB (SEQ ID No. 87) |
| HDE288 VI | TJMBDMGMK (SEQ ID No. 88) |
| BK20781 VIII | YHGFC2BQBLO (SEQ ID No. 89) |

*To make the notation shorter in the table, letter codes ending with "1" in the standard nomenclature have been simplified by omitting this numeral.

The DNA target to be utilized for designing the assay was selected by examining the sequences of the species in the panel shown in Table 6 and in NCBI Genbank for a sequence that fits the criteria described above and whose variable region includes sufficient differences among the target species. By this method, a 507 base pair region was selected, namely, nucleotides 262-768, of the spa gene of *S. aureus*, MRSA252, NCBI Genbank reference number NC_002952. The gene sequence for the above region of MRSA252 were downloaded into a computer program for primer and probe design. Visual OMP (DNASoftware, Inc., Ann Arbor, Mich., USA) was used for the assay design software. Using the design software, a primer set and a set of probes was designed comprising one signaling ("ON") probe and one quencher ("OFF") probe. Nucleic acid sequences for the repeat codes were obtained from Shopsin et al., J. Clinical Microbiology, November 1999, pages 3556-3563. For alignment of potential probe sequences to various repeat sequences, reverse complements of repeat sequences obtained from that paper were used.

To reach a final design of primers and probes, the initial design was treated as prospective. Several of the sequences were selected as design sequences, which were run through another alignment to confirm the appropriate homology with the target sequence.

Using the foregoing method, a pair of primers was designed, which bracket the target sequence, and a pair of probes. The sequences of the primers and probes, plus the MRSA 252 target sequence, are given below. The excess primer is a consensus primer. For this example two probes were used: an ON probe that has a consensus sequence that matches the largest number of bases (19 of 24) in the possible repeat segments shown in Shopsin et al. and an OFF probe with a consensus sequence that matches the next largest number of bases (15 of 24) in the possible repeat sequences shown in Shopsin et al. The probes will compete hybridize adjacently to one another and result in a signature in an anneal curve done after the amplification. The anneal signature can then be compared to a library of signatures and their respective strain of *S. aureus*.

Each of the signaling, or "ON", probes is a molecular beacon probe having a stem of two nucleotides, with addition of nucleotides that are not complementary to the target sequences as needed (such added nucleotides being bolded in the sequences for identification). The signaling probe has a Quasar 670 fluorophore (Biosearch Technologies, Novato, Calif., USA) on one end and a BHQ2 quencher on the other end. The one quencher probe has a BHQ2 quencher but no fluorophore. The stated primer and probe Tm's are the calculated concentration-adjusted melting temperatures used for LATE-PCR. The probe Tm's are Tm's against perfectly complementary sequences.

Limiting Primer:
(SEQ ID No. 90)
5'-CTGTATCACCAGGTTTAACGACATGTACTCCGT, Tm = 71.0

Excess Primer:
(SEQ ID No. 91)
5'-GCTAAATGATGCTCAAGCACCAA, Tm = 67.2

Target 507, 262-768 (MRSA 252):
(SEQ ID No. 92)
5'-
CTGTATCACCAGGTTTAACGACATGTACTCCGTTGCCGTCTTCTTTACC

AGGCTTGTTGCCATCTTCTTTACCAGGCTTGTTGCCATCTTCTTTACCAG

GCTTGTT

GCCATCTTCTTTACCAGGCTTGTTGCCGTCTTCTTTACCAGGTTTGTTG

CCATC

TTCTTTGCCAGGTTTTTTGTTGTCTTCTTTACCAGGTTTGTTGCCGTCTT

CTTTGCCAGGTTTTTTGTTGTCTTCTTTACCAGGTTTGTTGCCGTCTTCT

TTACCAGGCTTGTTGTTGTCTTCTTTGCCAGGCTTGTTGTTGTCTTCCTC

TTTTGGTGCTTGA

GCATCGTTTAGCTTTTTAGCTTCTGCTAAAATTTCTTTGCTCACTGAAG

GATCGTCTTTAAGGCTTTGGATGAAGCCGTTACGTTGTTCTTCAGTTAA

GTTAGGTAAATGTAAAATTTCATAGAAAGCATTTTGTTGTTCTTTGTTGA

ATTTGTTGTCAGCTTTTGGTGCTTGTGCATCATTTAGC spa ON Probe:
(SEQ ID No. 93)
5'-Quasar 670-AACCAGGCTTGTTGTTGTCTTCTTT-BHQ2, Tm = 66.6 spa Off Probe:
(SEQ ID No. 94)
5'-AAGCCAGGTTTTTTGCCATCTTCTTT-BHQ2, Tm = 59.8

Twenty-five µL LATE-PCR reaction mixtures including a single bacterial genomic DNA target contained 10×PCR Buffer 1× (final concentration), 10 mM dNTPs 250 µM (final concentration), 50 mM Mg$^{++}$3 mM (final concentration), 10 µM Limiting Primer 50 nM (final concentration), 100 µM Excess Primer 1000 nM (final concentration), 10 µM signaling probe 100 nM (final concentration), 10 µM of quencher probe 100 nM (final concentration), 1.25 Units Platinum Taq DNA polymerase, and 10$^6$ bacterial genomic DNA starting copies. A Taq polymerase-only control (NTC) containing Taq polymerase and all of the above reagents but no genomic DNA was also amplified.

Amplification and detection of three replicate samples of each target and each control were performed with a Bio Rad (Hercules, Calif., USA) IQ5 real-time thermocycler using the following protocol: denaturation at 95° C. for three minutes, followed by 50 cycles of 95° C. for 10 seconds, 65° C. for 15 seconds and 72° C. for 45 seconds. Following amplification a melt curve was generated starting at 25° C. and progressing to 80° C. in one-degree steps of thirty seconds each and then an anneal curve was generated starting at 80° C. and progressing to 25° C. in one degree steps of thirty seconds each, with data acquisition of Quasar 670 fluorescence at each step. The various first derivative anneal curves are shown in FIG. 22. Fluorescence intensities were normalized to 75° C. and with background fluorescence of the NTC control at 75° C. subtracted, and then the highest fluorescent value normalized to 1.0. FIG. 22 presents the first-derivative annealing curves for the samples tested. In FIG. 22, circle 229 is the NTC, circle 230 is HAR22IVH, circle 231 is AR43/3330.1IVE, circle 232 is CA05IVA, circle 233 is WISV, circle 234 is Q2314IVC, circle 235 is HDE288VI, circle 236 are N315II and JCSC4469IVD, circle 237 is 85/2082III, circle 238 are COL1 and 8/6-3PIVB, and circle 239 is BK20781VIII.

Table 6 above lists the spa types of the twelve MRSA samples that were tested. Some of the samples have the same spa types, others have similar spa types, and still others have very different spa types. Results in FIG. 22 showed the expected differentiation and definition of each spa type. When spa types were expected to be the same, the same signature appeared, see COL1 and 8/6-3P IVB; and N315 and JCSC4469 IVD.

The scope is not to be limited by the specific features and embodiments described above. Various modifications of these embodiments can be made without departing from the the inventive concepts described herein. Such modifications are intended to fall within the scope of the appended claims.

We claim:

1. A kit for analyzing at least one single-stranded nucleic acid target sequence in a sample, comprising multiple detectably distinguishable probe sets, each of the multiple detectably distinguishable probe sets comprising two probes:
   i) a probe labeled with a non-fluorescent quencher moiety that hybridizes to a first region of one of the at least one single-stranded nucleic acid target sequence, and
   ii) a probe labeled with a fluorescent moiety that hybridizes to a second region of said one of the at least one single-stranded nucleic acid target sequence adjacent to the first region of said one of the at least one single-stranded nucleic acid target sequence,
   wherein after the multiple detectably distinguishable probe sets hybridize to said one of the at least one single-stranded nucleic acid target sequence, the multiple detectably distinguishable probe sets are arranged adjacent to each other on said one of the at least one single-stranded nucleic acid target sequence, and there is no un-hybridized nucleotide between each of the multiple detectably distinguishable probe sets;
   wherein the at least one single-stranded nucleic acid target sequence is found in an organism, wherein at least one identical probe exists in two sets of the multiple detectably distinguishable probe sets;
   wherein upon hybridization of said probe labeled with a fluorescent moiety to said one of said at least one single-stranded nucleic acid target sequence in said sample in the absence of the hybridization of said probe labeled with a non-fluorescent quencher moiety to said one of said at least one single-stranded nucleic acid target sequence, said fluorescent moiety from said probe labeled with a fluorescent moiety emits a fluorescent signal, wherein, if both the probe labeled with a non-fluorescent quencher moiety and the probe labeled with a fluorescent moiety of at least one probe set of the multiple detectably distinguishable probe sets hybridize to said one of said at least one single-stranded nucleic acid target sequence, the non-fluorescent quencher moiety from the probe labeled with a non-fluorescent quencher moiety quenches the fluorescent signal from the fluorescent moiety from the probe labeled with a fluorescent moiety.

2. The kit of claim 1, wherein one probe is a part of a set of the multiple detectably distinguishable probe sets.

3. The kit of claim 2 wherein a first set and a second set of the multiple detectably distinguishable probe sets collectively comprise:
   (A) a quencher probe comprising a non-fluorescent quencher moiety on its one end that is the probe labeled with a non-fluorescent quencher moiety in the first set of the two of the multiple detectably distinguishable probe sets;
   (B) a first signaling probe comprising a fluorescent moiety on its first end and a non-fluorescent quencher moiety on its second end that is the probe labeled with a fluorescent moiety in the first set of the multiple detectably distinguishable probe sets and the probe labeled with a non-fluorescent quencher moiety in the second set of the multiple detectably distinguishable probe sets; and
   (C) a second signaling probe comprising a fluorescent moiety on its first end and a non-fluorescent quencher moiety on its second end that is the probe labeled with a fluorescent moiety in the second set of the two of the multiple detectably distinguishable probe sets;
   wherein upon hybridization of the multiple detectably distinguishable probe sets to said one of said at least one single-stranded nucleic acid target sequence, the non-fluorescent quencher moiety of the quencher probe interacts with the fluorescent moiety of the first signaling probe and the non-fluorescent quencher moiety of the first signaling probe interacts with the fluorescent moiety of the second signaling probe.

4. The kit of claim 1, wherein the probe labeled with a fluorescent moiety in each set of the multiple detectably distinguishable probe sets is also labeled with a non-fluorescent quencher moiety.

5. The kit of claim 1, wherein a first set and a second set of the multiple detectably distinguishable probe sets collectively comprise:
   (A) a quencher probe comprising a non-fluorescent quencher moiety on its one end that is the probe labeled with a non-fluorescent quencher moiety in the first set of the multiple detectably distinguishable probe sets;
   (B) a first signaling probe comprising a fluorescent moiety on its first end and a non-fluorescent quencher moiety on its second end that is the probe labeled with a fluorescent moiety in the first set of the multiple detectably distinguishable probe sets and the probe labeled with a non-fluorescent quencher moiety in the second set of the multiple detectably distinguishable probe sets; and (C) a second signaling probe comprising a fluorescent moiety on its first end and a non-fluorescent quencher moiety on its second end that is the probe labeled with a fluorescent moiety in the second set of the two of the multiple detectably distinguishable probe sets;

wherein upon hybridization of the multiple detectably distinguishable probe sets to said one of said at least one single-stranded nucleic acid target sequence, the non-fluorescent quencher moiety of the quencher probe interacts with the fluorescent moiety of the first signaling probe and the non-fluorescent quencher moiety of the first signaling probe interacts with the fluorescent moiety of the second signaling probe.

6. The kit of claim 1, wherein the melting temperature of the probe labeled with a fluorescent moiety in at least one set of the multiple detectably distinguishable probe sets is higher than the melting temperature of its corresponding probe labeled with a non-fluorescent quencher moiety of the at least one set of the multiple detectably distinguishable probe sets.

7. The kit of claim 1 wherein the concentration of the probe labeled with a fluorescent moiety of at least one set of the multiple detectably distinguishable probe sets is lower than the concentration of its corresponding probe labeled with a non-fluorescent quencher moiety of the at least one set of the multiple detectably distinguishable probe sets.

8. The kit of claim 1 wherein, when the probe labeled with a non-fluorescent quencher moiety and the probe labeled with a fluorescent moiety in a probe set of the multiple detectably distinguishable probe sets hybridize to said one of said at least one single-stranded nucleic acid target sequence, said fluorescent moiety in the probe labeled with a fluorescent moiety and said non-fluorescent quencher moiety in the probe labeled with a non-fluorescent quencher moiety in the probe set of the multiple detectably distinguishable probe sets undergo a fluorescence resonance energy transfer (FRET).

9. The kit of claim 1 wherein said fluorescent moiety and said non-fluorescent quencher moiety of at least one set of the multiple detectably distinguishable probe sets are close proximity and interact with each other upon hybridization of the at least one set of the multiple detectably distinguishable probe sets to said one of said at least one single-stranded nucleic acid target sequence.

10. The kit of claim 1 further comprising primers for amplifying said at least one single stranded nucleic acid target sequence.

11. The kit of claim 10, wherein said amplifying said at least one single stranded nucleic acid target sequence is performed by PCR amplification.

12. The kit of claim 10, wherein the probes in the multiple detectably distinguishable probe sets have melting temperatures below the annealing temperature of at least one of the primers.

13. The kit of claim 1 wherein said multiple detectably distinguishable probe sets comprise three or more probe sets.

14. The kit of claim 11, wherein said PCR amplification is LATE-PCR amplification.

15. The kit of claim 1, wherein the organism is selected from bacteria, fungi, protozoa, humans and other animals, green plants, and blue green algae.

* * * * *

SEQUENCE LISTING

```
<160> NUMBER OF SEQ ID NOS: 90

<210> SEQ ID NO 1
<211> LENGTH: 31
<212> TYPE: DNA
<213> ORGANISM: Artificial Sequence
<220> FEATURE:
<223> OTHER INFORMATION: Synthetic

<400> SEQUENCE: 1
ctccagccag gcacgctcac gtgacagacc g                                    31

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
ccggtggtcg ccgcgatcaa ggag                                            24

<210> SEQ ID NO 3
<211> LENGTH: 150
<212> TYPE: DNA
<213> ORGANISM: Mycobacterium tuberculosis

<400> SEQUENCE: 3
ccggtggtcg ccgcgatcaa ggagttcttc ggcaccagcc agctgagcca attcatggac      60
cagaacaacc cgctgtcggg gttgacccac aagcgccgac tgtcggcgct ggggcccggc     120
ggtctgtcac gtgagcgtgc cgggctggag                                     150

<210> SEQ ID NO 4
<211> LENGTH: 150
<212> TYPE: DNA
<213> ORGANISM: Mycobacterium tuberculosis

<400> SEQUENCE: 4
ccggtggtcg ccgcgatcaa ggagttcttc ggcaccagcc agctgagcca attcatggtc      60
cagaacaacc cgctgtcggg gttgacccac aagcgccgac tgtcggcgct ggggcccggc     120
ggtctgtcac gtgagcgtgc cgggctggag                                     150

<210> SEQ ID NO 5
```

```
<211> LENGTH: 150
<212> TYPE: DNA
<213> ORGANISM: Mycobacterium tuberculosis

<400> SEQUENCE: 5
ccggtggtcg ccgcgatcaa ggagttcttc ggcaccagcc agctgagcca attcatggac    60
cagaacaacc cgctgtcggg gttgacccac aagcgccgac tgttggcgct ggggcccggc   120
ggtctgtcac gtgagcgtgc cgggctggag                                   150

<210> SEQ ID NO 6
<211> LENGTH: 16
<212> TYPE: DNA
<213> ORGANISM: Artificial Sequence
<220> FEATURE:
<223> OTHER INFORMATION: Synthetic

<400> SEQUENCE: 6
ctggttggtg cagaag                                                   16

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
tcaggtccat gaattggctc aga                                           23

<210> SEQ ID NO 8
<211> LENGTH: 12
<212> TYPE: DNA
<213> ORGANISM: Artificial Sequence
<220> FEATURE:
<223> OTHER INFORMATION: Synthetic

<400> SEQUENCE: 8
cagcgggttg tt                                                       12

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
atgcgcttgt ggatcaaccc cgat                                          24

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10
aagccccagc gccgacagtc gtt                                           23

<210> SEQ ID NO 11
<211> LENGTH: 12
<212> TYPE: DNA
<213> ORGANISM: Artificial Sequence
<220> FEATURE:
<223> OTHER INFORMATION: Synthetic
```

<400> SEQUENCE: 11
acagaccgcc gg                                                      12

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
accagggctg ggccatgcgc acca                                         24

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
ggaccgcagc cacgccaagt c                                            21

<210> SEQ ID NO 14
<211> LENGTH: 113
<212> TYPE: DNA
<213> ORGANISM: Mycobacterium tuberculosis

<400> SEQUENCE: 14
ggaccgcagc cacgccaagt cggcccggtc ggttgccgag accatgggca actaccaccc    60
gcacggcgac gcgtcgatct acgacagcct ggtgcgcatg gcccagccct ggt          113

<210> SEQ ID NO 15
<211> LENGTH: 113
<212> TYPE: DNA
<213> ORGANISM: Mycobacterium tuberculosis

<400> SEQUENCE: 15
ggaccgcagc cacgccaagt cggcccggtc ggttgccgag accatgggca actaccaccc    60
gcacggcgac gtgtcgatct acgacagcct ggtgcgcatg gcccagccct ggt          113

<210> SEQ ID NO 16
<211> LENGTH: 10
<212> TYPE: DNA
<213> ORGANISM: Artificial Sequence
<220> FEATURE:
<223> OTHER INFORMATION: Synthetic

<400> SEQUENCE: 16
cgaccgggcc                                                         10

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
aacccatggt ctcggcaact t                                            21

<210> SEQ ID NO 18

```
<211> LENGTH: 22
<212> TYPE: DNA
<213> ORGANISM: Artificial Sequence
<220> FEATURE:
<223> OTHER INFORMATION: Synthetic

<400> SEQUENCE: 18
aatcgccgtg cgggtggtag tt                                              22

<210> SEQ ID NO 19
<211> LENGTH: 19
<212> TYPE: DNA
<213> ORGANISM: Artificial Sequence
<220> FEATURE:
<223> OTHER INFORMATION: Synthetic

<400> SEQUENCE: 19
gctgtcgtag atcgacgcg                                                  19

<210> SEQ ID NO 20
<211> LENGTH: 37
<212> TYPE: DNA
<213> ORGANISM: Artificial Sequence
<220> FEATURE:
<223> OTHER INFORMATION: Synthetic

<400> SEQUENCE: 20
agcgcccact cgtagccgta caggatctcg aggaaac                              37

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21
tcttgggctg gaagagctcg tatggcac                                        28

<210> SEQ ID NO 22
<211> LENGTH: 139
<212> TYPE: DNA
<213> ORGANISM: Mycobacterium tuberculosis

<400> SEQUENCE: 22
gcttgggctg gaagagctcg tatggcaccg gaaccggtaa ggacgcgatc accagcggca     60
tcgaggtcgt atggacgaac accccgacga aatgggacaa cagtttcctc gagatcctgt    120
acggctacga gtgggagct                                                 139

<210> SEQ ID NO 23
<211> LENGTH: 139
<212> TYPE: DNA
<213> ORGANISM: Mycobacterium tuberculosis

<400> SEQUENCE: 23
gcttgggctg gaagagctcg tatggcaccg gaaccggtaa ggacgcgatc accaccggca     60
tcgaggtcgt atggacgaac accccgacga aatgggacaa cagtttcctc gagatcctgt    120
acggctacga gtgggagct                                                 139

<210> SEQ ID NO 24
<211> LENGTH: 139
<212> TYPE: DNA
<213> ORGANISM: Mycobacterium tuberculosis
```

<400> SEQUENCE: 24
gcttgggctg aagagctcg tatggcaccg aaccggtaa ggacgcgatc accaacggca    60
tcgaggtcgt atgacgaac accccgacga atgggacaa cagtttcctc gagatcctgt    120
acggctacga gtgggagct                                                139

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
aagtgatcgc gtccttacct t                                             21

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
gacctcgatg cagctg                                                   16

<210> SEQ ID NO 27
<211> LENGTH: 150
<212> TYPE: DNA
<213> ORGANISM: Mycobacterium tuberculosis

<400> SEQUENCE: 27
ccggtggtcg ccgcgatcaa ggagttcttc ggcaccagcc agctgagcca attcatggac    60
cagaacaacc cgctgtcggg gttgaccgac aagcgccgac tgtcggcgct ggggcccggc    120
ggtctgtcac gtgagcgtgc cgggctggag                                    150

<210> SEQ ID NO 28
<211> LENGTH: 36
<212> TYPE: DNA
<213> ORGANISM: Artificial Sequence
<220> FEATURE:
<223> OTHER INFORMATION: Synthetic

<400> SEQUENCE: 28
ggttatacct agtataattg gtggttttgg taattg                             36

<210> SEQ ID NO 29
<211> LENGTH: 36
<212> TYPE: DNA
<213> ORGANISM: Artificial Sequence
<220> FEATURE:
<223> OTHER INFORMATION: Synthetic

<400> SEQUENCE: 29
ggttatacct agtataattg gtggttttgg taactg                             36

<210> SEQ ID NO 30
<211> LENGTH: 36
<212> TYPE: DNA
<213> ORGANISM: Artificial Sequence
<220> FEATURE:
<223> OTHER INFORMATION: Synthetic

```
<400> SEQUENCE: 30
ggttatacct agtataattg gtggttttgg caattg                                36

<210> SEQ ID NO 31
<211> LENGTH: 36
<212> TYPE: DNA
<213> ORGANISM: Artificial Sequence
<220> FEATURE:
<223> OTHER INFORMATION: Synthetic

<400> SEQUENCE: 31
actaggatca aaaaagaag tattaaaatt acgatc                                 36

<210> SEQ ID NO 32
<211> LENGTH: 460
<212> TYPE: DNA
<213> ORGANISM: Caenorhabditis elegans

<400> SEQUENCE: 32
tcttggatca aaaaatgaag tatttaaatt acgatcagtt aacaacatag taatagcccc      60
tgctaaaacc ggtagagata aaccagtaa aaacactgtt acaaatacag ttcaaacaaa      120
taaagttata tgttctaatg aaatagaact tctacgtaaa ttttttagtag tacacataaa    180 attaatacca cctaagatag atcttaaccc tgctgcatgt aaactaaaaa tagctaaatc     240
tactctactt ccagggtgcc ccattgttct taaaggtggg tagactgttc acctagtccc     300
acaacctata tctacaaaac aagcatctaa aattaataat atagatgtag gtaataacca    360
aaatcttaaa ttatttaaac gtggaaatct tatatcaggt gctcctaaca taagtggtaa    420
taatcagtta ccaaaaccac cgattatagt aggtattacc                           460

<210> SEQ ID NO 33
<211> LENGTH: 450
<212> TYPE: DNA
<213> ORGANISM: Steinernema feltiae
<220> FEATURE:
<221> NAME/KEY: misc_feature
<222> LOCATION: (437)..(450)
<223> OTHER INFORMATION: n is a, c, g, or t

<400> SEQUENCE: 33
tctaggatca aaaaagaag tatttaaatt acggtctgta agaagtatag taattgcccc      60
agctaaaacc ggtaaagaaa gaacaagaag gaaaactgta acaaaaacag ttcaaacaaa    120
aagactcata tgctctaaag aaatagagct tctacgaaga ttcttagtag tacatataaa    180
attaatagcc cccaaaatag agcttacacc agcacaatga agactaaaaa tagctaaatc    240
aaccctgttt ccaggatggc ctaaagtact taaaggagga taaacagttc aactagtacc    300
acaccctgta tctacaaaac aagcatctaa aattaataat atagcagtgg gtaataacca    360
aaaacttaaa ttatttaaac gaggaaatct tatatccgga gcaccaagaa ggaactaatc    420
aatttccaaa tcctccnnnn nnnnnnnnnn                                      450

<210> SEQ ID NO 34
<211> LENGTH: 40
<212> TYPE: DNA
<213> ORGANISM: Artificial Sequence
<220> FEATURE:
<223> OTHER INFORMATION: Synthetic

<400> SEQUENCE: 34
aatattacct ttgatgttag gggctcctga tataagtttt                           40
```

<210> SEQ ID NO 35
<211> LENGTH: 45
<212> TYPE: DNA
<213> ORGANISM: Artificial Sequence
<220> FEATURE:
<223> OTHER INFORMATION: Synthetic

<400> SEQUENCE: 35
atcctcgttt aaataattta agtttttgat tattacctac ttcat        45

<210> SEQ ID NO 36
<211> LENGTH: 47
<212> TYPE: DNA
<213> ORGANISM: Artificial Sequence
<220> FEATURE:
<223> OTHER INFORMATION: Synthetic

<400> SEQUENCE: 36
tttgttttgt tgttgggatt cttgttttgt tgatataggt ggtggaa        47

<210> SEQ ID NO 37
<211> LENGTH: 35
<212> TYPE: DNA
<213> ORGANISM: Artificial Sequence
<220> FEATURE:
<223> OTHER INFORMATION: Synthetic

<400> SEQUENCE: 37
aactggttga actgtttacc ctcctttaag aactt        35

<210> SEQ ID NO 38
<211> LENGTH: 45
<212> TYPE: DNA
<213> ORGANISM: Artificial Sequence
<220> FEATURE:
<223> OTHER INFORMATION: Synthetic

<400> SEQUENCE: 38
aagtaggtca tcctggtagt actgtagatt ttgttatttt tactt        45

<210> SEQ ID NO 39
<211> LENGTH: 38
<212> TYPE: DNA
<213> ORGANISM: Artificial Sequence
<220> FEATURE:
<223> OTHER INFORMATION: Synthetic

<400> SEQUENCE: 39
atgcatggtg ctggttttag ttctattttg ggtgctat        38

<210> SEQ ID NO 40
<211> LENGTH: 42
<212> TYPE: DNA
<213> ORGANISM: Artificial Sequence
<220> FEATURE:
<223> OTHER INFORMATION: Synthetic

<400> SEQUENCE: 40
attaatttta tgggtactac tgttaagaat ctgcgtagtt at        42

<210> SEQ ID NO 41
<211> LENGTH: 43
<212> TYPE: DNA
<213> ORGANISM: Artificial Sequence
<220> FEATURE:

<223> OTHER INFORMATION: Synthetic

<400> SEQUENCE: 41
ttctatttct ttggaacata tgagtctgtt tgtttggact gaa                43

<210> SEQ ID NO 42
<211> LENGTH: 36
<212> TYPE: DNA
<213> ORGANISM: Artificial Sequence
<220> FEATURE:
<223> OTHER INFORMATION: Synthetic

<400> SEQUENCE: 42
tttttgtgac tgttttttg ttggttctgt ctctaa                         36

<210> SEQ ID NO 43
<211> LENGTH: 40
<212> TYPE: DNA
<213> ORGANISM: Artificial Sequence
<220> FEATURE:
<223> OTHER INFORMATION: Synthetic

<400> SEQUENCE: 43
ttcctgtttt aggtggggct attactatat tgttaactaa                    40

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
ccagactcct acgggaggca gcagt                                    25

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45
gtattaccgc ggctgctggc a                                        21

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
aaggggaata ttgcacaatg gtt                                      23

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
aagcgaaagc ctgatgcagc catt                                     24

```
<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48
tagccgcgtg tgtgaagaat a                                          21

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
ttggccttcg gattgtaaag cacttaa                                    27

<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
tattagtagg gaggaagta                                             19

<210> SEQ ID NO 51
<211> LENGTH: 29
<212> TYPE: DNA
<213> ORGANISM: Artificial Sequence
<220> FEATURE:
<223> OTHER INFORMATION: Synthetic

<400> SEQUENCE: 51
ttatatgtgt aagtaactgt gcacatcaa                                  29

<210> SEQ ID NO 52
<211> LENGTH: 16
<212> TYPE: DNA
<213> ORGANISM: Artificial Sequence
<220> FEATURE:
<223> OTHER INFORMATION: Synthetic

<400> SEQUENCE: 52
ttgacgttac ccgcaa                                                16

<210> SEQ ID NO 53
<211> LENGTH: 26
<212> TYPE: DNA
<213> ORGANISM: Artificial Sequence
<220> FEATURE:
<223> OTHER INFORMATION: Synthetic

<400> SEQUENCE: 53
ttgaagaagc accggctaac tccgaa                                     26

<210> SEQ ID NO 54
<211> LENGTH: 25
<212> TYPE: DNA
<213> ORGANISM: Artificial Sequence
<220> FEATURE:
<223> OTHER INFORMATION: Synthetic
```

<400> SEQUENCE: 54
ccagactcct acgggaggca gcagt                                     25

<210> SEQ ID NO 55
<211> LENGTH: 29
<212> TYPE: DNA
<213> ORGANISM: Artificial Sequence
<220> FEATURE:
<223> OTHER INFORMATION: Synthetic

<400> SEQUENCE: 55
tggactacca gggtatctaa tcctgtttg                                 29

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
atagggtgcg agcgttaatc t                                         21

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
aaggatttac tgggcgtaaa gcgtt                                     25

<210> SEQ ID NO 58
<211> LENGTH: 24
<212> TYPE: DNA
<213> ORGANISM: Artificial Sequence
<220> FEATURE:
<223> OTHER INFORMATION: Synthetic

<400> SEQUENCE: 58
ttgcgtaggc ggcttattaa gtaa                                      24

<210> SEQ ID NO 59
<211> LENGTH: 24
<212> TYPE: DNA
<213> ORGANISM: Artificial Sequence
<220> FEATURE:
<223> OTHER INFORMATION: Synthetic

<400> SEQUENCE: 59
aacggatgtg aaatccccga gctt                                      24

<210> SEQ ID NO 60
<211> LENGTH: 22
<212> TYPE: DNA
<213> ORGANISM: Artificial Sequence
<220> FEATURE:
<223> OTHER INFORMATION: Synthetic

<400> SEQUENCE: 60
taacttggga attgcattcg ta                                        22

<210> SEQ ID NO 61
<211> LENGTH: 23

```
<212> TYPE: DNA
<213> ORGANISM: Artificial Sequence
<220> FEATURE:
<223> OTHER INFORMATION: Synthetic

<400> SEQUENCE: 61
atactggtga gctagagtat gat                                          23

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gaagaggatg gtagaattcc                                              20

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
taggtgtagc ggtgaaatgc gta                                          23

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
aaggggaata ttgcacaatg gtt                                          23

<210> SEQ ID NO 65
<211> LENGTH: 24
<212> TYPE: DNA
<213> ORGANISM: Artificial Sequence
<220> FEATURE:
<223> OTHER INFORMATION: Synthetic

<400> SEQUENCE: 65
aagcgaaagc ctgatgcagc catt                                         24

<210> SEQ ID NO 66
<211> LENGTH: 21
<212> TYPE: DNA
<213> ORGANISM: Artificial Sequence
<220> FEATURE:
<223> OTHER INFORMATION: Synthetic

<400> SEQUENCE: 66
tagccgcgtg tgtgaagaat a                                            21

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
```
ttggccttcg gattgtaaag cacttaa                                          27

<210> SEQ ID NO 68
<211> LENGTH: 19
<212> TYPE: DNA
<213> ORGANISM: Artificial Sequence
<220> FEATURE:
<223> OTHER INFORMATION: Synthetic

<400> SEQUENCE: 68
tattagtagg gaggaagta                                                   19

<210> SEQ ID NO 69
<211> LENGTH: 29
<212> TYPE: DNA
<213> ORGANISM: Artificial Sequence
<220> FEATURE:
<223> OTHER INFORMATION: Synthetic

<400> SEQUENCE: 69
ttatatgtgt aagtaactgt gcacatcaa                                        29

<210> SEQ ID NO 70
<211> LENGTH: 16
<212> TYPE: DNA
<213> ORGANISM: Artificial Sequence
<220> FEATURE:
<223> OTHER INFORMATION: Synthetic

<400> SEQUENCE: 70
ttgacgttac ccgcaa                                                      16

<210> SEQ ID NO 71
<211> LENGTH: 26
<212> TYPE: DNA
<213> ORGANISM: Artificial Sequence
<220> FEATURE:
<223> OTHER INFORMATION: Synthetic

<400> SEQUENCE: 71
ttgaagaagc accggctaac tccgaa                                           26

<210> SEQ ID NO 72
<211> LENGTH: 27
<212> TYPE: DNA
<213> ORGANISM: Artificial Sequence
<220> FEATURE:
<223> OTHER INFORMATION: Synthetic

<400> SEQUENCE: 72
gtgaagggat tacaaggcgt gaggcac                                          27

<210> SEQ ID NO 73
<211> LENGTH: 23
<212> TYPE: DNA
<213> ORGANISM: Artificial Sequence
<220> FEATURE:
<223> OTHER INFORMATION: Synthetic

<400> SEQUENCE: 73
ggactactta gcctccaatt cac                                              23

<210> SEQ ID NO 74
<211> LENGTH: 26
<212> TYPE: DNA
<213> ORGANISM: Artificial Sequence
<220> FEATURE:
<223> OTHER INFORMATION: Synthetic

<400> SEQUENCE: 74
cgatatttat tccaacatac accgtg                                        26

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
ccgatcaaaa tttatatt                                                 18

<210> SEQ ID NO 76
<211> LENGTH: 40
<212> TYPE: DNA
<213> ORGANISM: Artificial Sequence
<220> FEATURE:
<223> OTHER INFORMATION: Synthetic

<400> SEQUENCE: 76
cgcggcgtca ggcatatagg ataccgggac agacgccgcg                         40

<210> SEQ ID NO 77
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(13)
<223> OTHER INFORMATION: The residues at these positions are linked to a
      C3 spacer.

<400> SEQUENCE: 77
cgtaattata atattataat tacg                                          24

<210> SEQ ID NO 78
<211> LENGTH: 33
<212> TYPE: DNA
<213> ORGANISM: Artificial Sequence
<220> FEATURE:
<223> OTHER INFORMATION: Synthetic

<400> SEQUENCE: 78
ctgtatcacc aggtttaacg acatgtactc cgt                                33

<210> SEQ ID NO 79
<211> LENGTH: 23
<212> TYPE: DNA
<213> ORGANISM: Artificial Sequence
<220> FEATURE:
<223> OTHER INFORMATION: Synthetic

<400> SEQUENCE: 79
gctaaatgat gctcaagcac caa                                           23

<210> SEQ ID NO 80
<211> LENGTH: 509
<212> TYPE: DNA
<213> ORGANISM: Staphylococcus aureus

<400> SEQUENCE: 80

```
ctgtatcacc aggtttaacg acatgtactc cgttgccgtc ttctttacca ggcttgttgc      60
catcttcttt accaggcttg ttgccatctt ctttaccagg cttgttgcca tcttctttac     120
caggcttgtt gccgtcttct ttaccaggtt tgttgccatc ttctttgcca ggttttttgt     180
tgtcttcttt accaggtttg ttgccgtctt ctttgccagg ttttttgttg tcttcttac     240 caggtttgtt gccgtcttct ttaccaggct tgttgttgtc ttctttgcca ggcttgttgt     300
tgtcttcctc ttttggtgct tgagcatcgt ttagcttttt agcttctgct aaaatttctt     360
tgctcactga aggatcgtct ttaaggcttt ggatgaagcc gttacgttgt tcttcagtta     420
agttaggtaa atgtaaaatt tcatagaaag cattttgttg ttctttgttg aatttgttgt     480
cagcttttgg tgcttgtgca tcatttagc                                       509
```

```
<210> SEQ ID NO 81
<211> LENGTH: 25
<212> TYPE: DNA
<213> ORGANISM: Artificial Sequence
<220> FEATURE:
<223> OTHER INFORMATION: Synthetic

<400> SEQUENCE: 81
aaccaggctt gttgttgtct tcttt                                            25
```

```
<210> SEQ ID NO 82
<211> LENGTH: 26
<212> TYPE: DNA
<213> ORGANISM: Artificial Sequence
<220> FEATURE:
<223> OTHER INFORMATION: Synthetic

<400> SEQUENCE: 82
aagccaggtt ttttgccatc ttcttt                                           26
```

```
<210> SEQ ID NO 83
<211> LENGTH: 232
<212> TYPE: DNA
<213> ORGANISM: Klebsiella pneumonia

<400> SEQUENCE: 83
gtccagactc ctacgggagg cagcagtggg gaatattgca caatgggcgc aagcctgatg      60
cagccatgcc gcgtgtgtga agaaggcctt cgggttgtaa agcactttca gcggggagga     120
aggcggtgag gttaataacc tcatcgattg acgttacccg cagaagaagc accggctaac     180
tccgtgccag cagccgcggt aatacggagg gtgcaagcgt taatcggaat ta             232
```

```
<210> SEQ ID NO 84
<211> LENGTH: 232
<212> TYPE: DNA
<213> ORGANISM: Enterobacter aerogenes

<400> SEQUENCE: 84
gtccagactc ctacgggagg cagcagtggg gaatattgca caatgggcgc aagcctgatg      60
cagccatgcc gcgtgtatga agaaggcctt cgggttgtaa agtactttca gcgaggagga     120
aggcattgtg gttaataacc gcagtgattg acgttactcg cagaagaagc accggctaac     180
tccgtgccag cagccgcggt aatacggagg gtgcaagcgt taatcggaat ta             232
```

```
<210> SEQ ID NO 85
<211> LENGTH: 233
<212> TYPE: DNA
```

<213> ORGANISM: Acinetobacter baumannii

<400> SEQUENCE: 85

```
gcccagactc ctacgggagg cagcagtggg gaatattgga caatggggggg aaccctgatc    60
cagccatgcc gcgtgtgtga agaaggcctt atggttgtaa agcactttaa gcgaggagga   120
ggctacttta gttaatacct agagatagtg gacgttactc gcagaataag caccggctaa   180
ctctgtgcca gcagccgcgg taatacagag ggtgcgagcg ttaatcggat tta          233
```

<210> SEQ ID NO 86
<211> LENGTH: 232
<212> TYPE: DNA
<213> ORGANISM: Pseudomonas aeruginosa

<400> SEQUENCE: 86

```
gtccagactc ctacgggagg cagcagtggg gaatattgga caatgggcga aagcctgatc    60
cagccatgcc gcgtgtgtga agaaggtctt cggattgtaa agcactttaa gttgggagga   120
agggcagtaa gttaatacct tgctgttttg acgttaccaa cagaataagc accggctaac   180
ttcgtgccag cagccgcggt aatacgaagg gtgcaagcgt taatcggaat ta           232
```

<210> SEQ ID NO 87
<211> LENGTH: 232
<212> TYPE: DNA
<213> ORGANISM: Staphylococcus aureus

<400> SEQUENCE: 87

```
gtccagactc ctacgggagg cagcagtagg gaatcttccg caatgggcga aagcctgacg    60
gagcaacgcc gcgtgagtga tgaaggtctt cggatcgtaa aactctgtta ttagggaaga   120
acatatgtgt aagtaactgt gcacatcttg acggtaccta atcagaaagc cacggctaac   180
tacgtgccag cagccgcggt aatacgtagg tggcaagcgt tatccggaat ta           232
```

<210> SEQ ID NO 88
<211> LENGTH: 232
<212> TYPE: DNA
<213> ORGANISM: Staphylococcus epidermidis

<400> SEQUENCE: 88

```
gtccagactc ctacgggagg cagcagtagg gaatcttccg caatgggcga aagcctgacg    60
gagcaacgcc gcgtgagtga tgaaggtctt cggatcgtaa aactctgtta ttagggaaga   120
acaaatgtgt aagtaactat gcacgtcttg acggtaccta atcagaaagc cacggctaac   180
tacgtgccag cagccgcggt aatacgtagg tggcaagcgt tatccggaat ta           232
```

<210> SEQ ID NO 89
<211> LENGTH: 232
<212> TYPE: DNA
<213> ORGANISM: Enterococcus faecalis

<400> SEQUENCE: 89

```
gcccagactc ctacgggagg cagcagtagg gaatcttcgg caatggacga aagtctgacc    60
gagcaacgcc gcgtgagtga agaaggtttt cggatcgtaa aactctgttg ttagagaaga   120
acaaggacgt tagtaactga acgtcccctg acggtatcta accagaaagc cacggctaac   180
tacgtgccag cagccgcggt aatacgtagg tggcaagcgt tgtccggatt ta           232
```

<210> SEQ ID NO 90
<211> LENGTH: 540

```
<212> TYPE: DNA
<213> ORGANISM: Acinetobacter baumannii

<400> SEQUENCE: 90
cactgggact gagacacggc ccagactcct acgggaggca gcagtgggga atattggaca        60 atgggggaa  ccctgatcca gccataccgc gtgtgtgaag aaggccttat ggttgtaaag       120
cactttaagc gaggaggagg ctactttagt taatacctag ggatagtgga cgttactcgc       180
agaataagca ccggctaact ctgtgccagc agccgcggta atacagaggg tgcgagcgtt       240
aatcggattt actgggcgta aagcgtgcgt aggcggctta ttaagtcgga tgtgaaatcc       300
ccgagcttaa cttgggaatt gcattcgata ctggtgagct agagtatggg agaggatggt       360
agaattccag gtgtagcggt gaaatgcgta gagatctgga ggaataccga tggcgaaggc       420
agccatctgg cctaatactg acgctgaggt acgaaagcat ggggagcaaa caggattaga      480
taccctggta gtccatgccg taaacgatgt ctactagccg ttggggcctt tgaggcttta       540
```